United States Patent
Carmel et al.

(10) Patent No.: US 8,308,724 B2
(45) Date of Patent: *Nov. 13, 2012

(54) BIPOLAR ELECTROSURGICAL DEVICE WITH FLOATING-POTENTIAL ELECTRODES

(75) Inventors: Yuval Carmel, Rockville, MD (US);
Robert A. Van Wyk, Largo, FL (US);
Anatoly Shkvarunets, Rockville, MD (US)

(73) Assignee: ElectroMedical Associates, LLC, Bethesda, MD (US)

( * ) Notice: Subject to any disclaimer, the term of this patent is extended or adjusted under 35 U.S.C. 154(b) by 700 days.

This patent is subject to a terminal disclaimer.

(21) Appl. No.: 12/488,787

(22) Filed: Jun. 22, 2009

(65) Prior Publication Data

US 2010/0016854 A1 Jan. 21, 2010

Related U.S. Application Data

(63) Continuation of application No. 10/911,309, filed on Aug. 4, 2004, now Pat. No. 7,563,261.

(60) Provisional application No. 60/493,729, filed on Aug. 11, 2003.

(51) Int. Cl.
*A61B 18/14* (2006.01)

(52) U.S. Cl. .............. 606/50; 606/41; 606/48

(58) Field of Classification Search ............ 606/41, 606/45, 48–50

See application file for complete search history.

(56) References Cited

U.S. PATENT DOCUMENTS

| | | | |
|---|---|---|---|
| 2,448,741 A | 9/1948 | Scott et al. | |
| 3,856,015 A | 12/1974 | Iglesias | |
| 3,901,242 A | 8/1975 | Storz | |
| 4,674,499 A | 6/1987 | Pao | |
| 4,682,596 A | 7/1987 | Bales | |
| 4,726,370 A | 2/1988 | Karasawa | |
| 4,917,082 A | 4/1990 | Grossi et al. | |
| 5,195,959 A | 3/1993 | Smith | |
| 5,277,696 A | 1/1994 | Hagen | |
| 5,314,459 A * | 5/1994 | Swanson et al. | 607/122 |
| 5,647,840 A | 7/1997 | D'Ameliao et al. | |
| 5,709,698 A | 1/1998 | Adams et al. | |
| 5,782,289 A | 7/1998 | Mastrorio et al. | |
| 6,033,400 A | 3/2000 | Grossi et al. | |
| 6,066,134 A | 5/2000 | Eggers | |
| 6,113,597 A | 9/2000 | Eggers et al. | |
| 6,169,926 B1 * | 1/2001 | Baker | 607/99 |
| 6,197,025 B1 | 3/2001 | Grossi et al. | |
| 6,235,020 B1 | 5/2001 | Cheng et al. | |
| 6,379,351 B1 | 4/2002 | Thapliyal et al. | |
| 6,391,025 B1 * | 5/2002 | Weinstein et al. | 606/41 |
| 6,419,684 B1 | 7/2002 | Heisler et al. | |
| 6,468,274 B1 | 10/2002 | Alleyne et al. | |
| 6,565,560 B1 | 5/2003 | Goble et al. | |
| 6,575,968 B1 | 6/2003 | Eggers | |
| 6,582,423 B1 | 6/2003 | Thapliyal et al. | |

(Continued)

*Primary Examiner* — Michael Peffley
(74) *Attorney, Agent, or Firm* — Chalin A. Smith; Smith Patent Consulting

(57) ABSTRACT

An electrosurgical instrument, system, and methods are provided for the vaporization, cutting, coagulation, or treatment of tissue in the presence of an electrically conductive fluid medium. The electrosurgical probe comprises at least one active electrode, and at least one "floating" electrode having at least one end in close proximity to at least one active electrode. The floating electrode is not connected in any way to the electrosurgical power supply, but rather has a "floating" potential determined by the shape and position of the electrode. The floating electrode increases current density in the region of the probe distal end.

27 Claims, 49 Drawing Sheets

U.S. PATENT DOCUMENTS

| | | |
|---|---|---|
| 6,770,070 B1 | 8/2004 | Balbierz |
| 6,796,982 B2 | 9/2004 | Carmel et al. |
| 6,840,937 B2 | 1/2005 | Van Wyk |
| 6,899,712 B2 | 5/2005 | Moustafis et al. |
| 6,920,883 B2 | 7/2005 | Bessette et al. |
| 6,921,398 B2 | 7/2005 | Carmel et al. |
| 6,921,399 B2 | 7/2005 | Carmel et al. |
| 6,955,676 B2 | 10/2005 | Quick |
| 7,066,936 B2 | 6/2006 | Ryan |
| 7,166,103 B2 | 1/2007 | Carmel et al. |
| 2001/0001314 A1 | 5/2001 | Davison et al. |
| 2002/0038122 A1 | 3/2002 | Peters et al. |
| 2002/0120261 A1 | 8/2002 | Morris et al. |
| 2002/0133148 A1 | 9/2002 | Daniel et al. |
| 2002/0133149 A1 | 9/2002 | Bessette |
| 2004/0006336 A1 | 1/2004 | Swanson |
| 2004/0006339 A1 | 1/2004 | Underwood et al. |
| 2004/0030330 A1 | 2/2004 | Brassel et al. |
| 2004/0049183 A1 | 3/2004 | Ellman et al. |
| 2004/0104455 A1 | 6/2004 | Shimizu |
| 2004/0106919 A1 | 6/2004 | Hood |
| 2004/0193150 A1 | 9/2004 | Sharkey et al. |
| 2005/0065510 A1 | 3/2005 | Carmel et al. |
| 2005/0234446 A1 | 10/2005 | Van Wyk et al. |
| 2006/0259031 A1 | 11/2006 | Carmel et al. |
| 2006/0293653 A1 | 12/2006 | Van Wyk |

\* cited by examiner

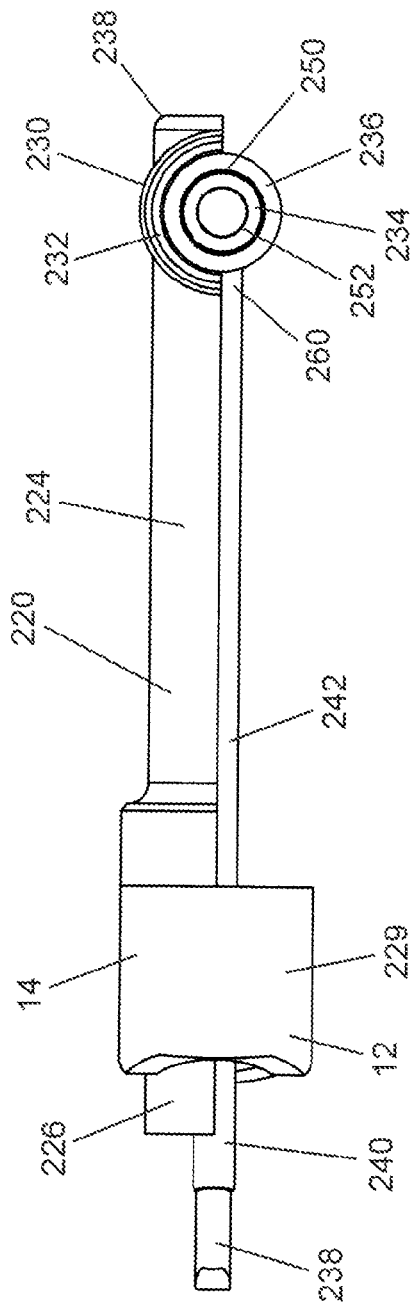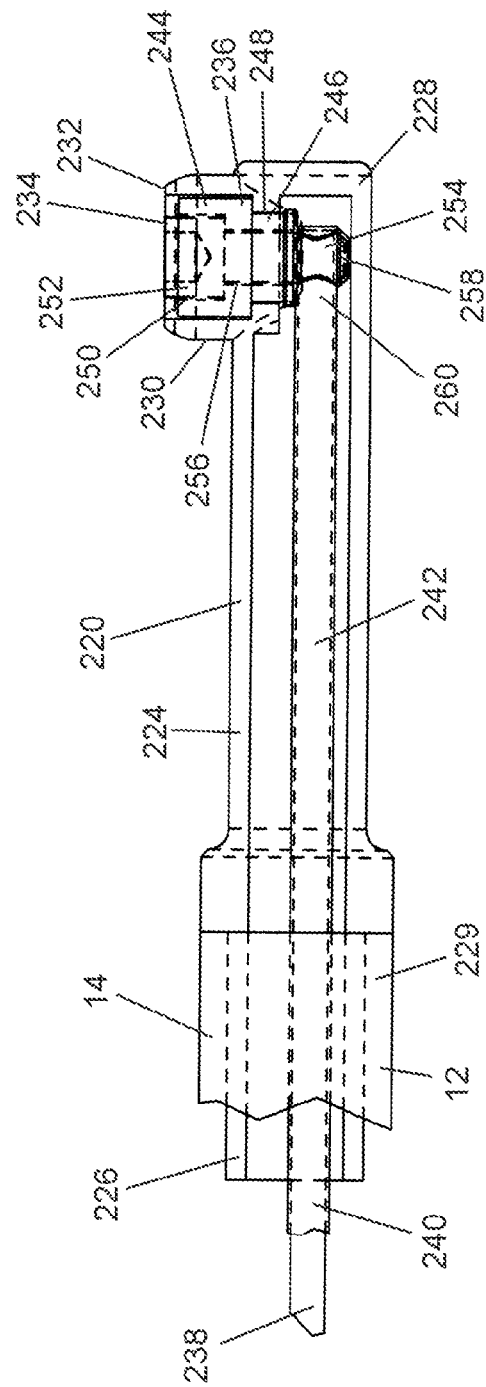

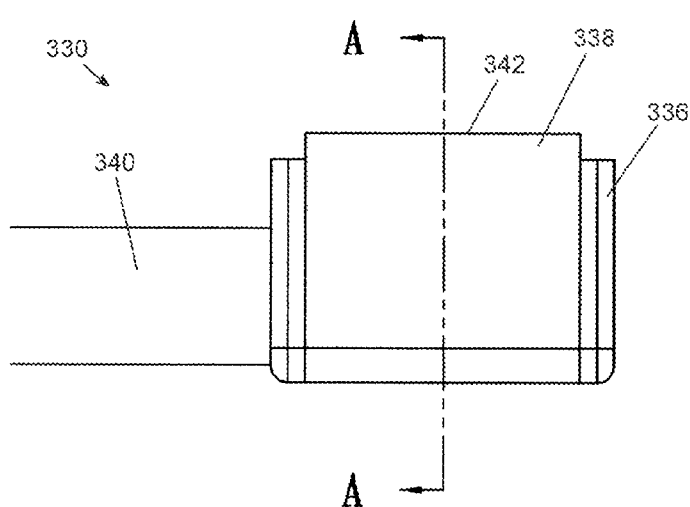
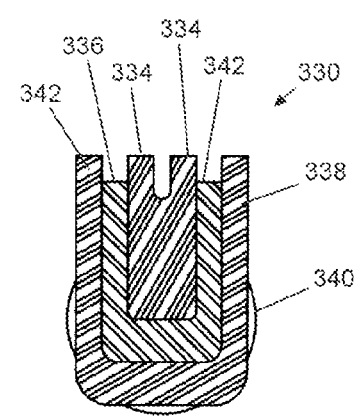
Fig. 49
Fig. 50

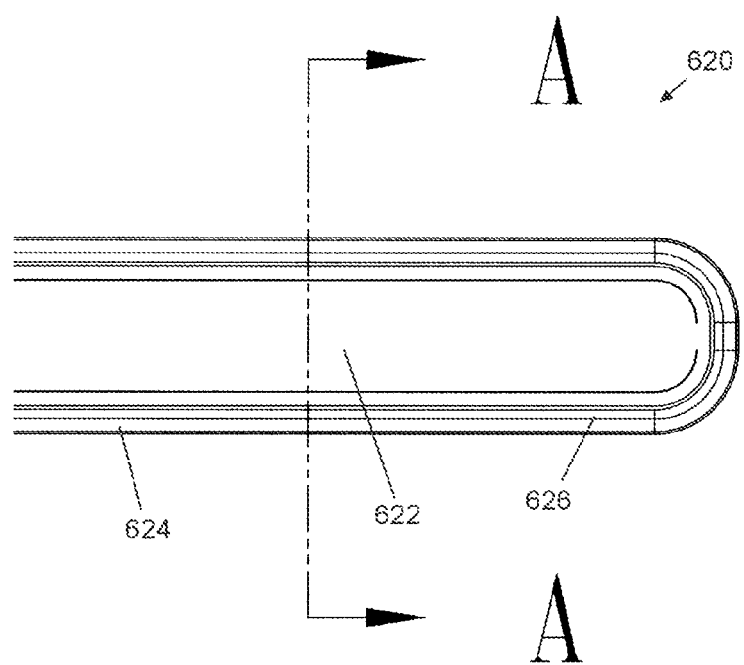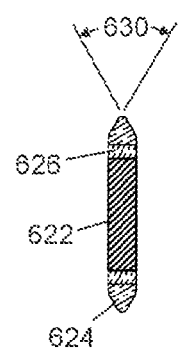
Fig. 59
Fig. 60

BIPOLAR ELECTROSURGICAL DEVICE WITH FLOATING-POTENTIAL ELECTRODES

PRIORITY

The instant application is a continuation of U.S. patent application Ser. No. 10/911,309, filed Aug. 4, 2004, now U.S. Pat. No. 7,563,261 issued Jul. 21, 2009, which, in turn, claims the benefit of provisional application 60/493,729 filed Aug. 11, 2003. The instant application is also related to U.S. patent application Ser. No. 11/136,514, filed May 25, 2005, now U.S. Pat. No. 7,566,333 issued Jul. 28, 2009, which, in turn, claims the benefit of provisional application 60/648,105 filed Jan. 28, 2005. The contents of these prior applications are incorporated by reference herein in their entirety.

BACKGROUND OF THE INVENTION

The present invention relates generally to the field of electrosurgery, and, more particularly, to high efficiency surgical devices and methods which use high frequency (RF) electrical power for cutting, bulk removal by vaporization (ablation), coagulation and treatment of tissue in a conductive liquid environment, as well as other forms of tissue treatment such as shrinking, lesion formation, sculpting and thermal treatment with or without externally supplied liquids.

Least invasive surgical techniques have gained significant popularity because of their ability to accomplish outcomes with reduced patient pain and accelerated return of the patient to normal activities. Arthroscopic surgery, in which the intra-articular space is filled with conducting fluid, allows orthopedists to efficiently perform procedures using special purpose instruments designed specifically for arthroscopists. Among these special purpose tools are various manual graspers and biters, powered shaver blades and burs, and electrosurgical devices. Electrosurgical procedures usually require a proper electrosurgical generator, which supplies the Radio Frequency (RF) electrical power, and a proper surgical electrode (also known as an electrosurgical probe). Under appropriate conditions the desired surgical effects are accomplished.

Note: in common terminology and as used herein the term "electrode" may refer to one or more components of an electrosurgical device (such as an active electrode or a return electrode) or to the entire device, as in an "ablator electrode". Electrosurgical devices may also be referred to as "probes".

Arthroscopic electrosurgical procedures rely on the application of RF electrical power using an electrode (or probe) for cutting, ablation or coagulation of tissue structures in a joint space which is filled by liquid. Many types of electrosurgical devices can be used, however, they can be divided to two general categories, monopolar devices and bipolar devices. When monopolar electrosurgical devices are used, the RF current generally flows from an exposed active electrode through the patient's body, to a passive, return current electrode that is externally attached to a suitable location on the patient body. In this way the patient's body is part of the return current circuit. When bipolar electrosurgical devices are used, both the active and the return current electrodes are exposed, and are typically positioned in close proximity. The RF current flows from the active electrode to the return electrode through the nearby tissue and conductive fluids. Monopolar and bipolar devices in many fields of electrosurgery operate according to the same principles.

During the last several years, specialized arthroscopic electrosurgical probes called ablators have been developed. Exemplary of these instruments are ArthroWands manufactured by Arthrocare (Sunnyvale, Calif.), VAPR electrodes manufactured by Mitek Products Division of Johnson & Johnson (Westwood, Mass.) and electrodes by Oratec Interventions, Inc. (Menlo Park, Calif.), Stryker Corporation (Kalamazoo, Mich.) and Smith and Nephew Endoscopy (Andover, Mass.). These ablators differ from conventional arthroscopic electrosurgical probes in that they are designed for the bulk removal of tissue by vaporization in a conductive liquid environment rather than for the cutting of tissue or for coagulation of bleeding vessels.

Recently the use of electrosurgery with conductive fluids for urology, gynecology and other procedures is also becoming popular. Previously, mostly non-conductive fluids were used for these applications.

While standard electrodes are capable of ablation their geometries are not efficient for accomplishing this task. During ablation water within the target tissue is vaporized. Because volumes of tissue are vaporized rather than discretely cut out and removed from the surgical site, the power requirements of ablator electrodes are generally higher than those of other arthroscopic electrosurgical electrodes. The geometry and design of the electrode and the characteristics of the RF power supplied to the electrode greatly affect the power required for ablation (vaporization) of tissue. Electrodes with inefficient designs will require higher power levels than those with efficient designs.

During electrosurgery procedures in conductive fluids, most of the RF energy delivered to an electrode is dissipated in the fluid and in the adjacent tissue as heat, thereby raising the temperature of the fluid within the cavity and of the adjacent tissue. A substantial fraction of the RF power is used for the creation of sparks (arcs) in the vicinity of the electrodes. These sparks accomplish the tissue vaporization, cutting and coagulation. In summary, the sparks are essential for tissue vaporization (ablation), while heating of the liquid and tissue away from the active electrode tip always occurs but has no desirable clinical effect.

The heating of the irrigation fluid and especially the adjacent tissue is not beneficial to the patient. On the contrary, this may substantially increase the likelihood of patient burns. For this and other reasons, improved, efficient electrosurgical electrodes are desirable for tissue vaporization and cutting of tissue structures.

An electrosurgical probe, in general, is composed of a metallic conductor surrounded by a dielectric insulator (for example plastic, ceramic or glass) except for the exposed metallic electrode. The probe electrode is often immersed in a conducting fluid and is brought in contact with the tissue structure during the electrosurgical procedure. The probe is energized, typically at a voltage of few hundred to few thousand volts, using an RF generator operating at a frequency between 100 kHz to over 4 MHz. This voltage induces a current in the conductive liquid and nearby tissue. This current heats the liquid and tissue, the most intense heating occurring in the region very close to the electrode where the current density is highest. At points where the current density is sufficiently high, the liquid boils locally and many steam bubbles are created, the steam bubbles eventually insulating part or all of the electrode. Electrical breakdown in the form of an arc (spark) occurs in the bubbles which insulate the electrode. The sparks in these bubbles are channels of high temperature ionized gas, or plasma (temperature of about a few thousand degrees Kelvin). These high current density sparks, heat, evaporate (ablate) or cut the tissue (depending on the specific surgical procedure and the probe geometry) that is in contact with the spark.

The spark generation and tissue heating, modification or destruction very close to the electrode tip are beneficial and desirable effects. At the same time the induced current heats the liquid and tissue which is a little further away from the immediate vicinity of the electrode tip. This heating is undesirable and potentially dangerous because it may damage tissue structures uncontrollably in surrounding areas and also deep under the surface. The design of higher efficiency probes is desirable as it would lead to less heating of the fluid and tissue not in close proximity, and give the surgeon a larger margin of safety during the procedure.

Ablation (vaporizing) electrodes currently in use, whether monopolar or bipolar, have an active electrode surrounded by an insulator significantly larger in size than the ablating surface of the electrode. For ablators with a circular geometry, the diameter of the portion of the probe which generates ablative arcs (the "working" diameter) is generally not greater than 70 to 80 percent of the diameter of the insulator (the "physical" diameter) and therefore only about 50% of the physical probe area can be considered effective. This increases the size of the distal end of the electrode necessary to achieve a given ablative surface size, and necessitates the use of cannulae with relatively large lumens, an undesirable condition.

It is accordingly an object of this invention to produce an electrosurgical probe which has high efficiency.

It is also an object of this invention to produce an electrosurgical probe which has a distal end of compact size.

These and other objects are accomplished in the invention herein disclosed which is an advanced, high efficiency, electrosurgical probe equipped with an additional one or more metallic electrodes which are not connected directly to any part of power supply circuit. This electrode may contact the surrounding conducting liquid and/or tissue. The potential of this electrode is "floating" and is determined by the size and position of the electrode, the tissue type and properties, and the presence or absence of bodily fluids or externally supplied fluid. This "floating" electrode is mounted in such a way that one portion of the electrode is in close proximity to the probe tip, in the region of high potential. Another portion of the floating electrode is placed further away in a region of otherwise low potential.

The floating electrode generates and concentrates high power density in the vicinity of the active region, and results in more efficient liquid heating, steam bubble formation and bubble trapping in this region. This allows high efficiency operation, which allows the surgeon to substantially decrease the applied RF power and thereby reduce the likelihood of patient burns and injury.

These innovative electrosurgical devices with floating electrodes may be very effective in other medical procedures beyond evaporation (ablation), such as, for instance, for thermal treatments, lesion formation, tissue sculpting, and tissue "drilling", with or without externally supplied liquids.

SUMMARY OF THE INVENTION

An electrosurgical probe is a metallic electrode coated with dielectric except for an exposed portion at the electrode tip. This tip is an active element of the probe. When placed into conductive liquid-tissue media and energized, the probe induces electrical current in the conducting liquid and nearby tissue. This current deposits energy into the liquid and tissue raising their temperatures and creating the desired clinical effect. The highest energy deposition is in close proximity to the tip where current density is largest.

Power density in close proximity of the tip depends primarily on the applied voltage, the shape and size of the exposed portion of the electrode, and liquid/tissue electrical conductivity. Also it is affected by the return current electrode size, shape, and position. In general, positioning the return electrode into closer proximity to the active electrode increases the power density in the region near the electrode tip.

In the case of a monopolar probe, the return current is collected by a large return electrode (sometimes called dispersive electrode or return pad) placed on the patient's body far away from the probe tip. The power concentration capability of a monopolar probe is determined by the shape of the exposed electrode: the smaller and sharper the tip is, the better its power concentration capability.

In the case of bipolar probes the return current electrode is placed in moderate proximity to the active electrode (2-10 mm). Some additional power concentration takes place in comparison with the monopolar probe with the same shape of active electrode. The power concentration capability can be controlled additionally by the shape and position of the return electrode. Decreasing the distance between the return electrode and the active electrode increases the power concentration. A problem arises when the probe is generating sparks. (Recall that this is the goal of probe operation in ablation-tissue evaporation or cutting, for example). If the return electrode is placed sufficiently close to the tip to achieve a substantial increase of power concentration, the breakdown (arcing within bubbles) takes place between the tip and return electrode. The spark conductive channel connects the active electrode to the return current electrode and the power supply is loaded directly by the spark. Usually this leads to extra high-energy deposition in the spark between metallic electrodes resulting in localized melting and vaporization of the electrodes themselves. This results in shorting of the power supply and destruction of both the active and return electrodes with little clinical benefit to the patient.

A good bipolar probe design must avoid arcing between the active and return electrodes. Usually this is achieved by placing the return electrode a sufficiently large distance away from the active electrode to prevent direct breakdown between electrodes. Nevertheless, periodic arcing may take place so that both electrodes are eroded and eventually destroyed, especially in an aggressive mode of operation. Therefore, the additional degree of power concentration achievable by bipolar probes is severely limited.

The subject of this patent application is an electrosurgical device—with one or more additional metallic electrodes which are not connected directly to any part of the power supply circuit, and therefore are called "floating". These floating electrodes are in contact with the tissue or liquid in proximity to the active electrode. The electrical potential of these additional electrodes is not fixed, but rather is "floating" and is determined by size and position of the electrode and the electrical conductivity of the tissue/liquid surrounding the distal end of the device. This electrode is positioned in such a way that one end of the electrode is in close proximity to the active electrode. Another portion of the floating electrode is positioned in a region of low potential in the liquid. The addition of this floating potential electrode thereby substantially modifies the electrical field distribution, and energy deposition, in the vicinity of the active electrode without the possibility of electrode destruction since the floating electrode is not directly connected to the electrical power supply. This is demonstrated by two-dimensional numerical modeling, as shown in FIGS. 74 through 80. In the figures a section view through a probe distal tip is shown. Only the top half of the tip is shown. The tip is symmetrical about the bottom of the figure. In FIGS. 74 and 76, the energy deposition around an electrosurgical electrode with a single, cylindrically symmetric floating potential electrode is shown. FIG. 76 is an expanded view of the region in which the floating and active electrodes are in close proximity. In FIGS. 75 and 77 the energy deposition around a similar probe tip without a floating electrode is shown. FIG. 77 is an expanded view of the region in which the active electrode meets the insulator. The presence of the floating electrode concentrates the intensity over the physical area of the electrode. This is in contrast to the probe without a floating electrode, in which the energy density is concentrated around the active electrode only. FIG. 79 shows the power deposition around an electrosurgical probe with a floating electrode and as well as a return electrode on the probe in contact with the conductive fluid. FIG. 80 is an expanded view of the region of the probe of FIG. 79 in which the floating electrode and active electrode are in close proximity. FIG. 81 shows the power deposition in the region surrounding the active electrode of a probe like that shown in FIG. 79 but without a floating electrode. It is important to note that the floating electrode concentrates the power in the vicinity of the active electrode when the return is mounted on the probe in the same manner that it concentrates power when a remotely placed return electrode is used (for example, when a return electrode is externally attached to the patient's body).

In the absence of sparking (arcing within bubbles) this electrode increases power density in the vicinity of the probe tip. This is because the floating electrode extends from a high potential region (near the active electrode), to a region with low potential (farther from the active electrode), and "shorts" these points together. The probe floating potential will be in between the potentials of these points. The presence of the electrode decreases the potential near the active electrode, therefore increasing the electric field, current and power density in the region near the active electrode. A floating electrode works about the same way as any extended conductive object in the electrostatic field. The higher power density results in more efficient liquid heating and steam bubble formation, which allows one to decrease the power applied to a probe for a given effect. In the presence of the "floating" electrode more sparks are generated in the active region, since this region is larger. Bubble trapping is greatly enhanced with proper design of the floating electrode, insulator and the active electrode.

Sparks are an active element of an electrosurgical process. A spark is generated in a steam bubble if the bubble field (voltage difference across a bubble) is sufficient for breakdown. Usually sparks are generated in bubbles that are close to the active electrode of the probe because current density and field intensity are largest in this region.

The breakdown or spark inside a bubble is an electrically conductive channel of partly ionized pressurized gas. This medium is called highly collisional plasma. The basic property of this plasma is that the conductivity is proportional to the plasma density. Higher plasma temperatures are associated with higher ionization rates, plasma densities and conductivity.

Usually energy is deposited into highly collisional plasmas by electric current driven by voltage applied to electrodes at the ends of a plasma channel. In the case of a plasma channel formed inside of a bubble, the inner parts of the bubble surface with the largest voltage difference act as the electrodes to which the channel is connected. Most frequently, but not always, one of these electrodes is a metallic surface of the active electrode and the other is the opposite surface of the bubble or the surface of the tissue.

Electrically, the plasma channel is characterized by its impedance. The efficiency of energy deposition strongly depends on the ratio between the plasma channel and the power supply impedance. Efficiency (the portion of applied energy deposited to the plasma) as high as 50% can be achieved for matched conditions in which the power supply impedance equals the spark (plasma channel) impedance. If the channel impedance is too large or too small, the power deposition in the plasma is decreased. The power source for the plasma channel formation is the step voltage created by current flow in the conductive liquid surrounding the bubble. The effective impedance of the power supply is of the same order as the impedance of liquid with dimensions of a bubble. That means that the maximum power deposited into the arc channel is on the order of the power deposited into a volume of the bubble size filled with liquid. Deviation of the channel impedance from its optimum value results in decreased power deposition into the channel. These principles are valid if at least one of channel electrodes is the inner liquid surface of bubble.

The energy which is deposited to a plasma channel (spark) is determined by the energy density in the surrounding conductive liquid. As taught previously herein, the additional metallic "floating" electrode described in this patent application significantly increases the energy density in the region surrounding the active electrode. This makes it possible to substantially increase the power deposited into the spark. Since the floating electrode can be placed very close to the probe tip, the largest probability is for breakdown and plasma channel formation in the region between the two metallic electrodes—the active electrode and the floating potential electrode. The plasma channel current can now be supported not by a bubble size fraction of the induced current, but by a much larger volume of current flow that is determined by the size of floating electrode. This floating electrode additionally concentrates current delivered to the spark. The optimum spark current can be controlled by adjusting the size and position of the floating electrode. Arcing, then, can occur through bubbles between the active and floating electrodes, or from either electrode through bubbles in contact with an electrode.

In summary, the subject of this invention is an advanced, electrosurgical probe equipped with an additional "floating potential electrode". The floating electrode concentrates the power (i.e. increases the power density) in the active region, which leads to more efficient liquid heating, steam bubble formation, and spark generation in this region. The floating electrodes also strengthen the entire probe assembly by protecting the insulator (made of a ceramic or other dielectric). A properly designed floating electrode will favorably effect bubble formation and trapping, and therefore will enhance the probe's performance. This results in high efficiency operation, allowing the surgeon to substantially decrease the applied RF power, or shorten the procedure time, and thereby reduce the likelihood of patient burns and injury, while at the same time maintaining high performance operation. Arcing occurs from the floating electrode as well as the active electrode resulting in a probe in which the distal tip has a "working" diameter equal to the "physical" diameter in the case of probes having a radial symmetry. This is in contrast to an electrically active area normally being only about 50% of the physical area of the device.

In some embodiments the probes have a radial symmetry with the floating electrode forming the outermost radial surface at the probe tip. The floating electrode may completely or only partially surround the tip, and may have features to locally increase the current density such as, for instance, notches or protuberances. In other embodiments the probe tip has a non-radial symmetry with the floating electrode completely or partially surrounding the active electrode, while in other embodiments the floating and active electrode form an array of protuberances with the floating electrodes being interspersed in the array of active electrodes. In yet other embodiments the active and floating electrodes form an assembly having a blade-like structure useful for cutting tissue.

The active and floating electrodes may be formed and arranged in a variety of configurations to accomplish tissue vaporization for a range of applications and conditions. These include, but are not limited to, bulk tissue vaporization, tissue cutting, and producing holes in tissue. Because the field is intensified, the time required to form steam bubbles and achieve arcing within the bubbles is shortened.

The current invention is useful also for medical procedures in which tissue is thermally treated rather than removed by vaporization, such as, for instance, cardiology, oncology and treatment of tumors, sometimes referred to as lesion formation. In these applications the device is brought into close proximity, or contact, with tissue with or without the presence of externally applied conductive fluid at the site for thermal treatment. The voltage applied to the active electrode is reduced to a level which produces current densities insufficient for forming sparks and the associated bubbles. Tissue is heated to a desired temperature for a predetermined time sufficient for lesion formation. The floating electrode intensifies the electric field in the region surrounding the active electrode so as to produce a larger, more controlled and more uniform lesion.

Some probes used for thermal treatment have geometries designed for heating without the forming of the bubbles which lead to arcing and tissue vaporization. In these embodiments it is desirable to have a more uniform current density at the active and floating electrodes. Accordingly, features such as notches, grooves, ribs or protuberances, for locally increasing the current density are absent. The active and floating electrodes may be, for instance, rings displaced axially on a probe shaft, either a single active and single floating electrode, or multiples of either the active electrode or floating electrode, or multiples of both. The active and floating electrodes may completely, or only partially surround the probe tip.

The innovative approach of incorporating a floating electrode (or electrodes) for the concentration of power in the active area may be advantageously applied to probes used with remotely located return electrodes, and to probes having a the return electrode located on the probe itself (in the vicinity of the active area).

BRIEF DESCRIPTION OF THE DRAWINGS

FIG. 37 is a plan view of the objects of FIG. 36.

FIG. 38 is a side elevational view of the objects of FIG. 36.

FIG. 49 is a side elevational view of the object of FIG. 48.

FIG. 50 is an end sectional view of the object of FIG. 48.

FIG. 59 is an expanded side elevational view of the object of FIG. 57.

FIG. 60 is a distal end sectional view of the object of FIG. 59.

DESCRIPTION OF THE EMBODIMENTS

Figure 1:
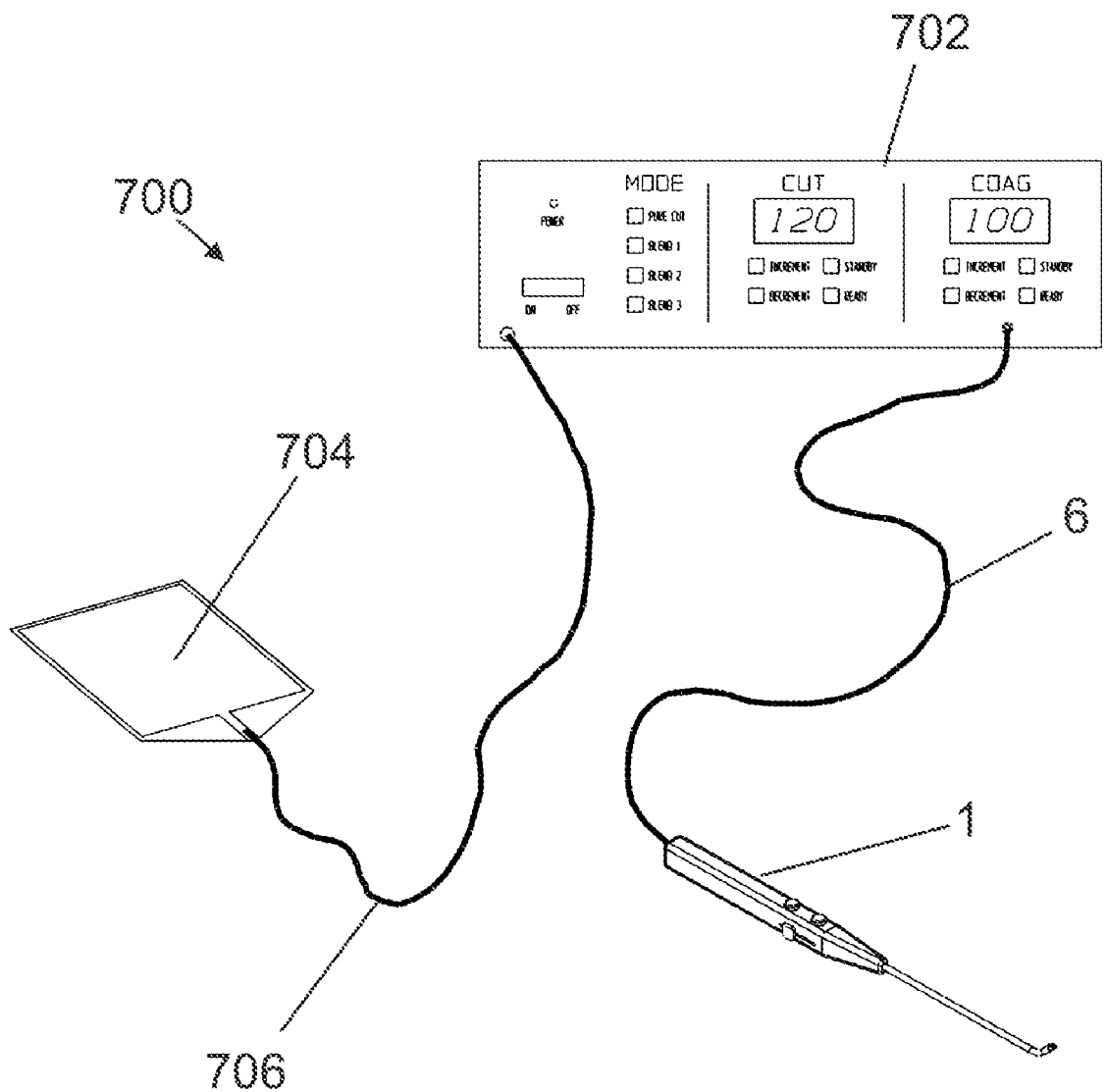
FIG. 1 is a perspective view of an electrosurgical system, including an power supply, a dispersive (return) electrode, wiring, and an electrosurgical probe constructed in accordance with the principles of this invention.

Referring to FIG. 1, electrosurgical system 700 has an electrosurgical power supply 702, an electrosurgical probe 1 with electrical cord 6, and a dispersive (return) electrode 704 with electrical cord 706.

Figure 2:
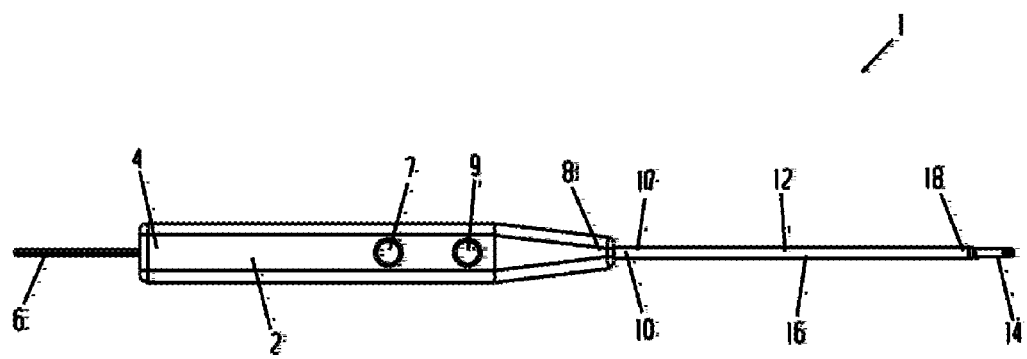
FIG. 2 is a plan view of an arthroscopic ablator electrode made in accordance with the principles of this invention.
Figure 3:
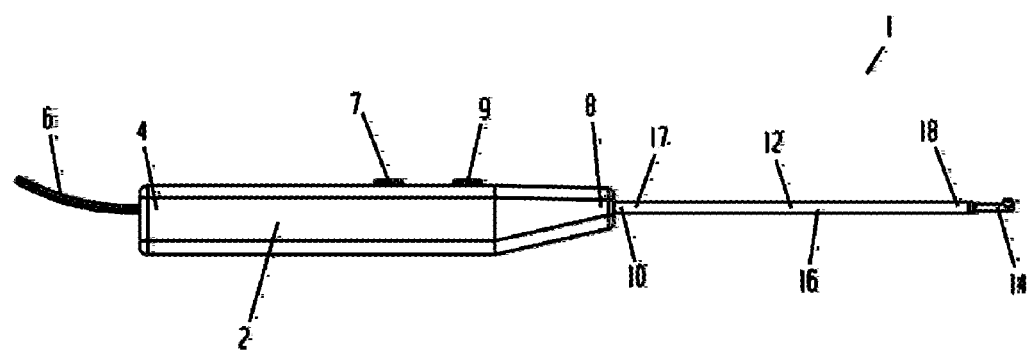
FIG. 3 is a side elevational view of the objects of FIG. 1.
Figure 4:
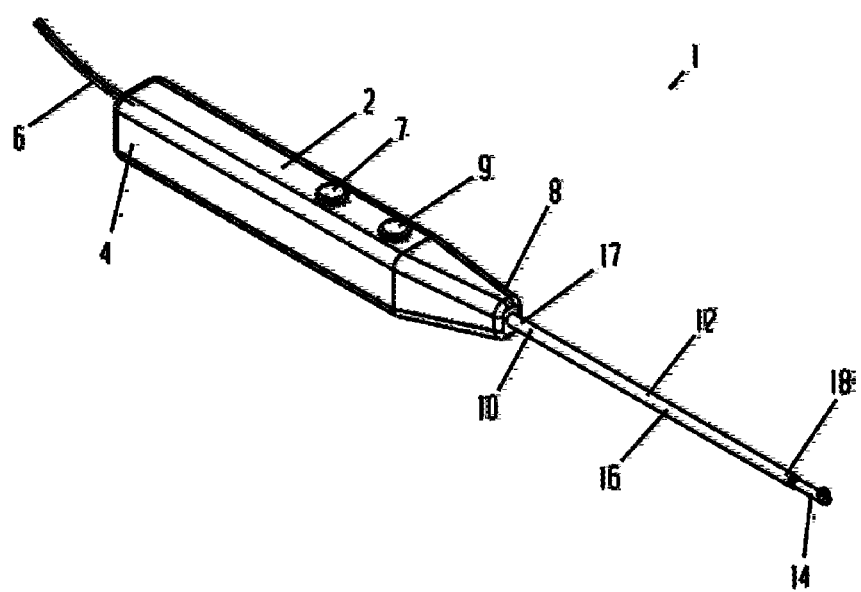
FIG. 4 is a perspective view of the object of FIG. 1.

Referring FIGS. 2 through 4, probe 1 has a proximal portion 2 forming a handle and having a proximal end 4 from which passes electrical cord 6, and a distal end 8 which attaches to proximal end 10 of elongated distal portion 12. Distal portion 12 has a distal end 14 and a tubular portion 16. Tubular portion 16 has a proximal end 17 and a distal end 18. Buttons 7 and 9 control the RF power applied to the probe.

Distal end 14 is an assembly having an active electrode, a ring electrode, a ceramic or other dielectric insulator placed between the active and ring electrodes, and a dielectric coating which covers at least a portion of the distal end assembly. The distal end assembly and its components are shown in FIGS. 5 through 17.

Figure 5:
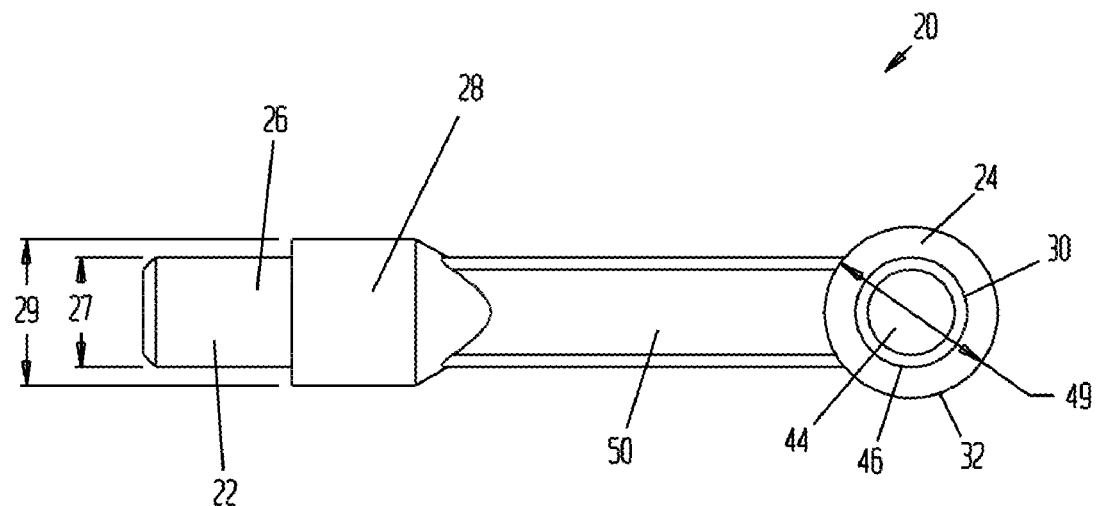
FIG. 5 is an expanded plan view of the active electrode at the distal end of the object of FIG. 1.
Figure 6:
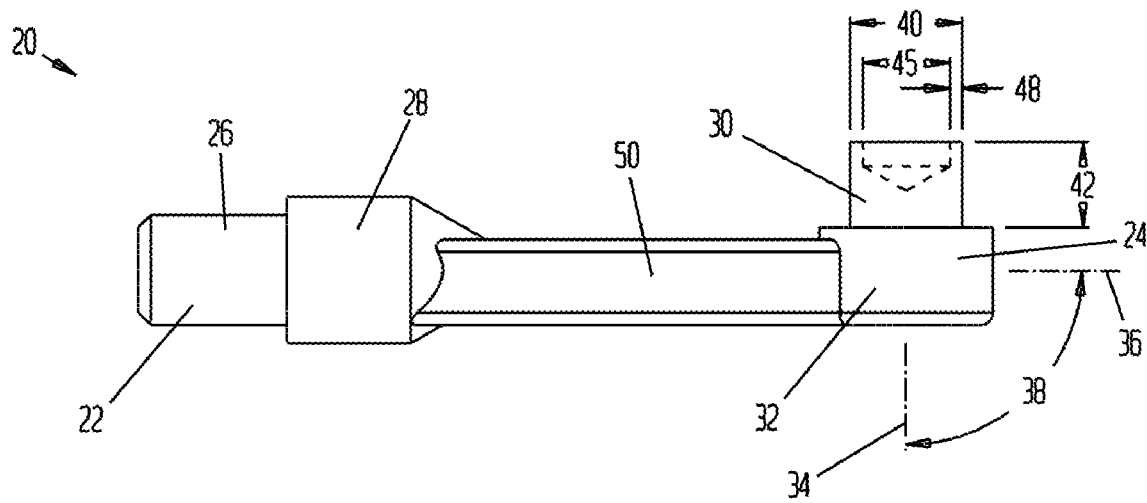
FIG. 6 is a side elevational view of the object of FIG. 5.
Figure 7:
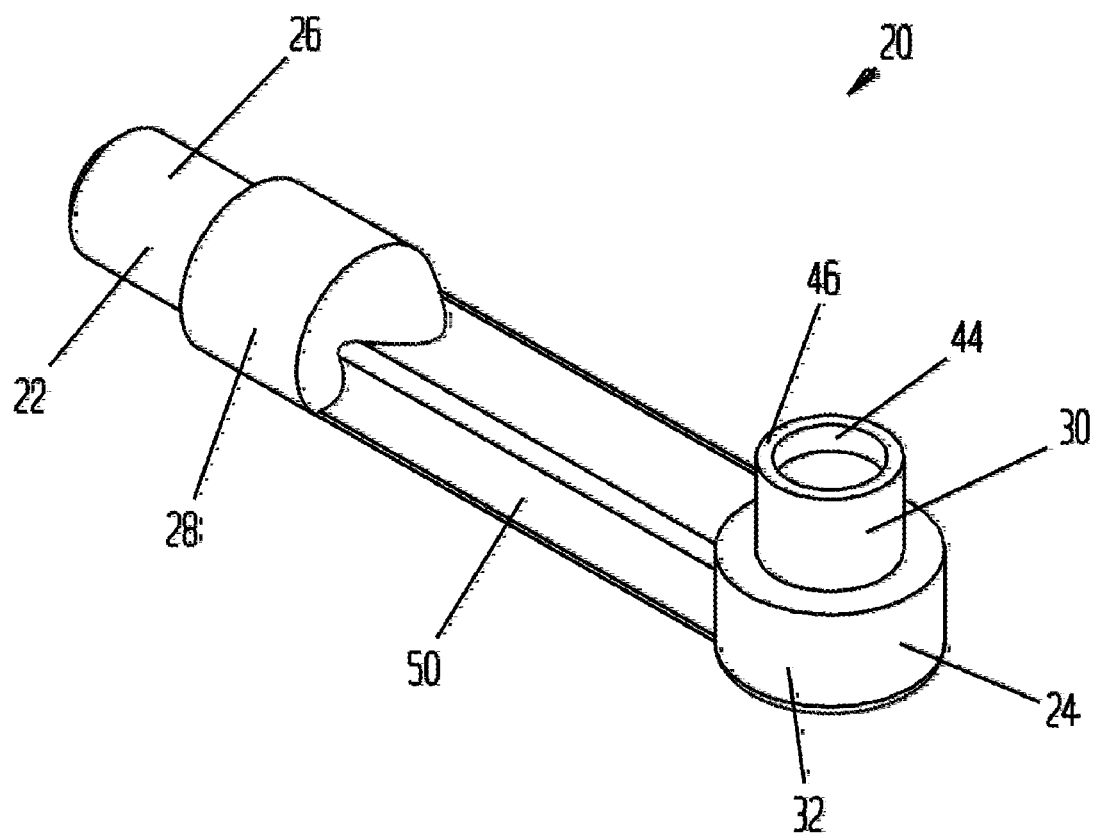
FIG. 7 is a perspective view of the object of FIG. 5.

Referring to FIGS. 5 through 7, active electrode 20 has a proximal end 22 and a distal end 24. Proximal end 22 forms a longitudinal cylindrical portion 26 having a diameter 27 slightly larger than the lumen of distal end 18 of tubular portion 16 (FIGS. 2 through 4) such that electrode 20 can be assembled to tubular portion 16 using a press fit. Cylindrical portion 28, coaxial with portion 26, has a diameter 29 approximately equal to the outer diameter of distal end 18 of tubular portion 16. Distal end 24 has an upper cylindrical portion 30 and a lower coaxial cylindrical portion 32. The axis 34 of cylindrical portions 30 and 32 and the axis 36 of proximal cylindrical portion 26 form an angle 38. Angle 38 is 90 degrees in the example shown. Angle 38 may be in the range from 0 to 90 degrees. Upper cylindrical portion 30 of diameter 40 and length 42 has a recessed cylindrical pocket 44 of diameter 45 in its upper surface so as to form a rim 46 of width 48. Lower cylindrical portion 32 has a diameter 49. Proximal end 22 and distal end 24 are joined by elongated portion 50 which has a rectangular cross-section, although other cross-sections may be used. Electrode 20 is manufactured by machining from bar stock or, more preferably by metal injection molding. Electrode 20 is made of a suitable metallic material such as, for instance, stainless steel, nickel, tungsten or titanium.

Figure 8:
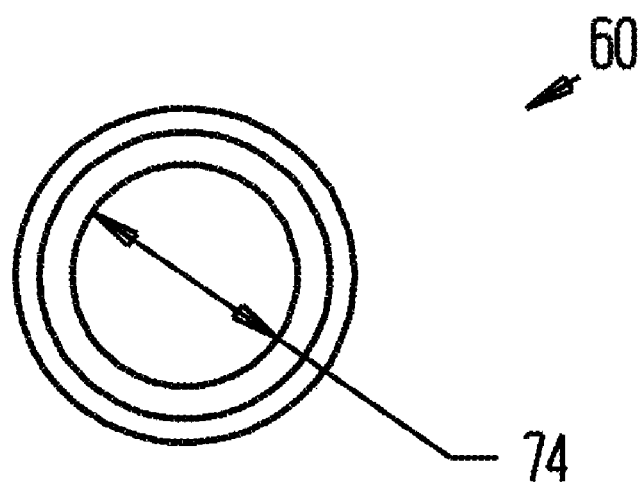
FIG. 8 is a plan view of the insulator at the distal tip of the object of FIG. 1.
Figure 9:
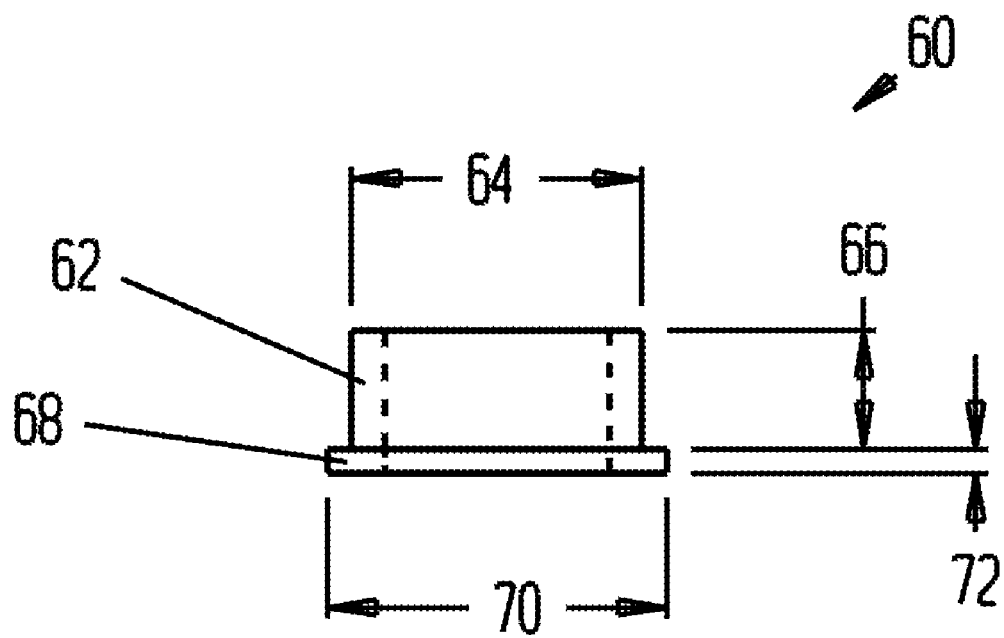
FIG. 9 is a front elevational view of the object of FIG. 8.

Referring to FIGS. 8 and 9, insulator 60 has a cylindrical tubular form having an upper portion 62 of diameter 64 and length 66 and a lower portion 68 of diameter 70 and length 72. Inner diameter 74 of insulator 60 is slightly larger than diameter 40 of upper cylindrical portion 30 of active electrode 20. Diameter 70 of lower portion 68 is approximately equal to diameter 49 of lower cylindrical portion 32 of active electrode 20. Insulator 60 is made of a suitable dielectric material such as, for instance, alumina or zirconia.

Figure 10:
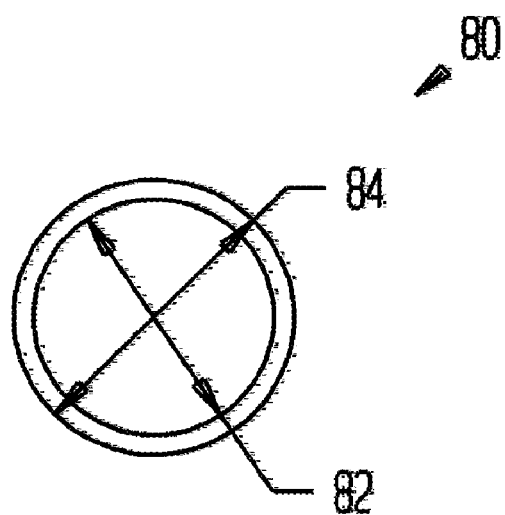
FIG. 10 is a plan view of the floating electrode at the distal tip of the object of FIG. 1.
Figure 11:
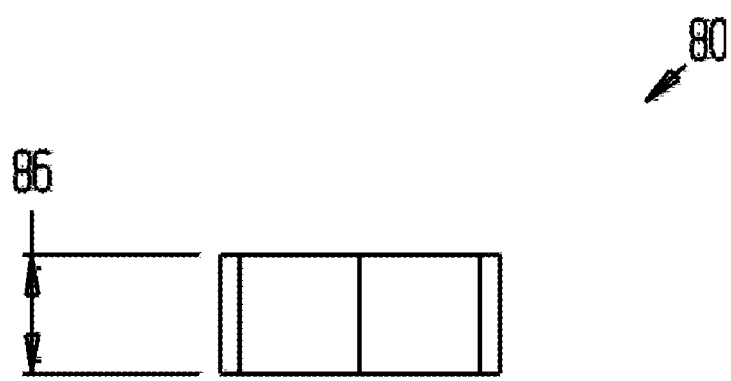
FIG. 11 is a front elevational view of the object of FIG. 10.

Referring to FIGS. 10 and 11, ring electrode 80 has a cylindrical tubular form having an inner diameter 82 approximately equal to diameter 64 of upper portion 62 of insulator 60, and an outer diameter 84 approximately equal to diameter 70 of lower portion 68 of insulator 60. Ring electrode 80 has a length 86.

Figure 12:
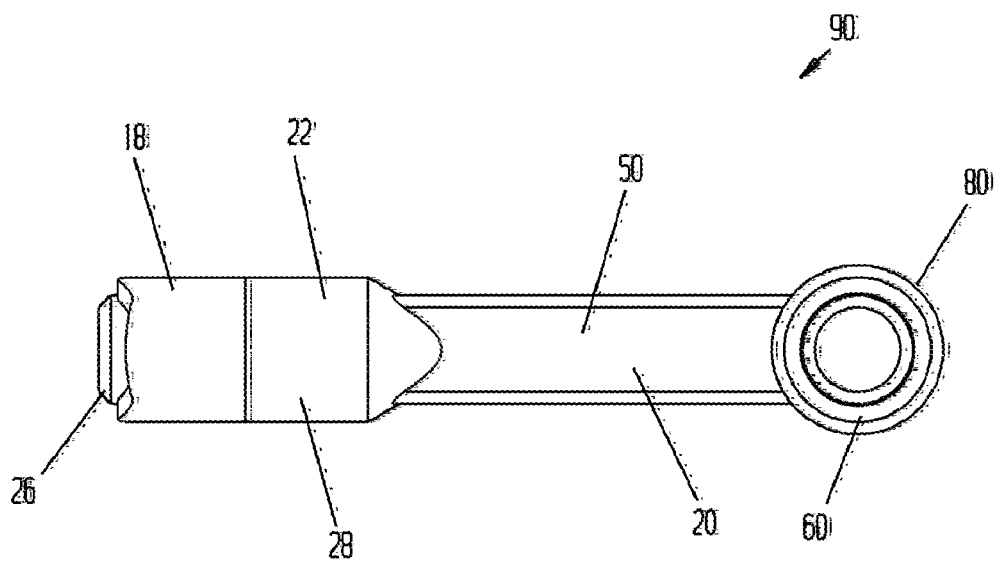
FIG. 12 is a plan view of the tip assembly of the object of FIG. 2 with the dielectric coating removed.
Figure 13:
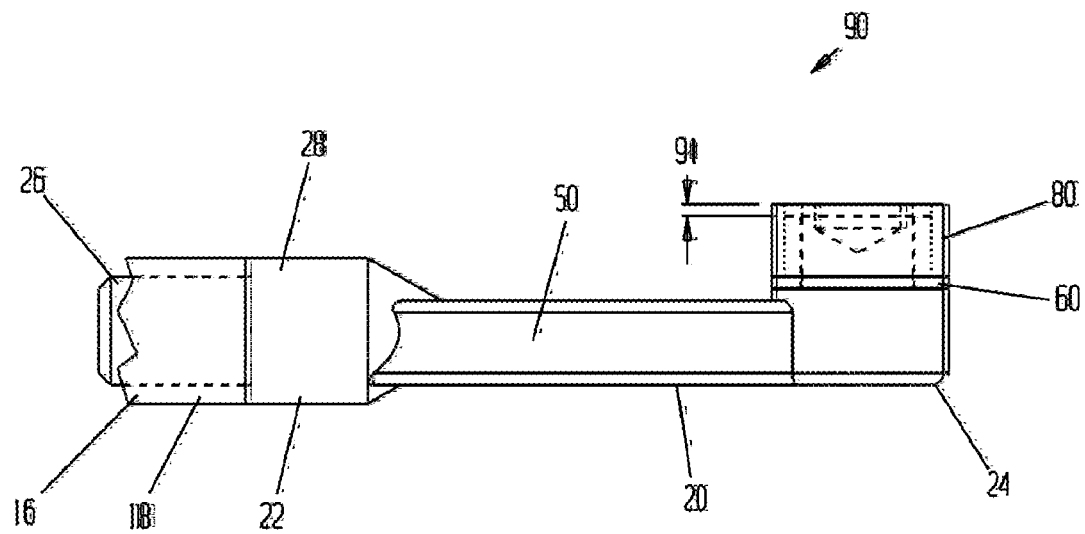
FIG. 13 is a front elevational view of the object of FIG. 12.
Figure 14:
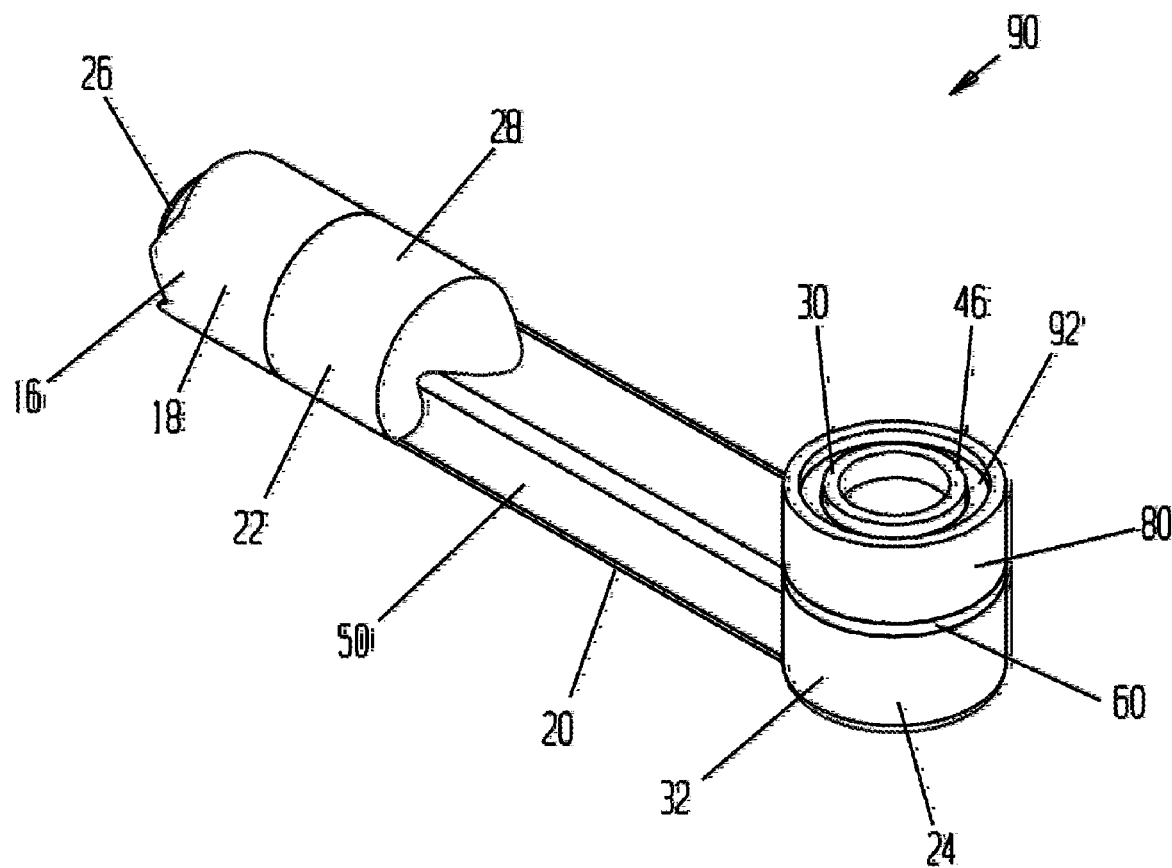
FIG. 14 is a perspective view of the object of FIG. 12.

As seen in FIGS. 12 through 14, distal end subassembly 90 is formed of active electrode 20, insulator 60, and ring electrode 80. Insulator 60 is mounted to active electrode 20 such that upper portion 30 of electrode 20 protrudes through insulator 60 as shown, portion 30 protruding above insulator 60 distance 91. Ring electrode 80 is assembled to mounted insulator 60 such that the top surface of ring electrode 80 is approximately equal in height to active electrode 20 with insulator 80 forming an annular recess 92 between them. Subassembly 90 is assembled to distal tip 18 of tubular portion 16 as shown.

Figure 15:
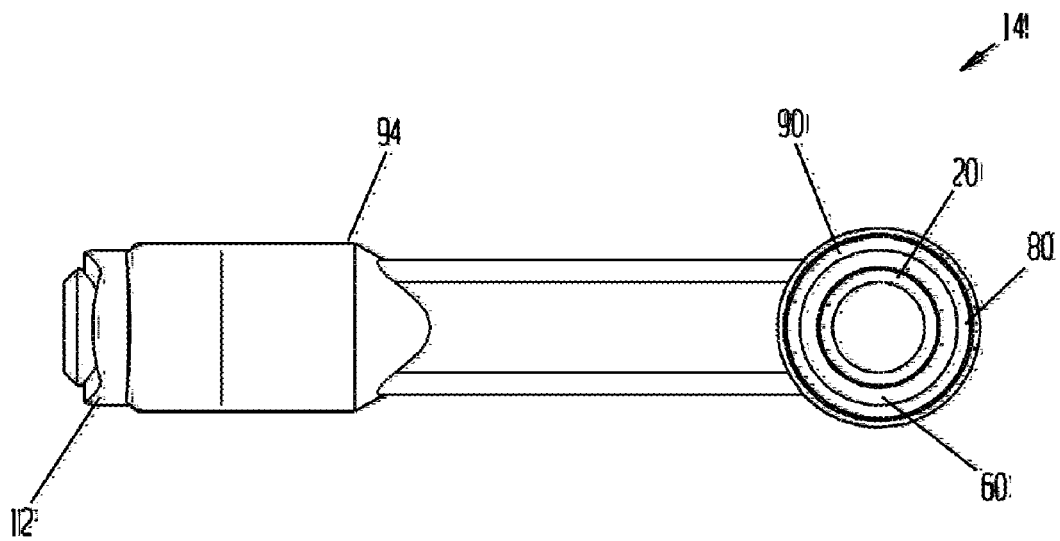
FIG. 15 is an expanded plan view of the distal end of the object of FIG. 1.
Figure 16:
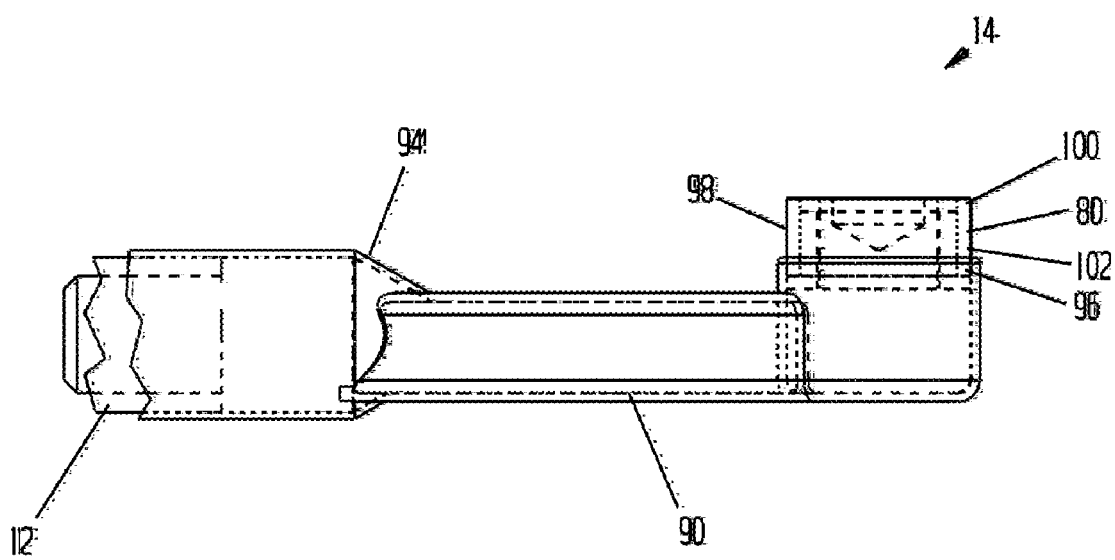
FIG. 16 is a side elevational view of the objects of FIG. 15.
Figure 17:
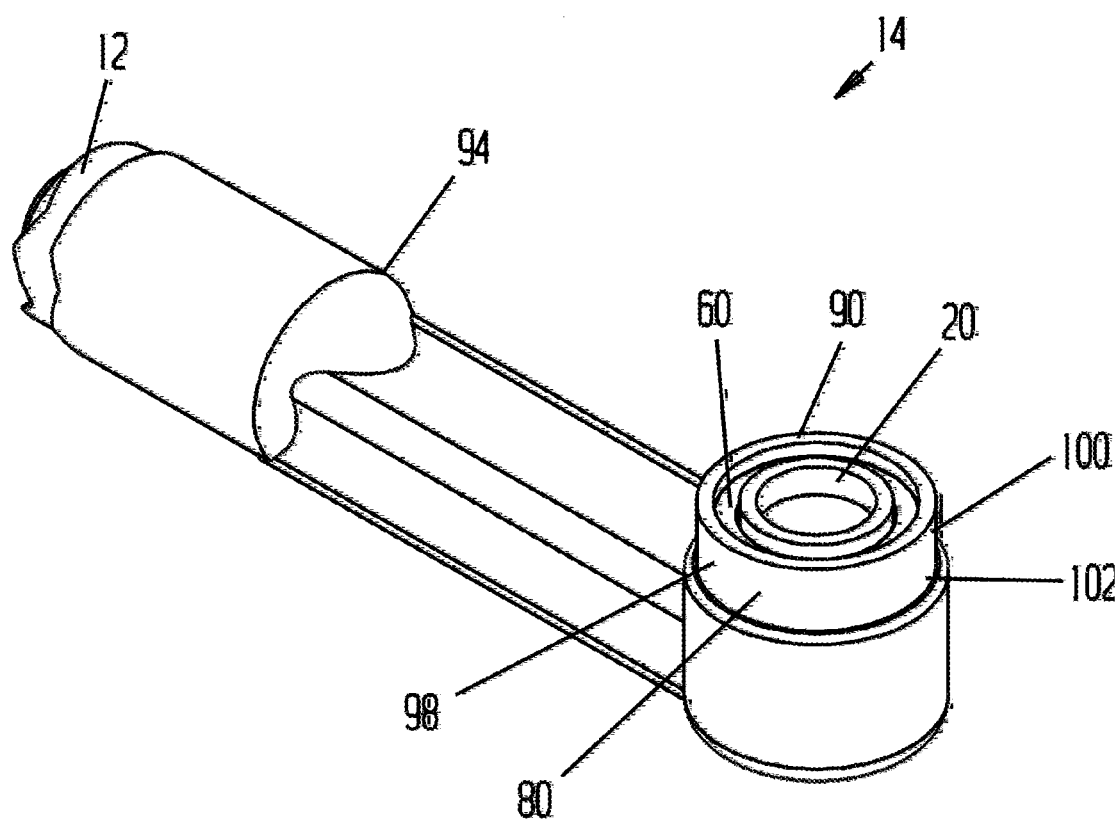
FIG. 17 is a perspective view of the objects of FIG. 15.

Referring now to FIGS. 15 to 17, distal end assembly 14 is formed by subassembly 90 and dielectric coating 94. Coating 94 covers elongated distal portion 12 and subassembly 90 except for the region including most of ring electrode 80, the exposed upper surface of insulator 60, and the portion of active electrode 20 which protrudes from insulator 60. More specifically, coating 94 covers lower end 96 of ring electrode 80 so as to leave an exposed portion 98 having a top end 100 and bottom end 102. Coating 94 is made from a suitable polymeric material which may be applied, for instance, as a powder coat or liquid which is subsequently cured, or as a molded or extruded tube which is shrunk by heat after application. Components of subassembly 90 are held in place by coating 94, although a suitable adhesive cement may also be used.

Figure 18:
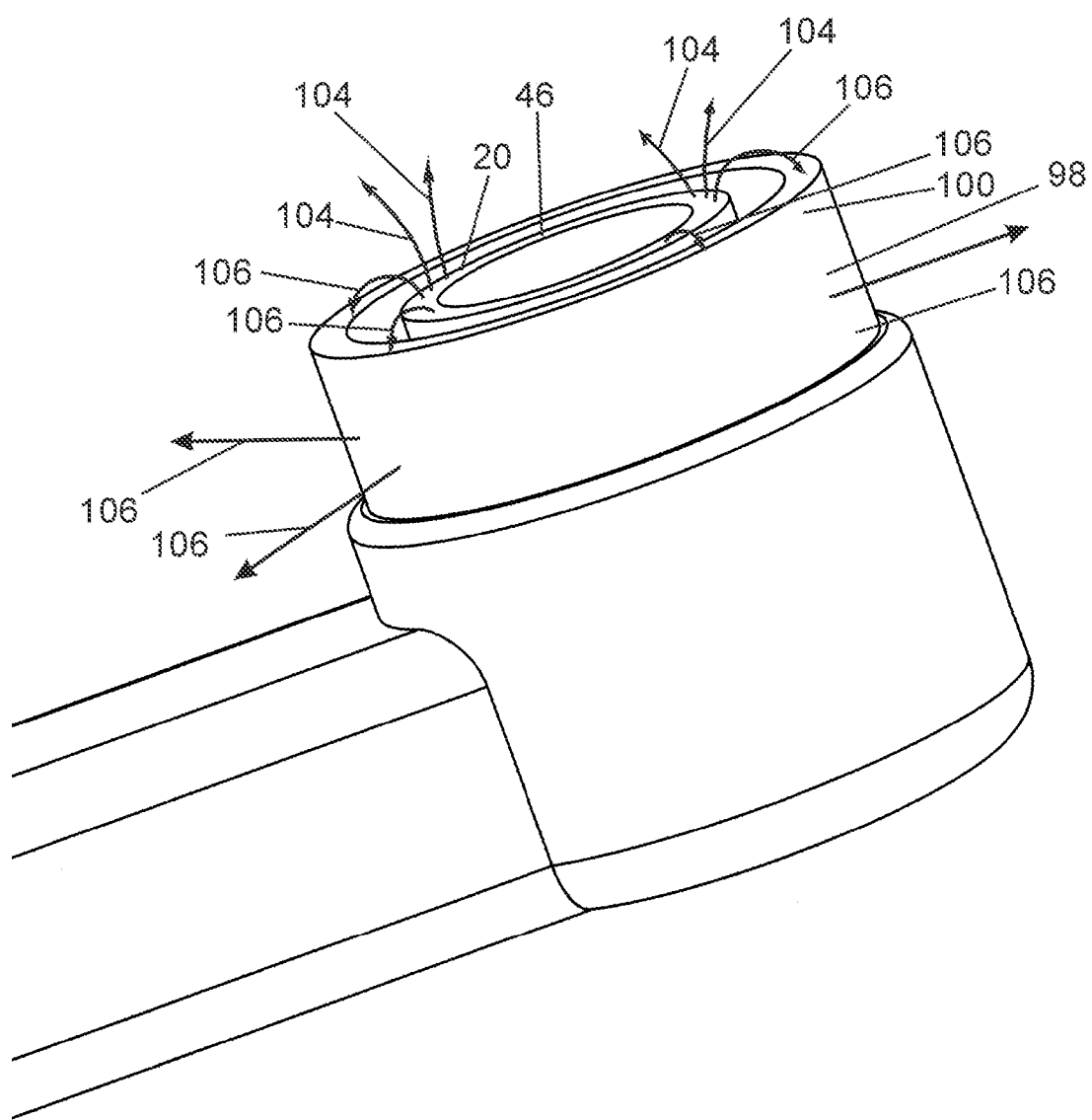
FIG. 18 is an expanded perspective view of the far distal portion of the objects of FIG. 15 schematically showing current flow paths in the region of the active and floating electrodes.
Figure 19:
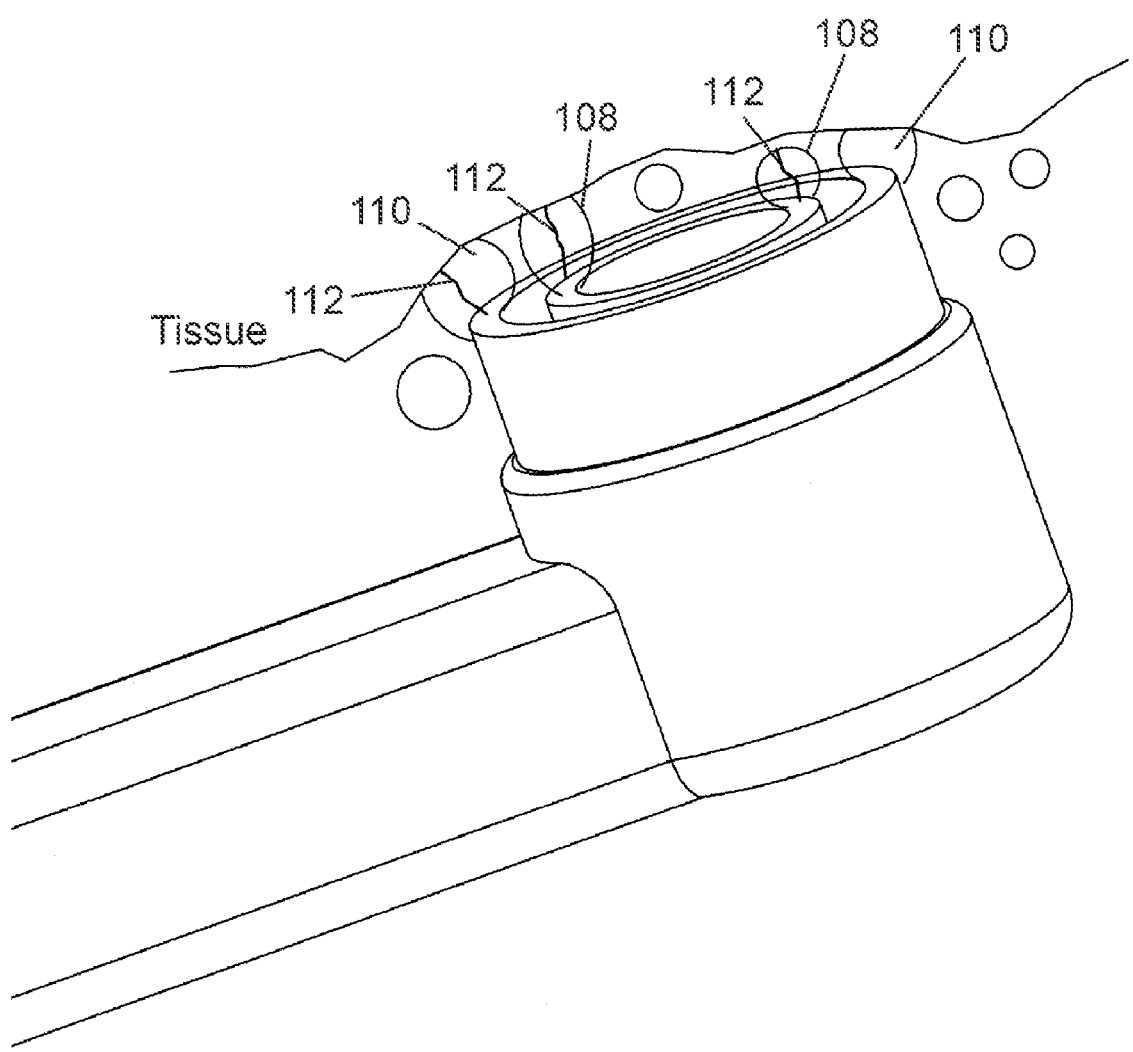
FIG. 19 is an expanded perspective view of the far distal portion of the objects of FIG. 15 schematically showing bubble and arc formation in the region of the active and floating electrodes.

As seen in FIG. 18, during use, distal end 14 of probe 1 is submerged in a conductive liquid. Return electrode 704 is applied to the patient at a site remote to the surgical site. Radio Frequency (RF) energy is supplied to active electrode 20 creating an electric field in the conductive fluid. Top end 100 of exposed portion 98 of ring electrode 80 is in a high-potential region of the electric field. Bottom end 102 of portion 98 of electrode 80 is in a lower potential region of the electric field. Current flows from rim 46 of active electrode 20 into the conductive fluid, the current density being greatest immediately adjacent to the exposed surface of rim 46. Some current 104 flows into the fluid and through the patient's body to the return electrode. Current 106 flows through the conductive liquid to high-potential top end 100 of ring electrode 80, through electrode 80 to lower potential regions of exposed portion 98 near bottom end 102. Current 106 flows from the lower potential regions of electrode via the conductive fluid to the patient's body and return pad 704. Electrical current passing through conductive fluid heats the fluid, making it more conductive, which in turn causes more current to flow through the heated region. Probe 1 shown in FIG. 18 has two regions of high current density, the first at rim 46 of active electrode 20 and the second at top end 100 of ring electrode 80. As seen in FIG. 19, heating of the conductive liquid in these areas causes it to boil forming bubbles 108 on rim 46 of electrode 20 and bubbles 110 on top end 100 of ring electrode 80. Arcs 112 occur within some of these bubbles. When distal end 14 of ablator 1 is brought into contact with, or close proximity to tissue, some of the bubbles intersect the tissue surface and arcs pass from the electrodes, through the bubbles to the tissue, which is ablated (vaporized).

Figure 20:
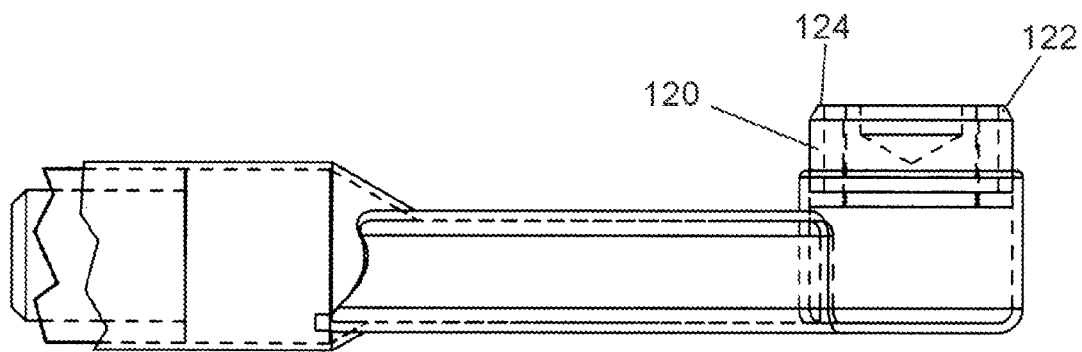
FIG. 20 is a side elevational view of the distal end portion of an alternate embodiment having a chamfered ring electrode.
Figure 21:
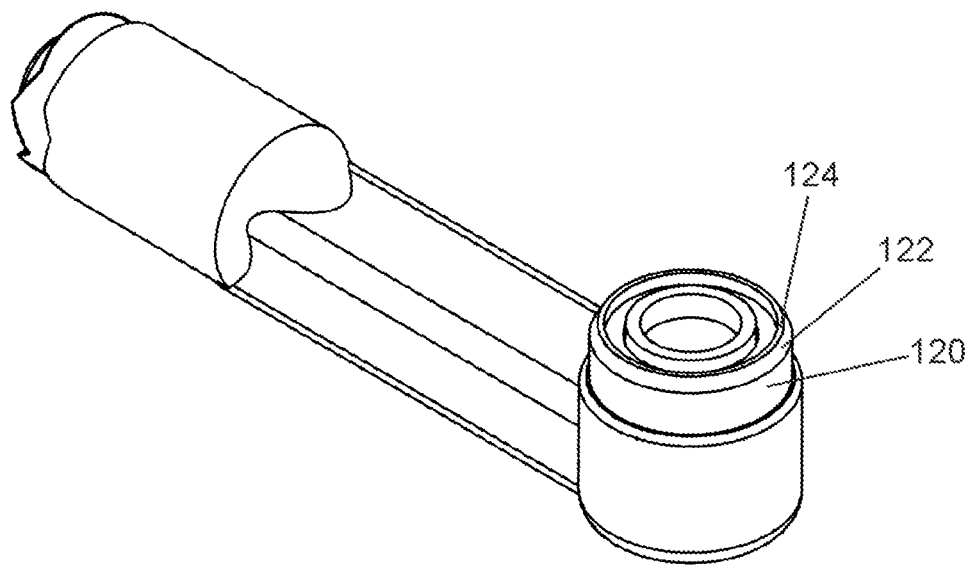
FIG. 21 is a perspective view of the object of FIG. 20.
Figure 22:
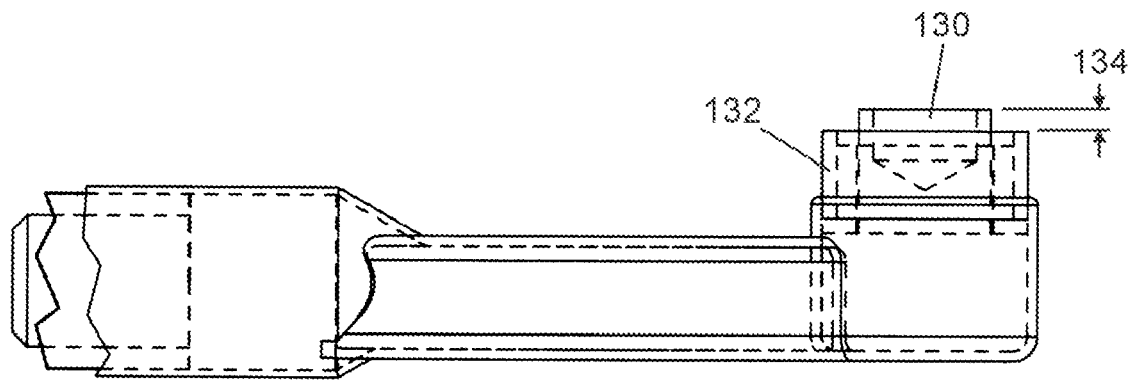
FIG. 22 is a side elevational view of the distal end portion of an alternate embodiment having an extended active electrode.
Figure 23:
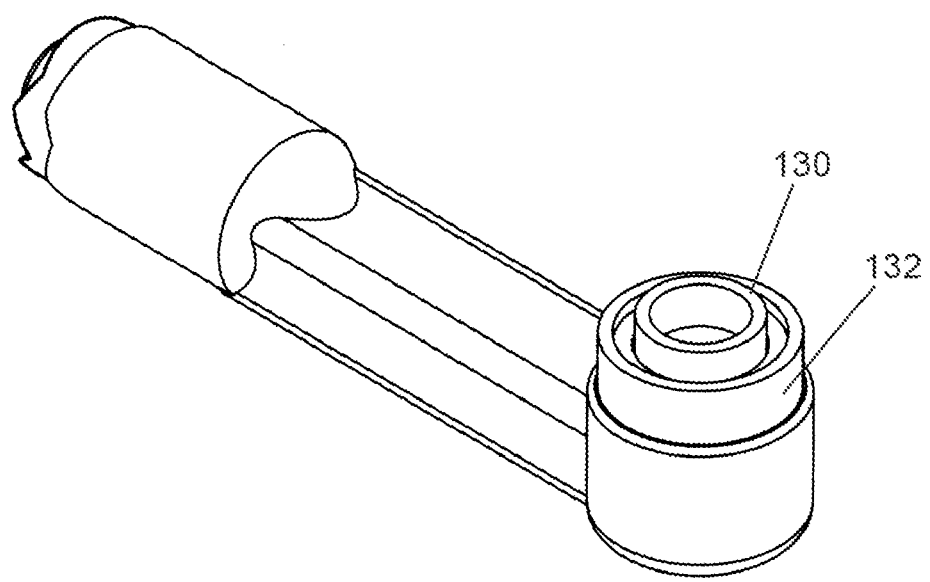
FIG. 23 is a perspective view of the object of FIG. 22.
Figure 24:
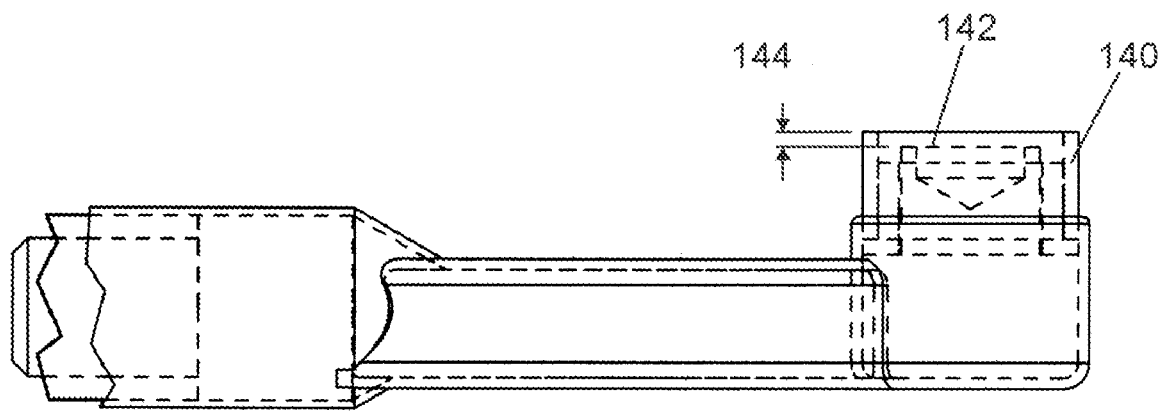
FIG. 24 is a side elevational view of the distal end portion of an alternate embodiment having an extended floating electrode.
Figure 25:
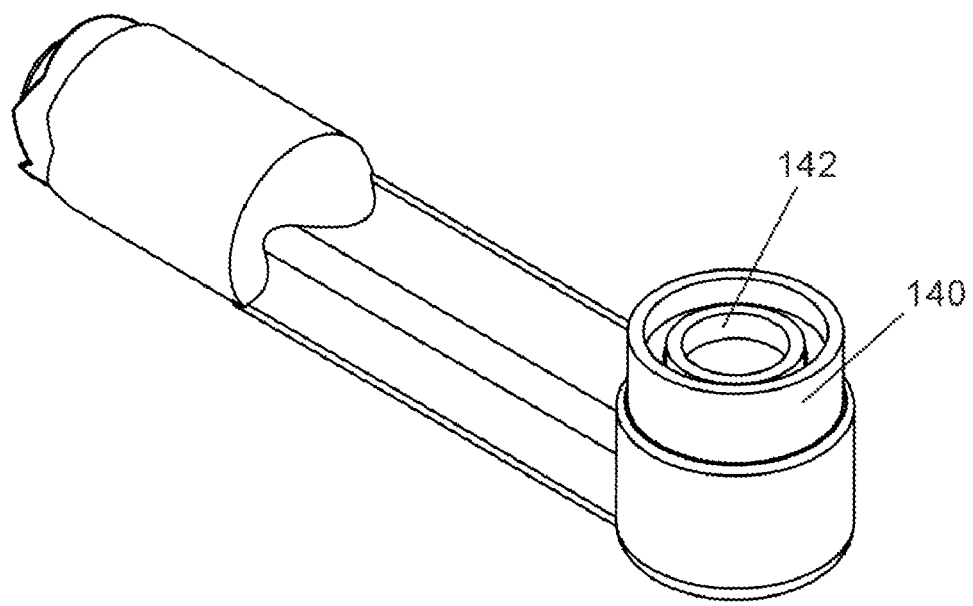
FIG. 25 is a perspective view of the object of FIG. 24.
Figure 26:
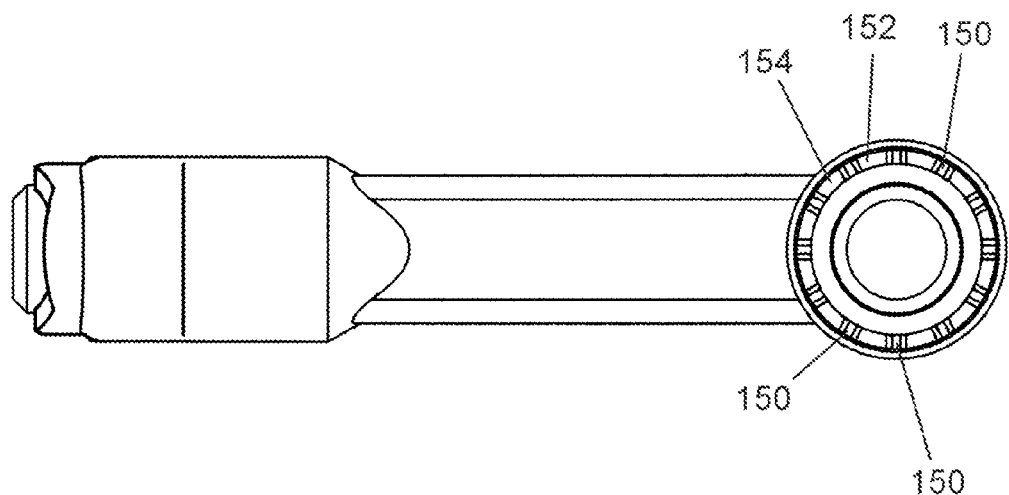
FIG. 26 is a plan view of the distal end portion of an alternate embodiment having slots in the floating electrode.
Figure 27:
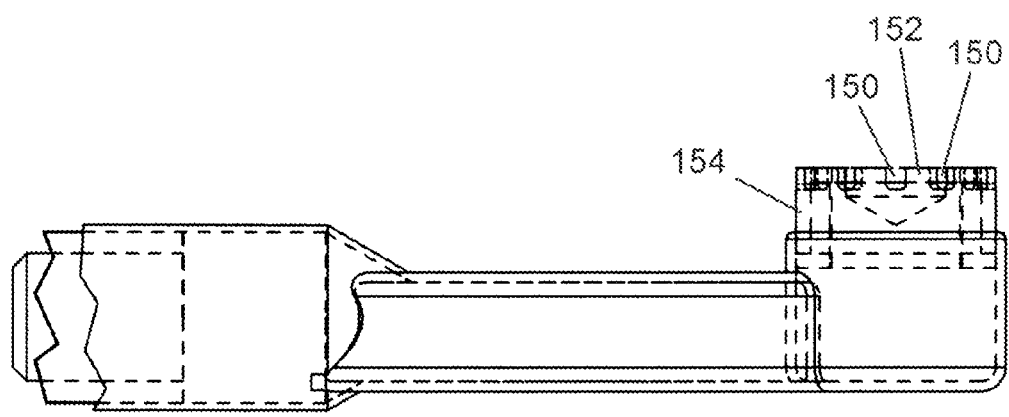
FIG. 27 is a side elevational view of the object of FIG. 26.
Figure 28:
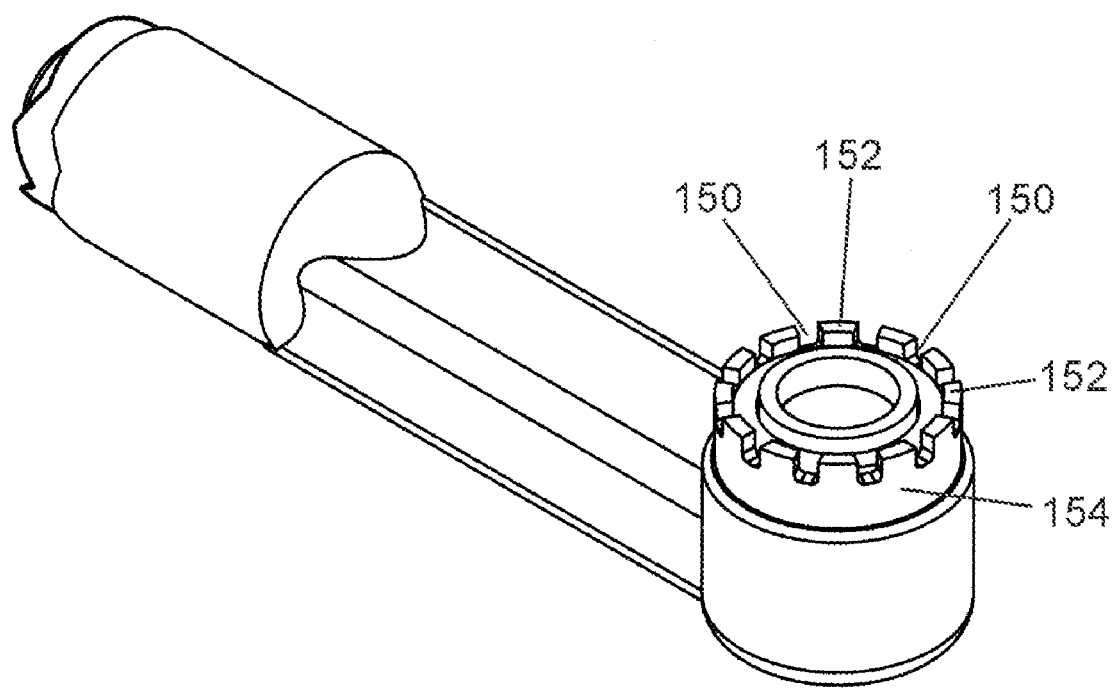
FIG. 28 is a perspective view of the object of FIG. 26.
Figure 29:
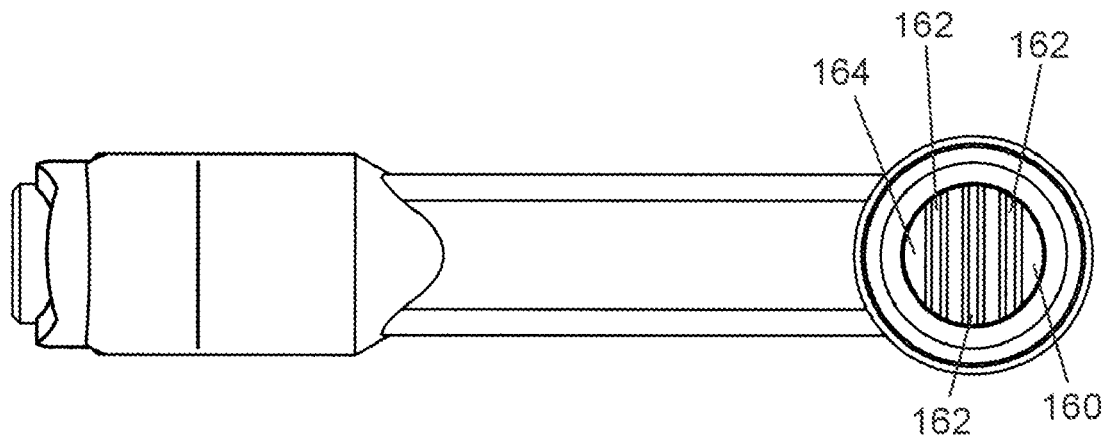
FIG. 29 is a plan view of the distal end portion of an alternate embodiment having a ribbed active electrode.
Figure 30:
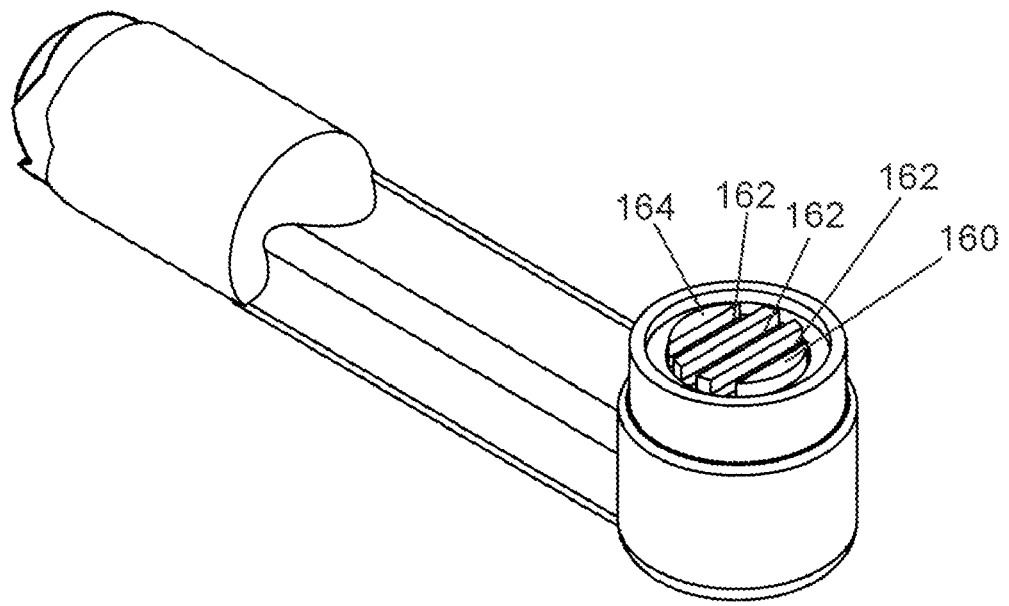
FIG. 30 is a perspective view of the object of FIG. 29.

Numerous modifications may be made to distal tip 14. For instance, FIGS. 20 and 21 show an embodiment in which top end 122 of ring electrode 120 is chamfered so as to form a top surface 124 of reduced area for the purpose of achieving higher current density at the ring electrode. FIGS. 22 and 23 show an embodiment in which active electrode 130 protrudes beyond ring electrode 132 a distance 134. FIGS. 24 and 25 show an embodiment in which ring electrode 140 is protrudes beyond the top end of active electrode 142 a distance 144. FIGS. 26 through 28 show an embodiment in which a plurality of slots 150 are formed in top end 152 of the ring electrode 154. Slots 150 decrease the exposed area at the top of electrode 154 thereby increasing the current density in the region. Slots 150 also produce a plurality of edges which concentrate current so as to increase bubble generation. Similarly, the embodiment shown in FIGS. 29 and 30 has an alternate active electrode configuration having a plurality of slots for the purpose of concentrating current at the edges formed thereon so as to enhance bubble formation. Active electrode 160 has multiple slots 162 formed in top surface 164.

Figure 31:
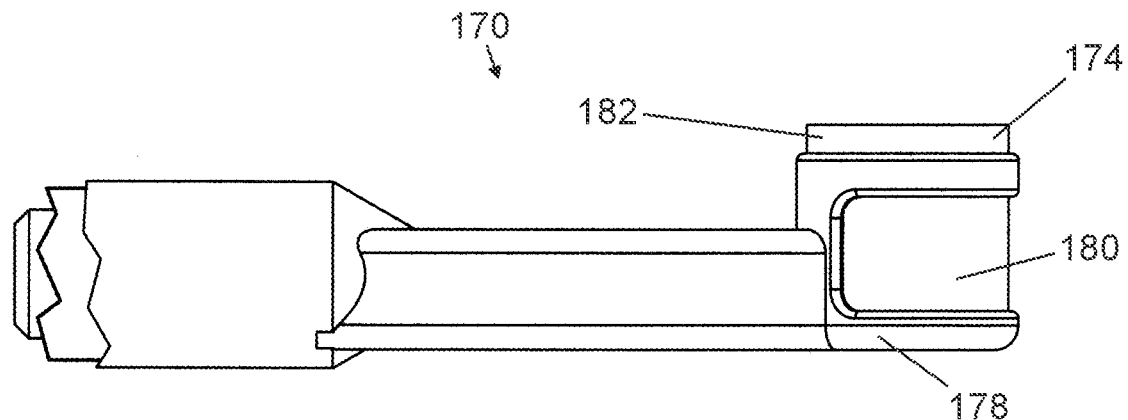
FIG. 31 is a side elevational view of an alternate embodiment having additional exposure of the floating electrode in the low-potential region of the electric field.
Figure 32:
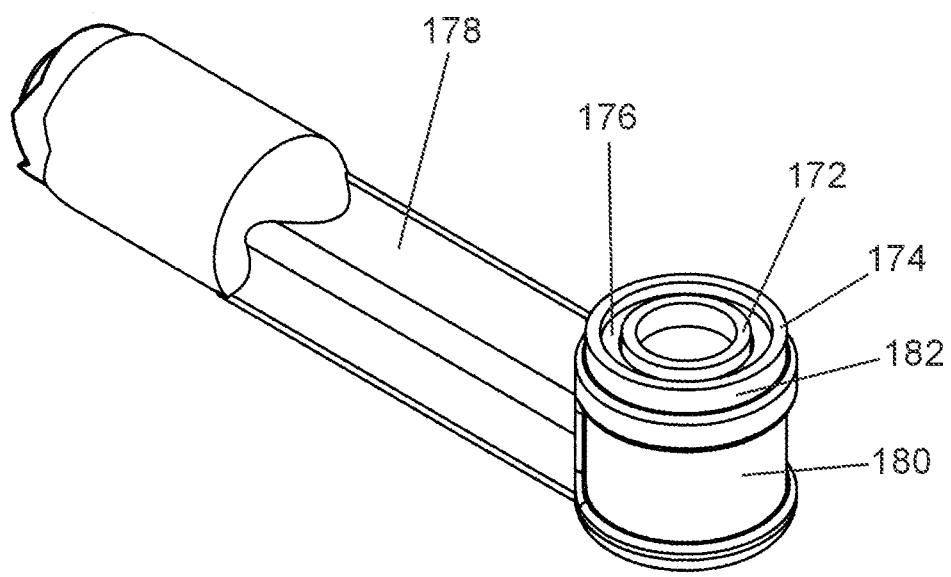
FIG. 32 is a perspective view of the object of FIG. 31.

In another embodiment, the ring electrode is increased in size so as to place a larger area of the electrode in the low potential region of the electric field created by the active electrode. Referring now to FIGS. 31 and 32, distal tip assembly 170 is similar to that of the previous embodiments. That is, an active electrode is separated from a concentric ring electrode by an insulator. The assembly is covered by a dielectric coating except for selected portions of the distal tip. Active electrode 172 is separated from ring electrode 174 by insulator 176. Ring electrode 174 is approximately equal in length to the distal cylindrical portion of active electrode 172. Dielectric coating 178 covers assembly 170 as on the previous embodiments except that a second portion 180 of extended ring electrode 174 is left uncoated. When assembly 170 is submerged in conductive liquid and RF energy is supplied to active electrode 172, upper end 182 of ring electrode 174 is in a high-potential region of the electric field. Portion 180 of ring electrode 174 is in a low-potential region of the electric field. The current path during use is the same as that for the previous embodiments except that current now flows from the larger exposed portion 180 of ring electrode 174 into the conductive liquid for return to the generator via the dispersive pad. The larger exposed area in the low-potential region of the electric field results in higher current densities at the portion of the ring electrode in the high-potential region of the electric with a resulting increase in ablator efficiency.

Figure 33:
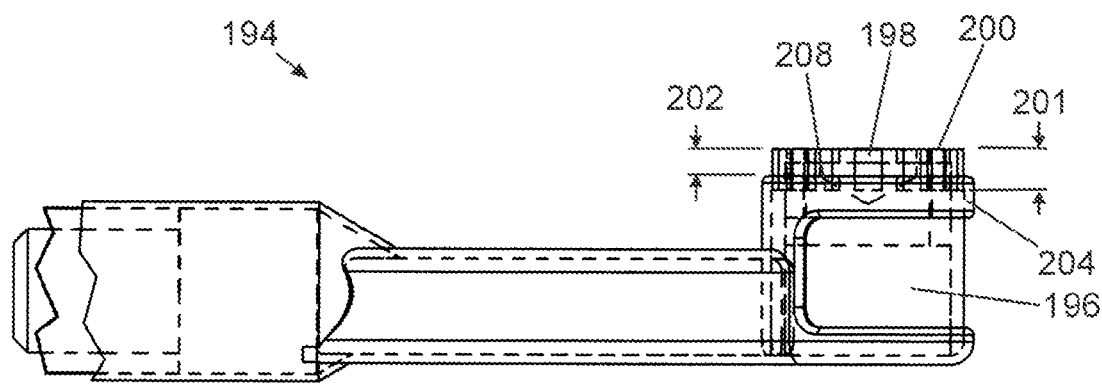
FIG. 33 is a side elevational view of an alternate embodiment similar to the object of FIG. 31 but with radial slots formed in the floating electrode.
Figure 34:
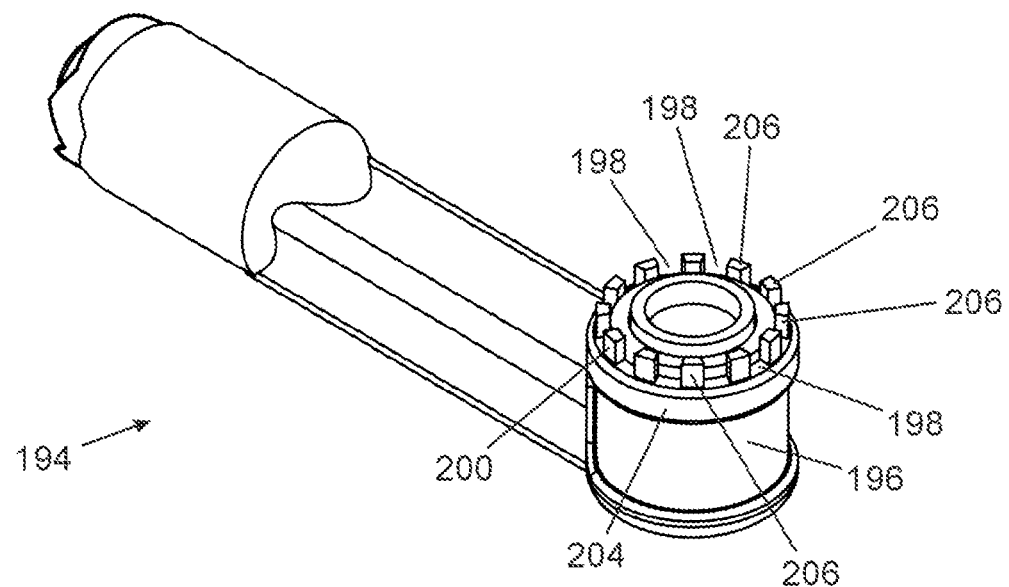
FIG. 34 is a perspective view of the object of FIG. 33.

In another embodiment based on the embodiment of FIGS. 31 and 32, slots are formed in the ring electrode so as to reduce the area of the portion of the electrode in the high-potential region of the electric field so as to increase the current density in that portion. Edges formed by the slots create regions of high current density with further aid bubble formation. Referring to FIGS. 33 and 34, distal assembly 194 is constructed in the same manner as the embodiment of FIGS. 31 and 32 except that top end 200 of ring electrode 196 has a plurality of slots 198 formed therein, the axial depth 201 of the slots being greater than distance 202 that ring electrode protrudes beyond coating 204. Accordingly, top end 200 of ring electrode 196 forms a plurality of protrusions 206 which protrude from the top surface 208 of coating 204.

Other constructions of the distal tip are possible which allow further increase in the size of the portion of the floating electrode which is in the low-potential part of the electric field. An embodiment with such a construction is shown in FIG. 35.

Figure 35:
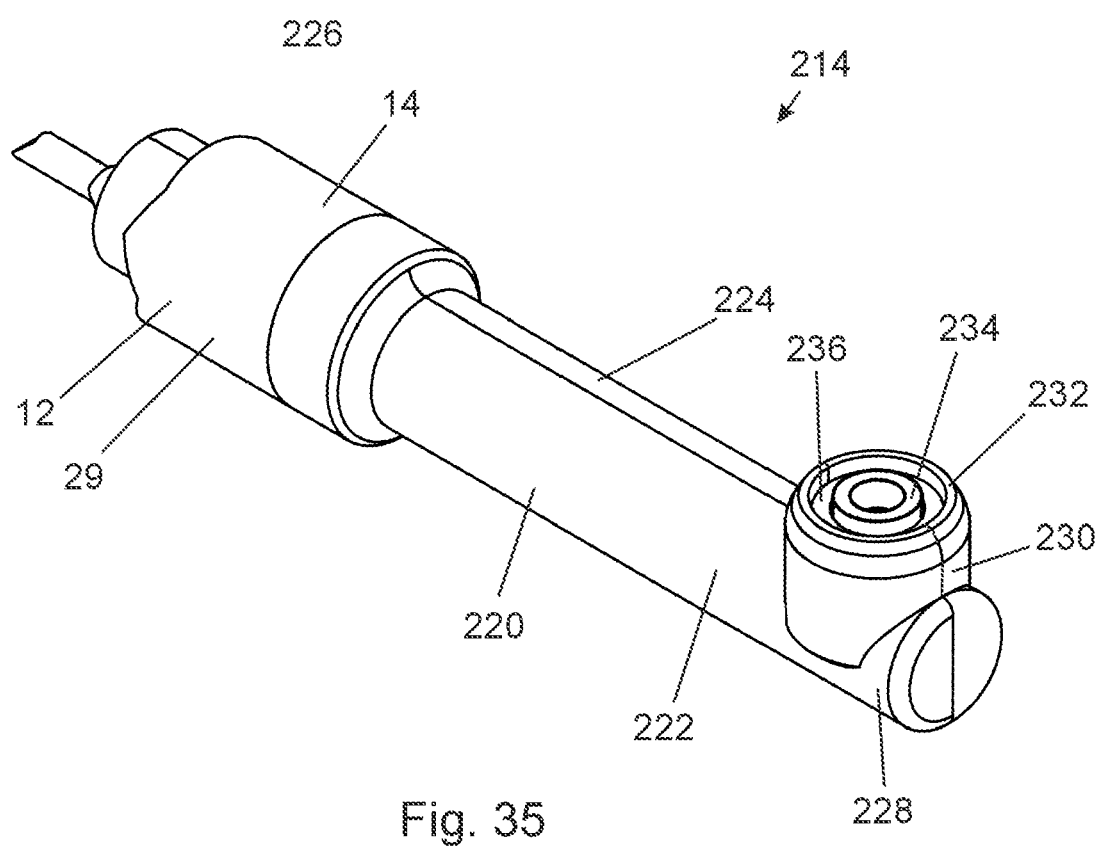
FIG. 35 is a perspective view of an alternate embodiment distal assembly having an increased portion of the floating electrode in the low-potential region of the electric field.

Referring to FIG. 35, assembly 214 attaches to distal end 14 of tubular distal portion 16 (FIG. 1) in the same manner as the previous embodiments and has attached a floating electrode 220 made of an electrically conductive material such as, for instance, stainless steel. Electrode 220 is formed of identical but symmetrically opposite first half 222 and second half 224 joined by, for instance, laser welding. Electrode 220 has a proximal end 226 and a distal end 228, end 226 being pressed into distal end 14 of tubular distal portion 16 of ablator 1. Distal end 228 of electrode 220 forms a cylindrical portion 230 having a rim 232. Centered within portion 230 is active electrode 234 separated from portion 230 by insulator 236.

Figure 36:
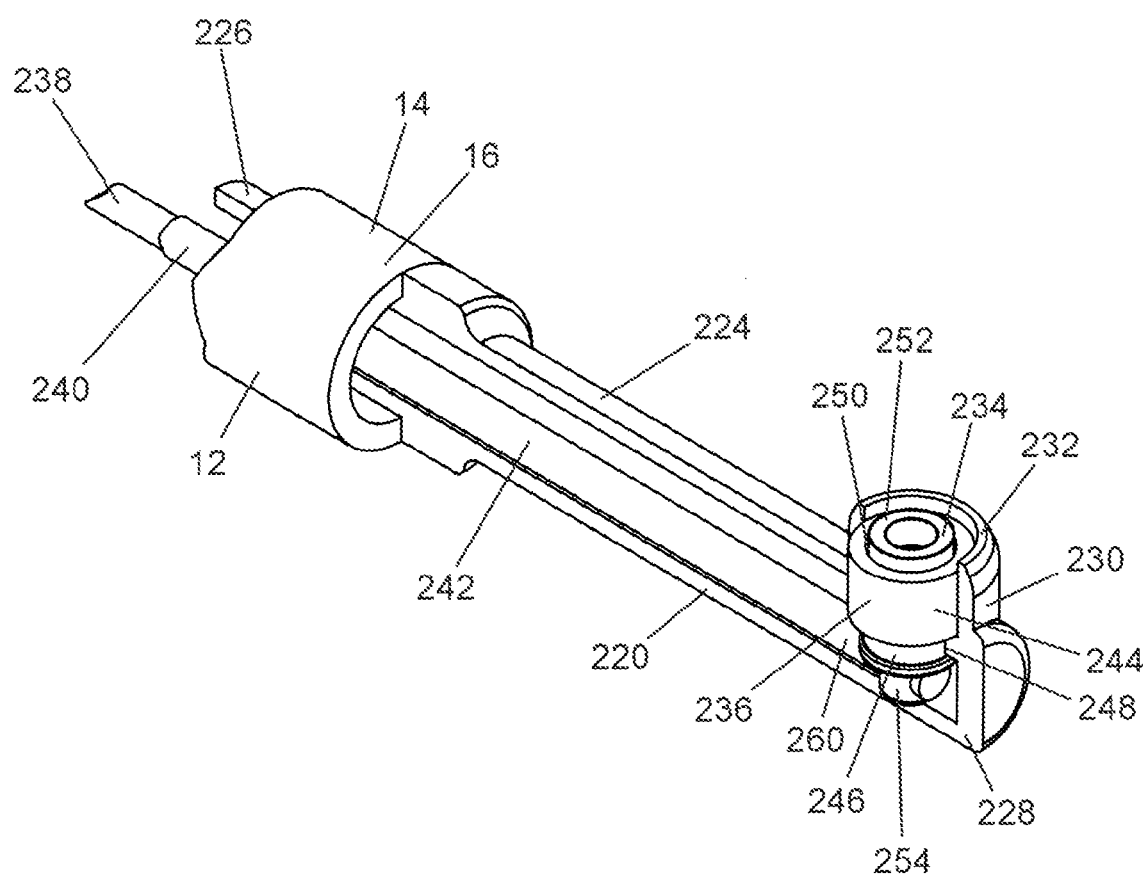
FIG. 36 is a perspective view of the object of FIG. 35 with a first half of the floating electrode removed.

Referring now to FIGS. 36 through 38, active electrode 234, insulator 236, conductor rod 238, and dielectric coating 240 together form an inner assembly 242 located within electrode 220 and electrically isolated therefrom. Insulator 236 has a larger diameter upper portion 244 and a smaller diameter lower portion 246 which locates insulator 236 within cylindrical opening 248 of second electrode half 224. Upper portion 244 has formed therein cylindrical pocket 250. Active electrode 234 has a larger diameter upper portion 252 having a diameter slightly less than the diameter of cylindrical pocket 250 of insulator 236 so that electrode 234 may be mounted therein. Electrode 234 has a smaller diameter lower portion 254 which protrudes through lumen 256 of insulator 236, portion 254 having a lateral cylindrical opening 258 into which is assembled distal end 260 of conductor rod 238. Rod 238, the portion of electrode 234 protruding beyond the bottom end of insulator 236, and the bottom end of insulator 236 are covered by dielectric coating 240. A dielectric coating (not shown) covers elongated distal portion 12 (FIGS. 2 through 4) while leaving a predetermined portion of electrode 220 uninsulated, the portion being optimized so as to maximize the electric field intensity at rim 232.

In the embodiments heretofore described the floating electrode completely surrounds the active electrode. In certain circumstances it may be desirable to intensify the field in only a portion of the probe tip. In these embodiments the floating electrode only partially surrounds the active electrode. In other embodiments two or more floating electrodes are used, the floating electrodes locally intensifying the portion of the field in which they are formed.

Figure 39:
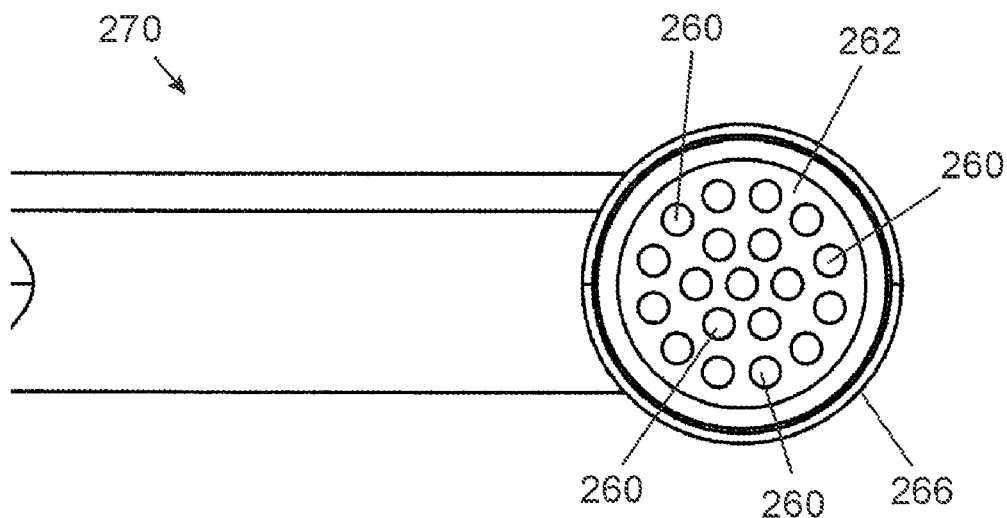
FIG. 39 is a plan view of an alternate embodiment in which the active electrode forms a plurality of protuberances.
Figure 40:
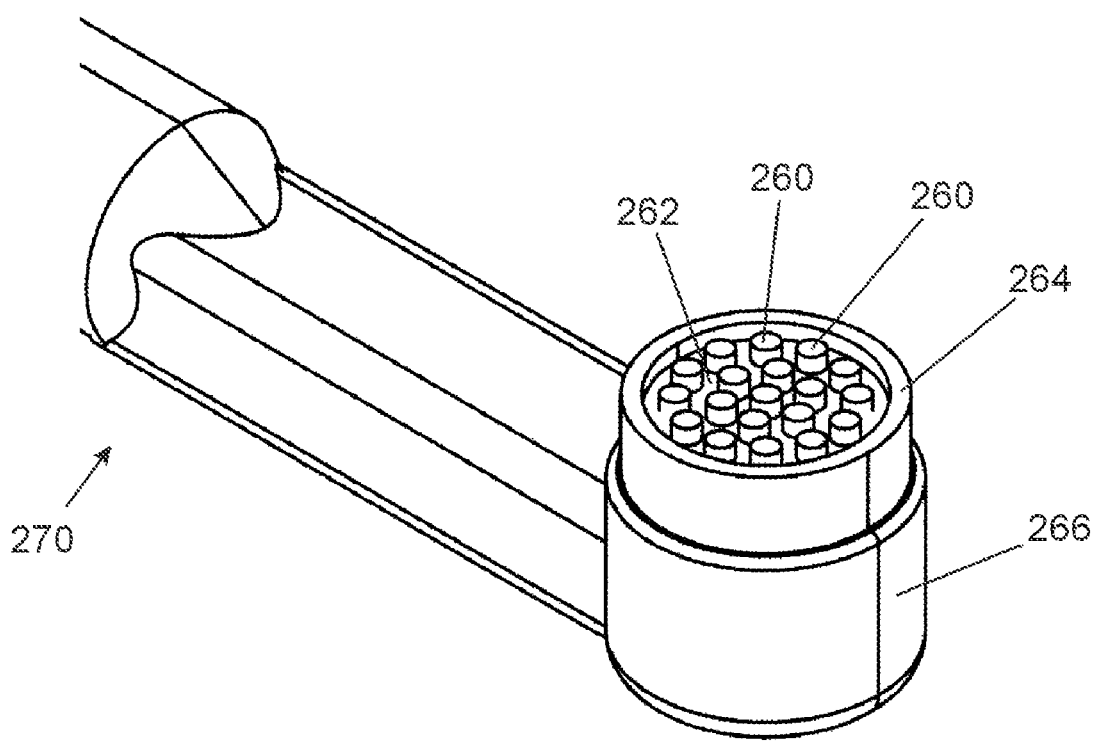
FIG. 40 is a perspective view of the object of FIG. 39.

In another embodiment shown in FIGS. 39 and 40, the active electrode has a plurality of protuberances 260 which protrude from an insulator 262 surrounded by floating electrode 264. Dielectric coating 266 covers tip assembly 270 except for exposed portion 268 of floating electrode 264. FIGS. 39 and 40 show an assembly in which protuberances 260 are all of equal height and are approximately equal in height to floating electrode 264. Protuberances 260 may vary in height. For instance, those toward the center of the array may be of greater height than those at the periphery so as to increase tissue engagement by the center of the probe. Also, some or all of protuberances 260 may be of greater or lesser height than floating electrode 264 to achieve a desired ablative effect.

Figure 41:
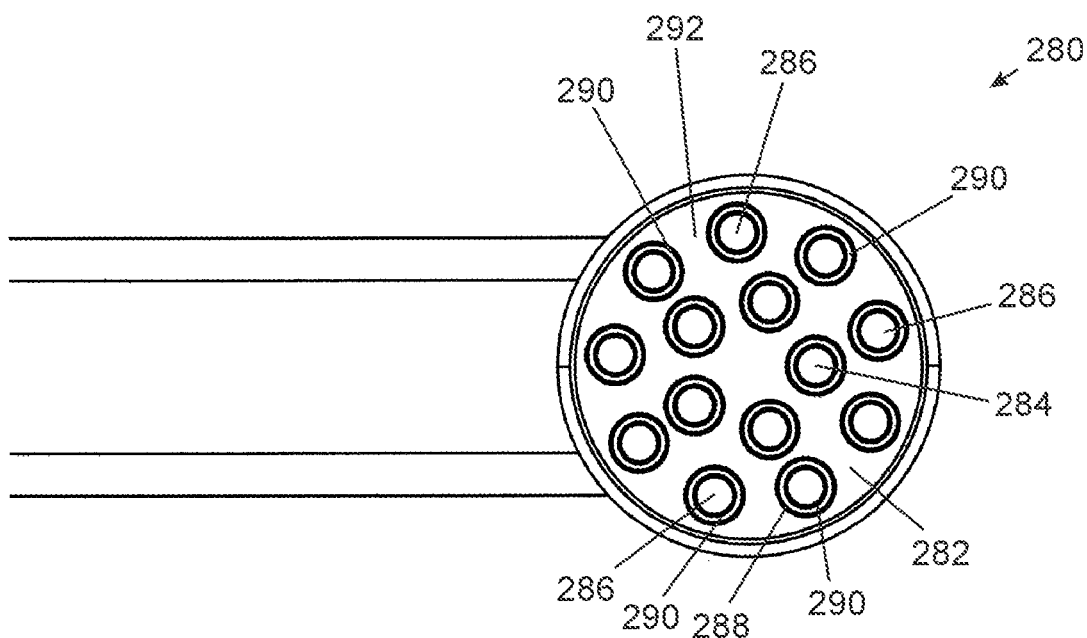
FIG. 41 is a plan view of an alternate embodiment in which the active electrode forms a plurality of protuberances, and the floating electrode is forms a planar surface through which the protuberances protrude.
Figure 42:
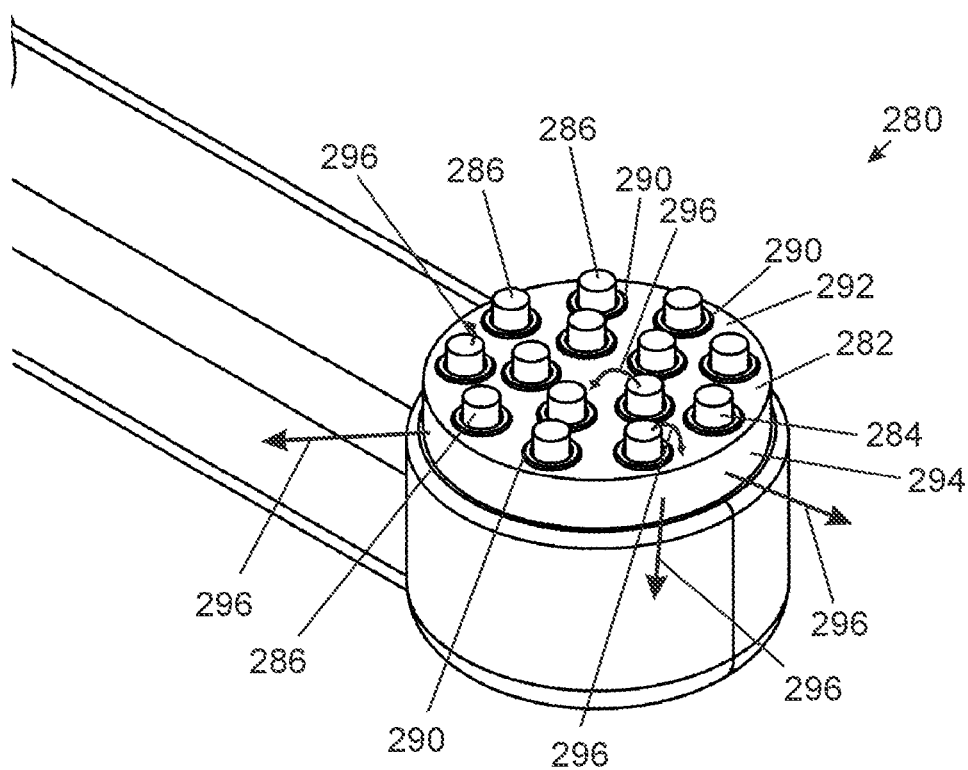
FIG. 42 is a perspective view of the object of FIG. 41.
Figure 43:
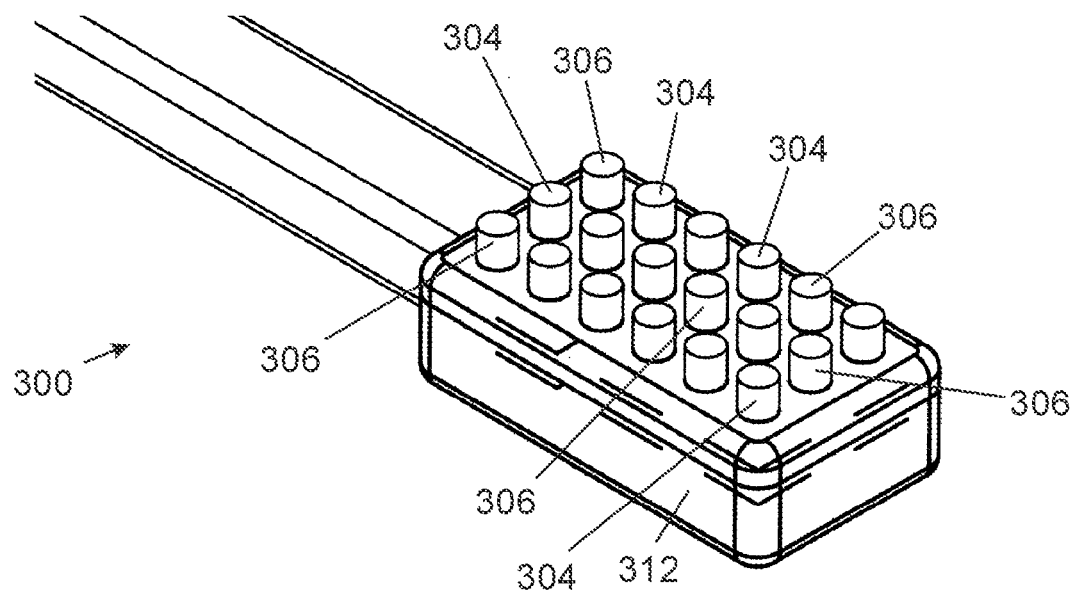
FIG. 43 is a perspective view of an alternate embodiment in which the active and floating electrodes form a plurality of protuberances arranged in a rectangular array.
Figure 44:
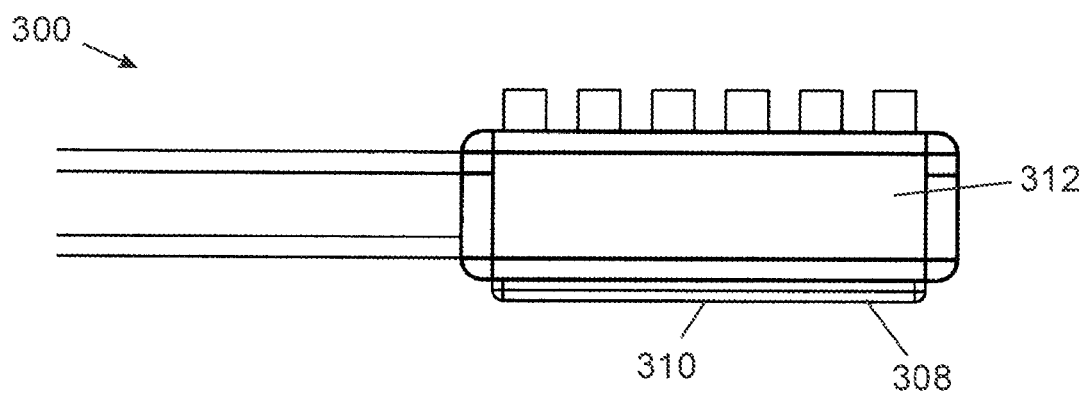
FIG. 44 is a side elevational view of the object of FIG. 43.
Figure 45:
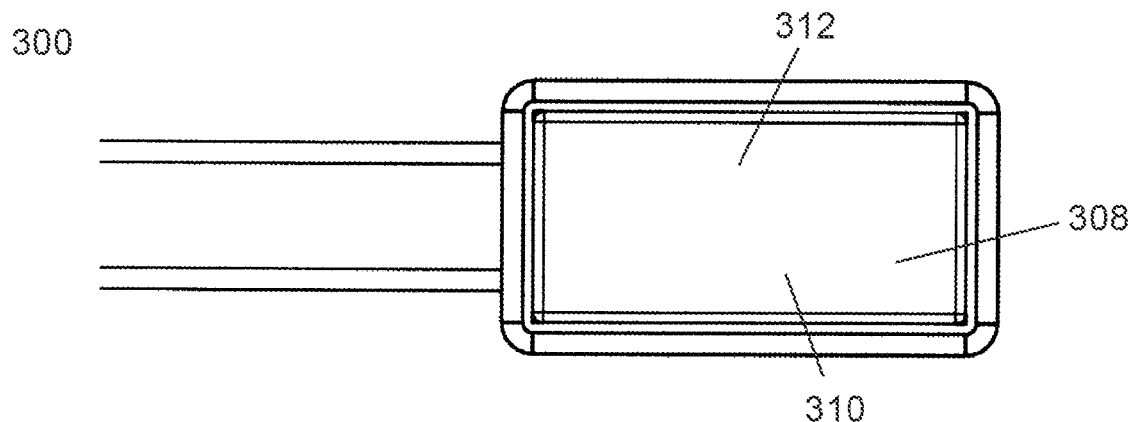
FIG. 45 is a bottom view of the object of FIG. 43.

Another embodiment shown in FIGS. 41 and 42 has a distal tip assembly 280 in which floating electrode 282 is a cylindrical element having a plurality of axial cylindrical holes therethrough. Active electrode 284 has a plurality of protuberances 286 protruding from the axial cylindrical holes in floating electrode 282, and electrically isolated from floating electrode 282 by insulator 288 which has tubular portions 290 surrounding protuberances 286. Current flow 296 is from protuberances 286 through the conductive liquid to axial surface 292 of floating electrode 282 in the high potential portion of the electric field, through floating electrode 282 to portion 294 of electrode 282 which is in a lower potential portion of the electric field, and then through the conductive fluid to the return. In FIGS. 41 and 42, protuberances 286 are of equal height. The protuberances may be of differing heights in order to achieve a given ablative effect, such as, for instance, to have either the peripheral or central portion of the array preferentially engage tissue.

Figure 47:
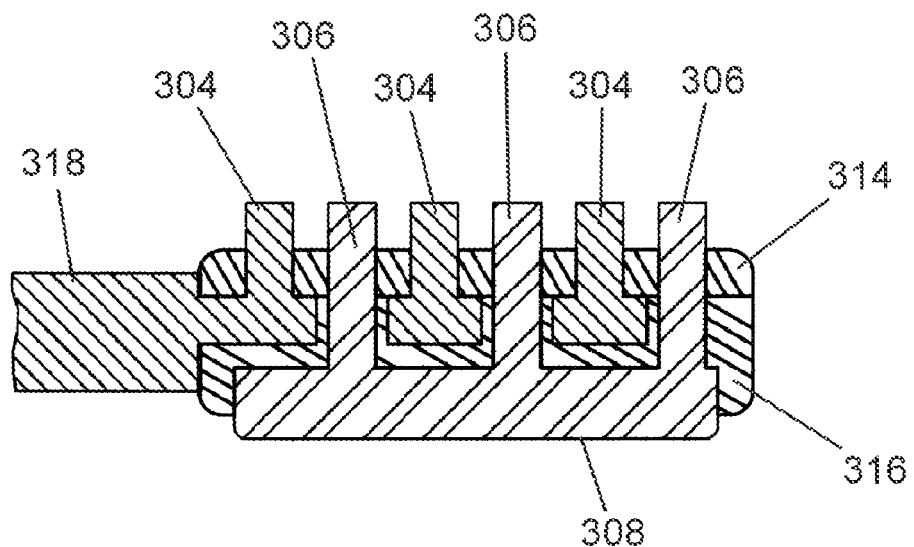
FIG. 47 is a side elevational sectional view of the object of FIG. 43 along the centerline of the object.
Figure 46:
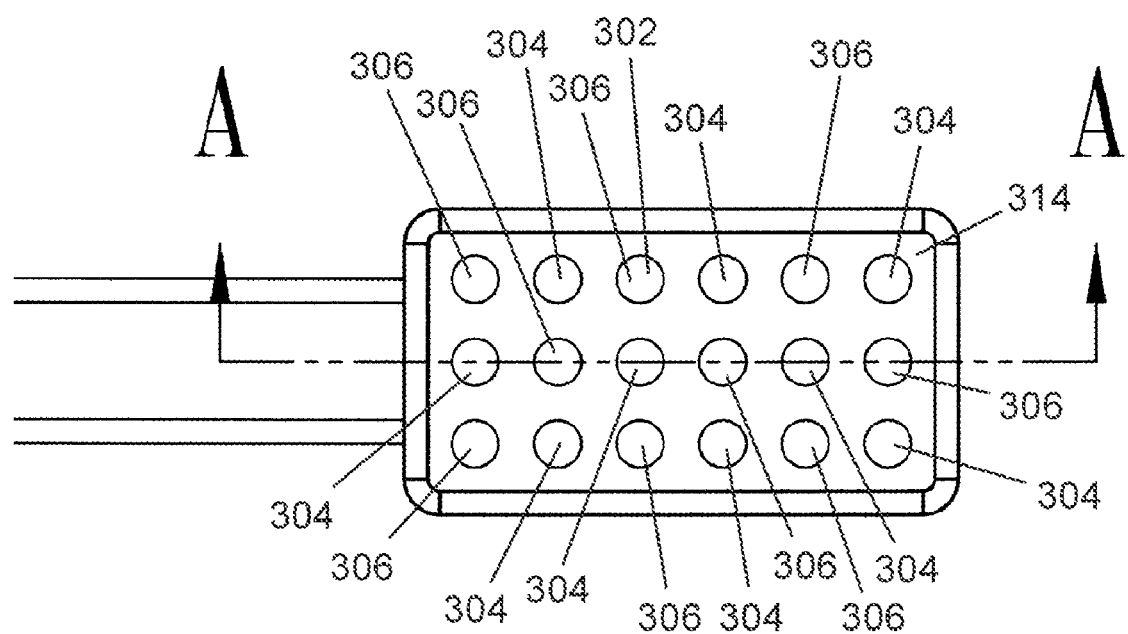
FIG. 46 is a plan view of the object of FIG. 43.

In the embodiments shown in FIGS. 39 through 42, all protuberances are at the same electrical potential, and were surrounded by an annular or planar floating electrode. In another embodiment shown in FIGS. 43 through 47, distal tip assembly 300 has a plurality of protruding pin electrodes 304 and 306. Pins 304 are connected to each other and are connected to the power supply so as to be active electrodes. Pins 306 are floating electrodes connected to plate 308 which forms bottom portion 310 of distal end 312 of assembly 300. As best seen in FIG. 47, insulator top half 314 and bottom half 316 together form an assembly which isolates active electrodes 304 and floating electrodes 306. Dielectric coating 318 covers proximal portion 320 of assembly 300.

Figure 48:
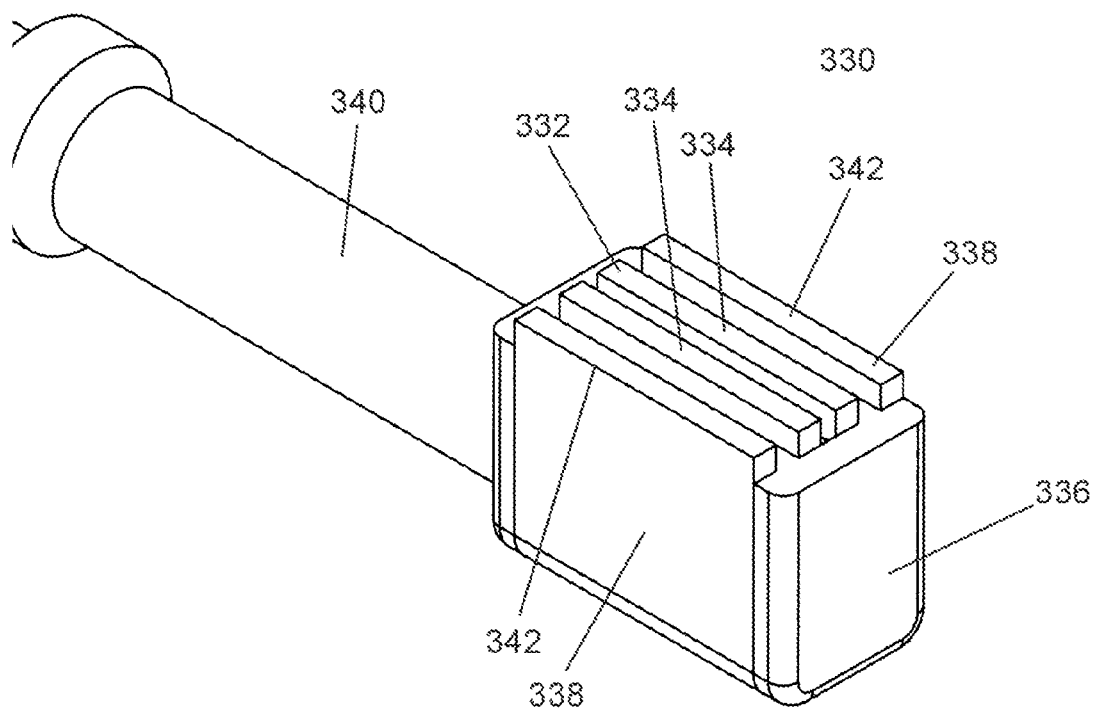
FIG. 48 is a perspective view of an alternate embodiment having elongated active and floating electrodes.

In yet another embodiment shown in FIGS. 48 through 50, distal tip assembly 330 has an active electrode 332 forming a plurality of ribs 334, and a channel-shaped floating electrode 338 separated by insulator 336. Proximal portion 340 of assembly 330 is covered by a dielectric coating. In another embodiment, a portion of floating electrode 338 is coated with a dielectric coating so as to increase current density at the portions of electrode 338 in close proximity to active electrode 332. Upper ends 342 of electrode 338 may be chamfered to decrease the widths of ends 342 to locally increase the current density.

During electrosurgery in a liquid filled space, tissue is vaporized producing steam bubbles which may obscure the view of the surgeon or displace saline from the region of the fluid filled space which the surgeon wishes to affect. In the case of ablation (vaporization), the volume of bubbles produced is even greater than when using other electrodes since fluid is continually boiling at the active electrode during use. Ideally, flow through the joint carries these bubbles away, however, in certain procedures this flow is frequently insufficient to remove all of the bubbles. In such cases it is desirable for the electrode to have an aspiration means which removes some bubbles as they are formed by the ablation process, and others after they have collected in pockets within the joint. An ablator probe with aspiration generally has at least one port located at the probe distal end which is connected via a lumen to an external vacuum source which provides suction for bubble evacuation.

Figure 51:
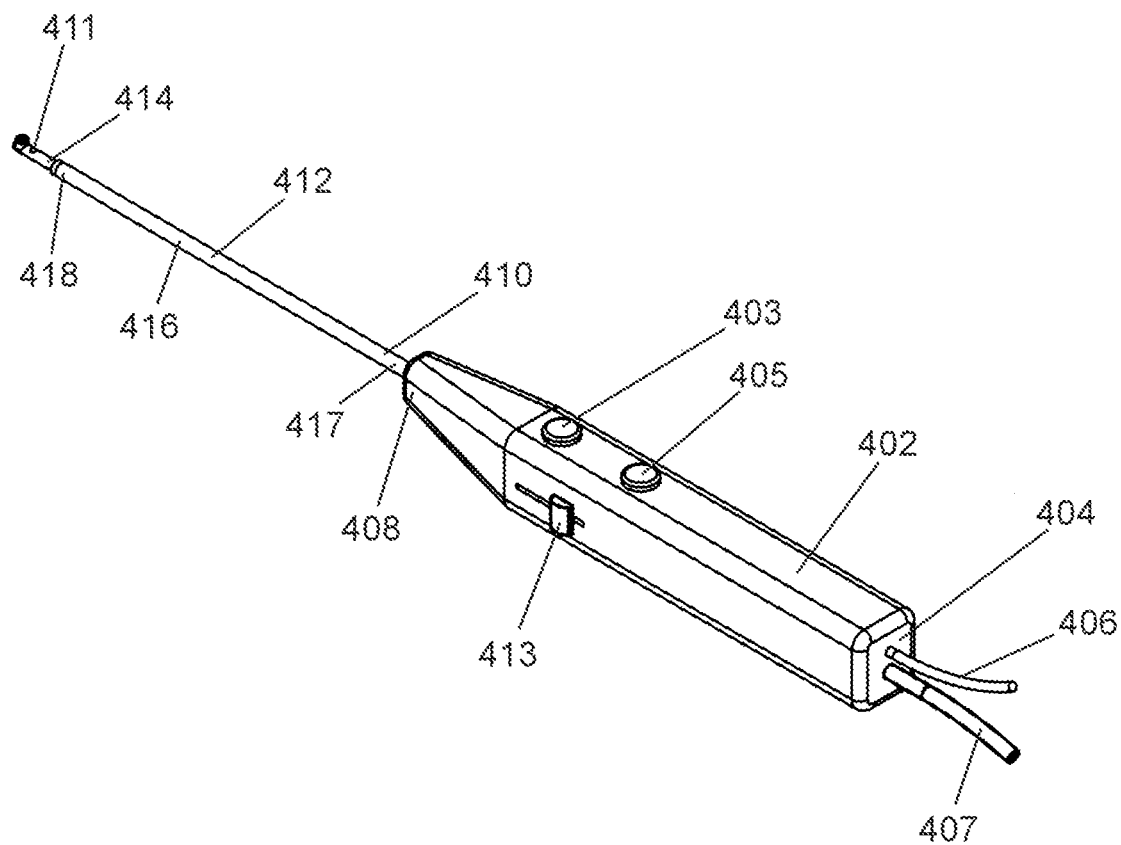
FIG. 51 is a perspective view of an alternate embodiment with aspiration.

FIGS. 51 through 54 show an embodiment of the current invention having a means for aspiration, and a means for controlling the aspiration flow. As seen in FIG. 51, electrosurgical probe 400 has a proximal portion 402 forming a handle and having a proximal end 404 from which passes electrical cord 406 and tube 407, and a distal end 408 which attaches to proximal end 410 of elongated distal portion 412. Distal portion 412 has a distal end 414 and a tubular portion 416. Tubular portion 416 has a proximal end 417 and a distal end 418. Distal end 414 of distal portion 412 has located therein aspiration port 411 in communication with tube 407 via a flow path formed by a lumen within tubular portion 416, and a flow conduction means within proximal portion 402. Slide 413 controls aspiration flow through probe 400. Buttons 403 and 405 control the RF power applied to probe 400.

Figure 52:
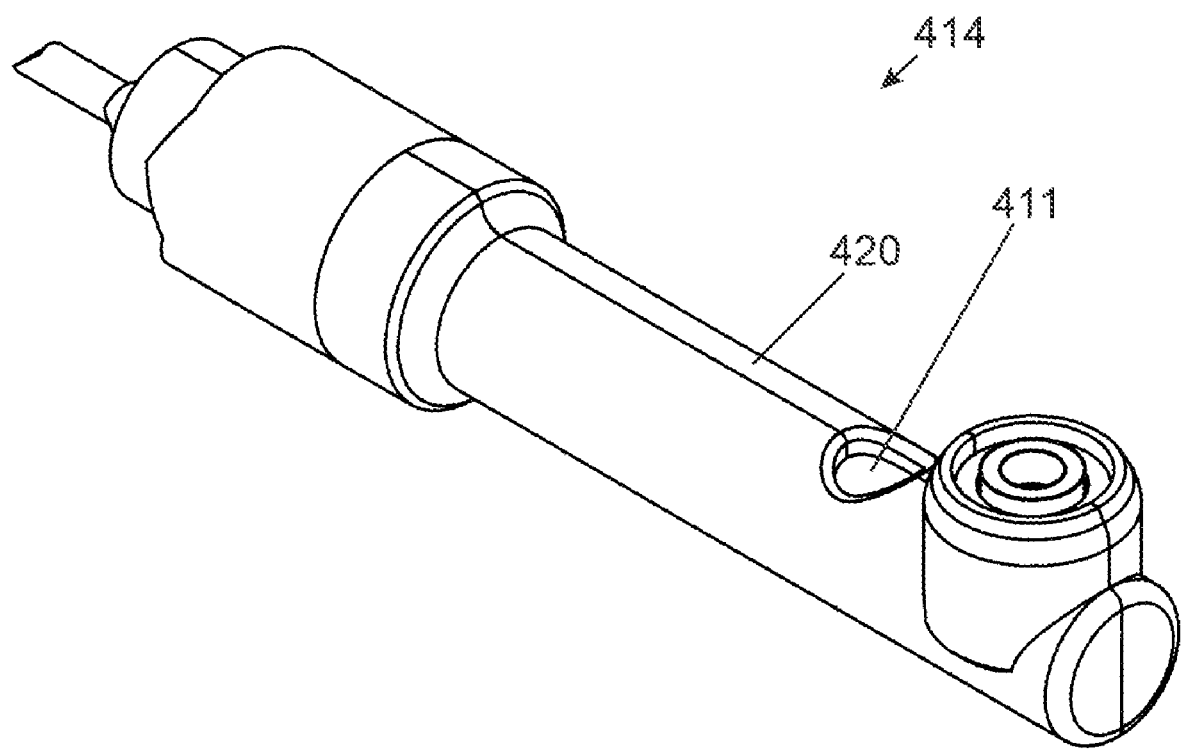
FIG. 52 is an expanded perspective view of the distal end of the object of FIG. 51.
Figure 53:
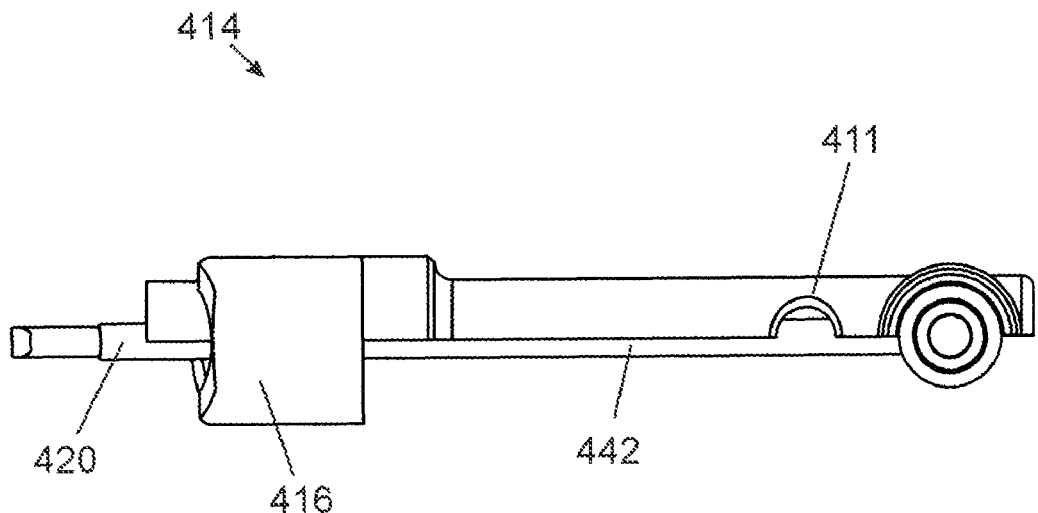
FIG. 53 is a plan view of the object of FIG. 51 with a first half removed.
Figure 54:
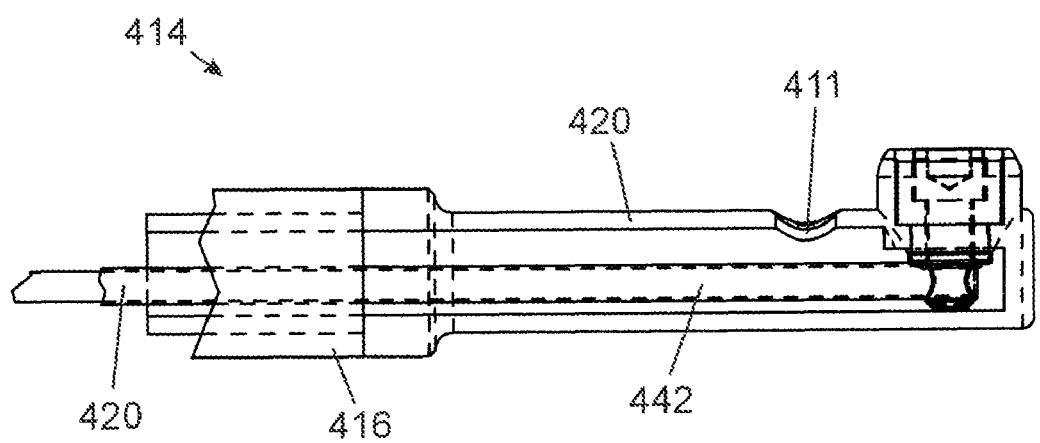
FIG. 54 is a side elevational view of the object of FIG. 53 showing the aspiration path.

Referring now to FIGS. 52 through 54, distal end assembly 414 of ablator 400 is identical in construction to assembly 214 of the ablator embodiment shown in FIGS. 35 through 38. Accordingly, only those features unique to the aspiration assembly 414 of ablator 400 will be described. As best seen in FIG. 52, electrode 420 of assembly 414 has in its top surface, proximal to the active electrode, aspiration port 411. As best seen in FIGS. 53 and 54, aspiration port 411 is in communication with an aspiration passage formed by the inner portion of electrode 420 and the lumen of tubular portion 416. Inner assembly 442 is electrically isolated by dielectric coating 420 from fluid and materials flowing through the passage.

During use, suction supplied by an external vacuum source via tube 407 to probe 400 evacuates fluid, bubbles and debris from the surgery site, the rate of flow being controlled by slide 413.

Figure 55:
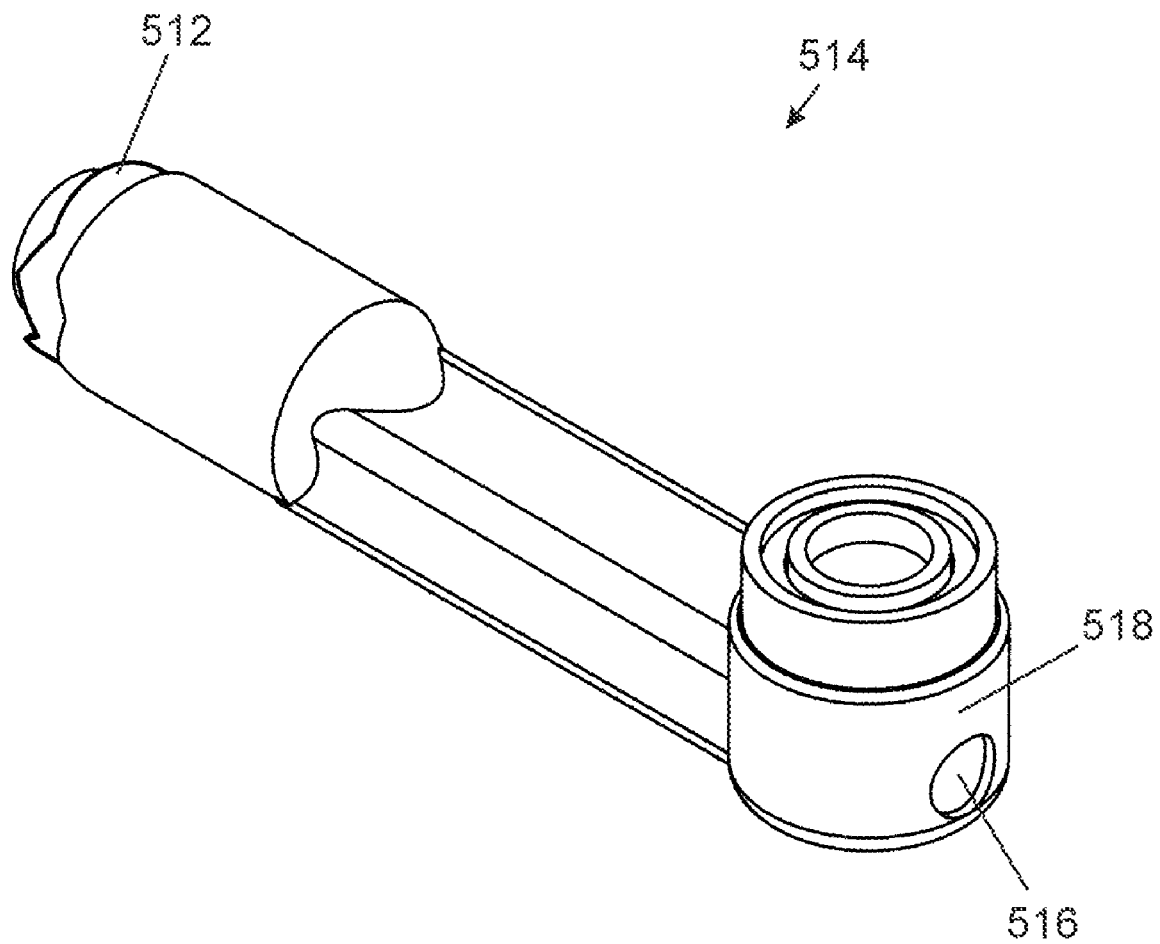
FIG. 55 is an expanded view of the distal end of an alternate embodiment with aspiration.
Figure 56:
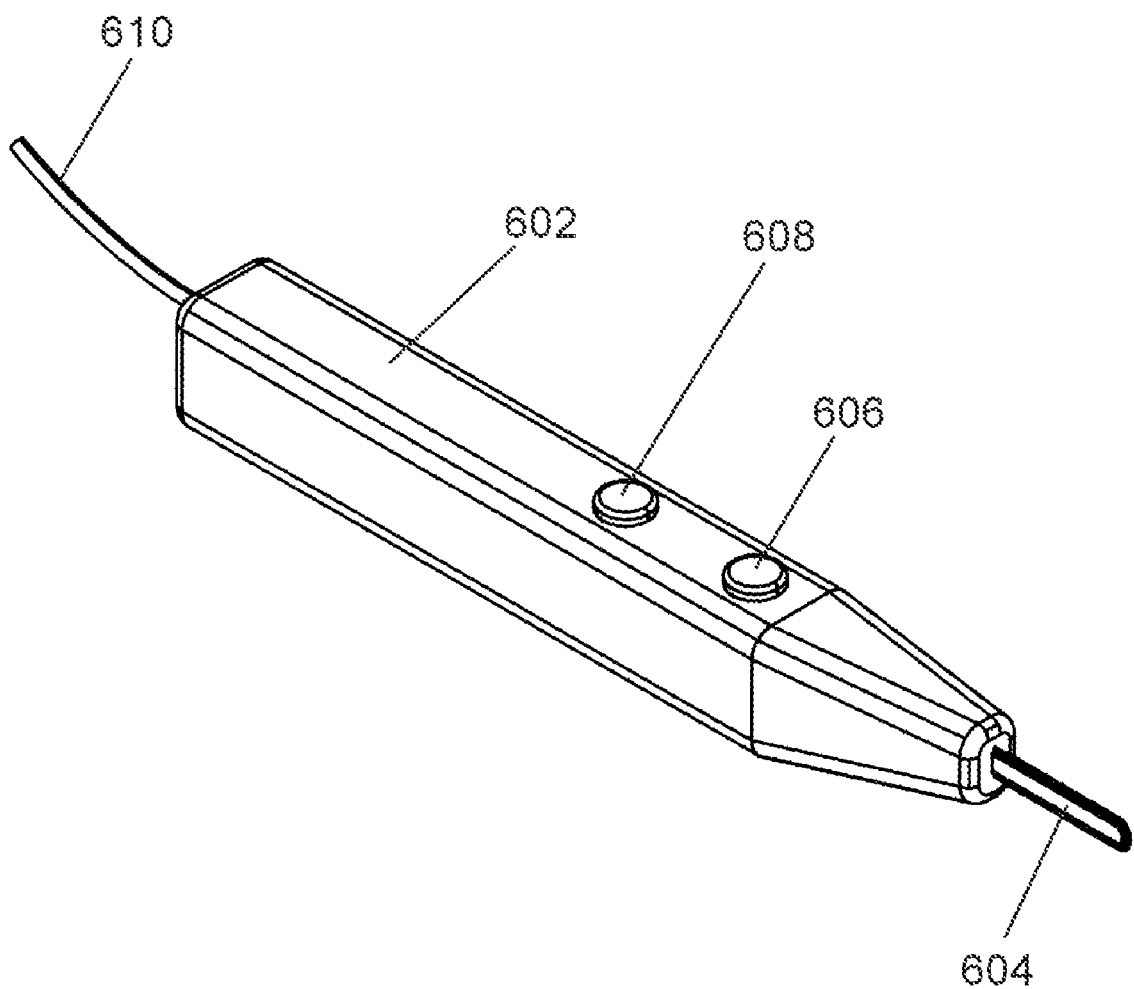
FIG. 56 is a perspective view of an alternate embodiment with an electrode assembly formed to a blade shape.
Figure 57:
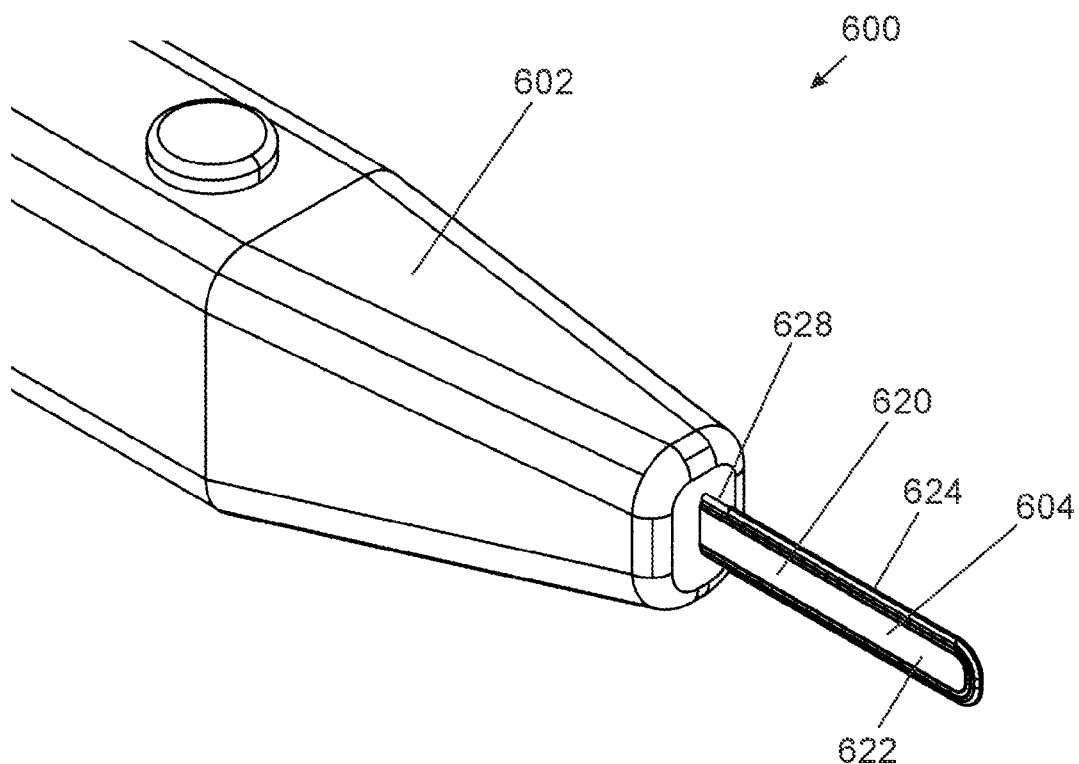
FIG. 57 is an expanded perspective view of the distal end of the object of FIG. 56.
Figure 58:
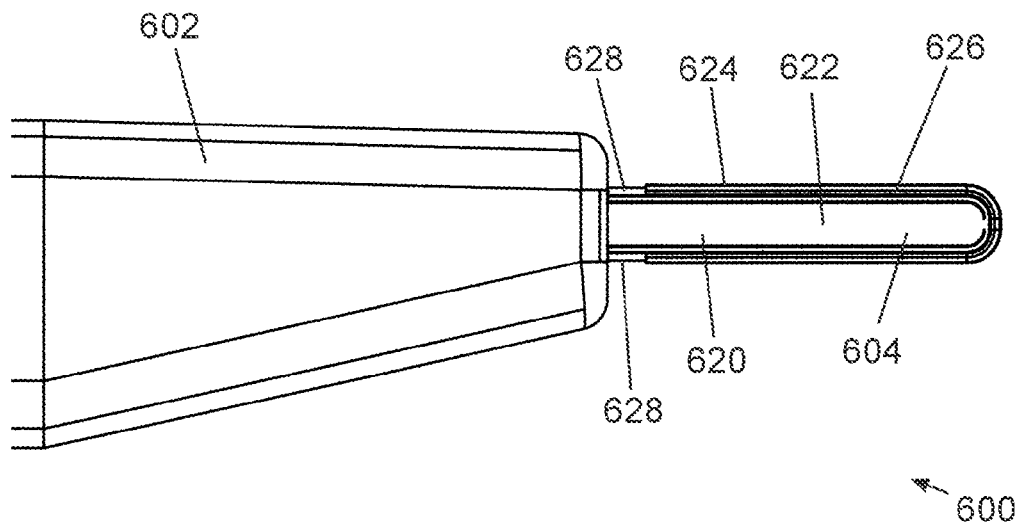
FIG. 58 is a side elevational view of the object of FIG. 57.

In another alternate embodiment (see FIG. 55) the aspiration port is located at the distal end of the assembly. Assembly 514 is identical in construction to assembly 14 shown in FIGS. 15 through 17. Aspiration port 516 in distal end 518 of assembly 514 communicates via a lumen having a dielectric coating with the lumen of tube 512, from which the flow path is identical to that of the embodiment of FIGS. 52 through 54. The aspiration functions in the same manner as the previous embodiment.

The placement of the aspiration port affects the manner in which bubbles are removed from the surgery site. For instance, assembly 414 will aspirate heated fluid and bubbles which are in close proximity to the top surfaces of the active and floating electrodes, and in doing so may lower the temperature of the fluid in the region thereby affecting the ablation performance and efficiency. Aspiration using the port placement of assembly 514 will have less effect on the temperature of the fluid surrounding the top surfaces of the active and floating electrodes and will therefore have less effect on the ablation process. Other placements of the aspiration port may also be used. In another alternate embodiment the aspiration port is placed in the ablating surface of the active electrode, with aspiration flow being via a lumen through the active electrode to the lumen of the distal tubular portion of the probe. Such placement allows the aspiration of bubbles directly from the ablation site, although flow must be carefully controlled to maintain acceptable ablation efficiency due to the likely removal of some process heat rather than waste heat by the aspiration flow. In yet another embodiment the aspiration port is in the region between the active and floating electrodes.

The use of a floating electrode to concentrate the energy field is useful for other configurations of electrosurgical devices as well. An alternate embodiment shown in FIGS. 56 through 60 has a blade-like distal portion for use in cutting tissue. Electrosurgical probe 600 has a proximal portion 602 forming a handle and a distal portion 604. Proximal portion 602 has buttons 606 and 608 for controlling an RF power supply connected to probe 600 by cord 610. As best seen in FIGS. 57 through 60, distal assembly 620 has an elongated flat first metallic member 622 forming a floating electrode, and a second metallic member 624 forming an active electrode and surrounding the perimeter of first member 622, members 622 and 624 being separated and electrically isolated by dielectric member 626. Second member 624 is connected by insulated wires 628 to the RF power supply such that when button 606 or 608 is depressed the appropriate output is supplied to active electrode 624. Dielectric member 626 is made of a suitable polymeric or ceramic material able to withstand high operating temperatures. As best seen in FIG. 60, second metallic member 624 has a perimeteral edge formed to a wedge shape having an included angle 630, and is made of a suitable material such as, for instance, stainless steel, nickel, tungsten or niobium. In another embodiment member 624 is a formed wire, and dielectric member 626 has a channel formed in its perimeteral surface, member 624 being positioned partially within the channel.

Figure 61:
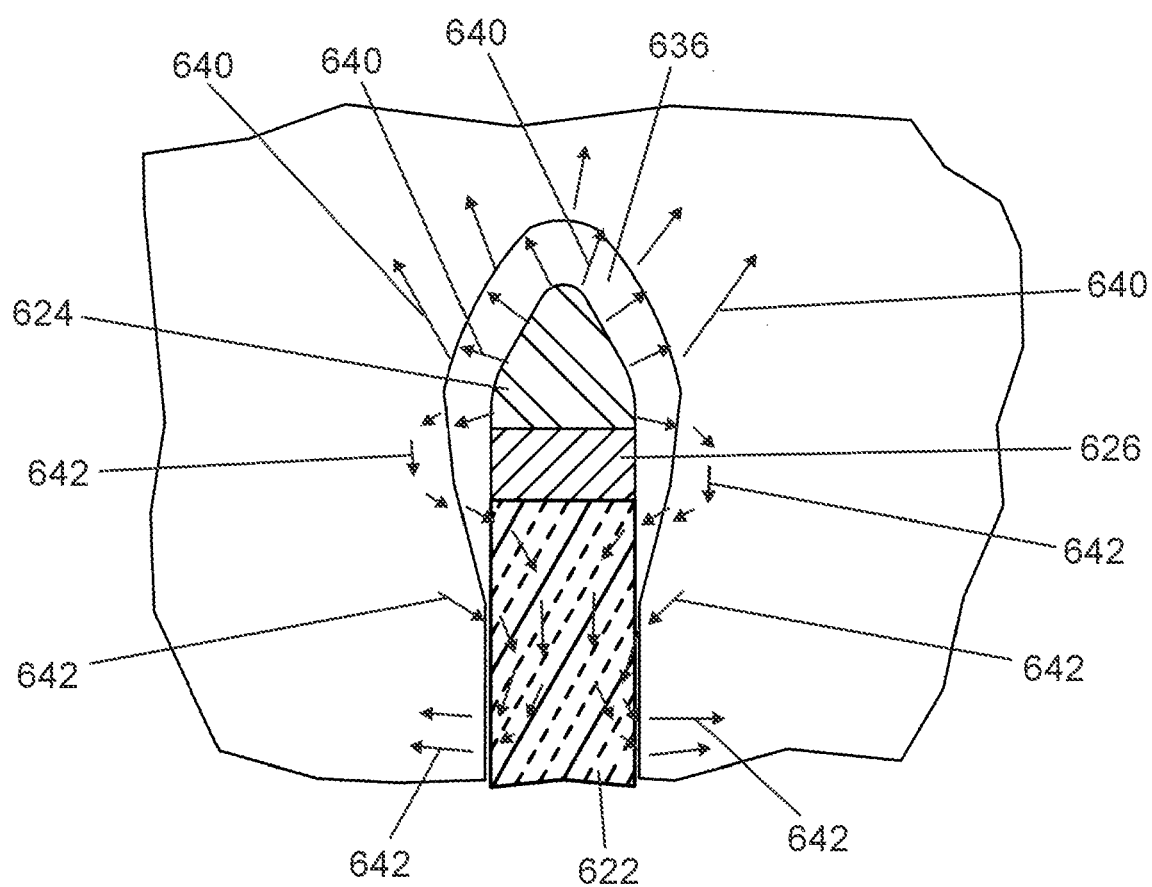
FIG. 61 is an expanded distal end sectional view of the object of FIG. 59 during use.

Referring now to FIG. 61 showing probe 600 during use, when assembly 620 is cutting tissue, an electric field is formed around active electrode 624. Floating electrode 622 has a region 632 near its perimeter in close proximity to active electrode 624 which is in the high-intensity region of the electric field, and a region 634 in a lower intensity region of the electric field. The effective "shorting together" of the regions of the electric field by the floating electrode intensifies the field in the region between the active electrode and the perimetral portion of the floating electrode causing increased heating in the region. Current flow during use is generally from the active electrode to the return electrode (dispersive pad) placed on the patient's body at a distance from the surgery site. The path taken will be determined by the location within the region surrounding assembly 620. A portion of the current 640 flows from active electrode 624 via arcs in gap 636 to the tissue and through the tissue to the return electrode. Arcing in gap 636 vaporizes tissue thereby enlarging the gap in the direction of the probe advancement. Another portion of the current 642 in the region in closer proximity to floating electrode 622 flows from active electrode 624 through gap 636 to the tissue, through the tissue to portion 632 of floating electrode 622 in the high-intensity region of the electric field, through floating electrode 632 to portion 634 in the lower intensity region of the electric field, and from portion 634 into the tissue and via the tissue to the return electrode.

When a standard uninsulated blade-type electrode is used to cut tissue, current flows from all uninsulated surfaces in contact with tissue or conductive liquid, the liquid being either supplied as irrigant or bodily fluids. In areas of high current density arcing causes vaporization of tissue. In areas of low current density tissue is coagulated and desiccated. Heating of the electrode by these processes causes charred tissue residue to adhere to the sides of the electrode thereby decreasing its efficiency. Probe 600, in contrast, has an active electrode 624 of limited surface area such that during use all of the surface in proximity to tissue or conductive liquid will have high current density. Dielectric member 626 serves as a thermal as well as electric insulator. Accordingly, active electrode 624 is subjected to very high temperatures which tend to vaporize tissue in contact with it and therefore have minimal buildup of tissue residue. Floating electrode 622 has high current densities and high temperatures in portion 632 of the electrode in close proximity to active electrode 624, and lower current density in the portions 634 of electrode 622 in the low intensity regions of the electric field. Accordingly, the overall temperature of floating electrode 622 is much less than that of a standard blade electrode and the buildup of tissue residue is diminished or eliminated.

Figure 62:
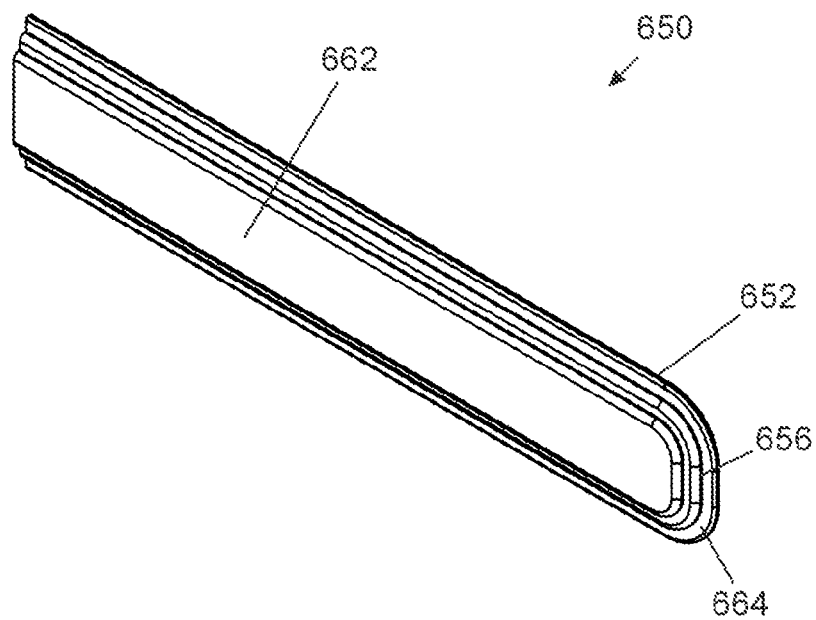
FIG. 62 is an expanded view of the distal portion of an alternate embodiment having the electrode assembly formed to a blade shape.
Figure 63:
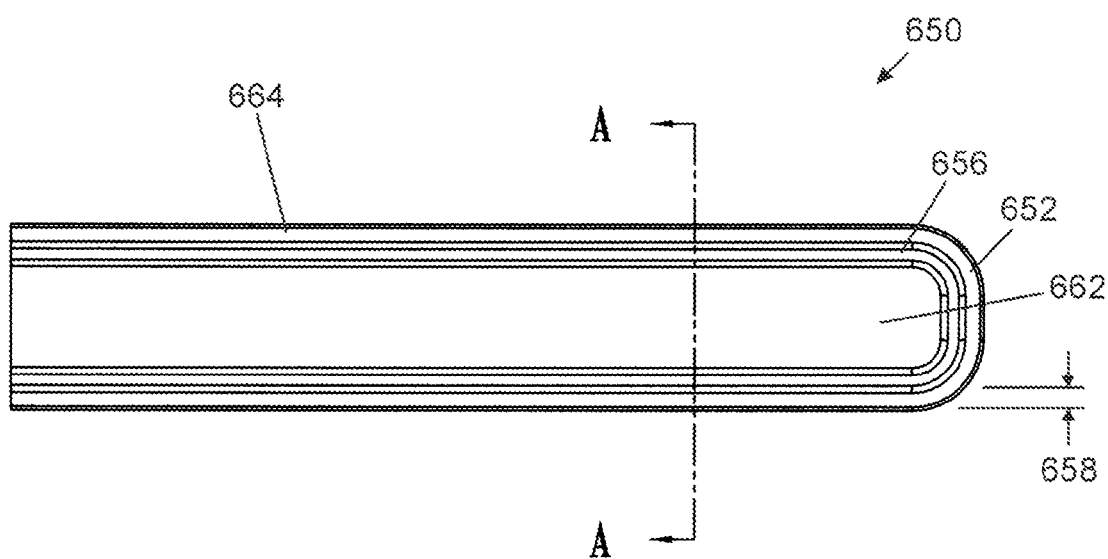
FIG. 63 is a side elevational view of the object of FIG. 62.
Figure 64:
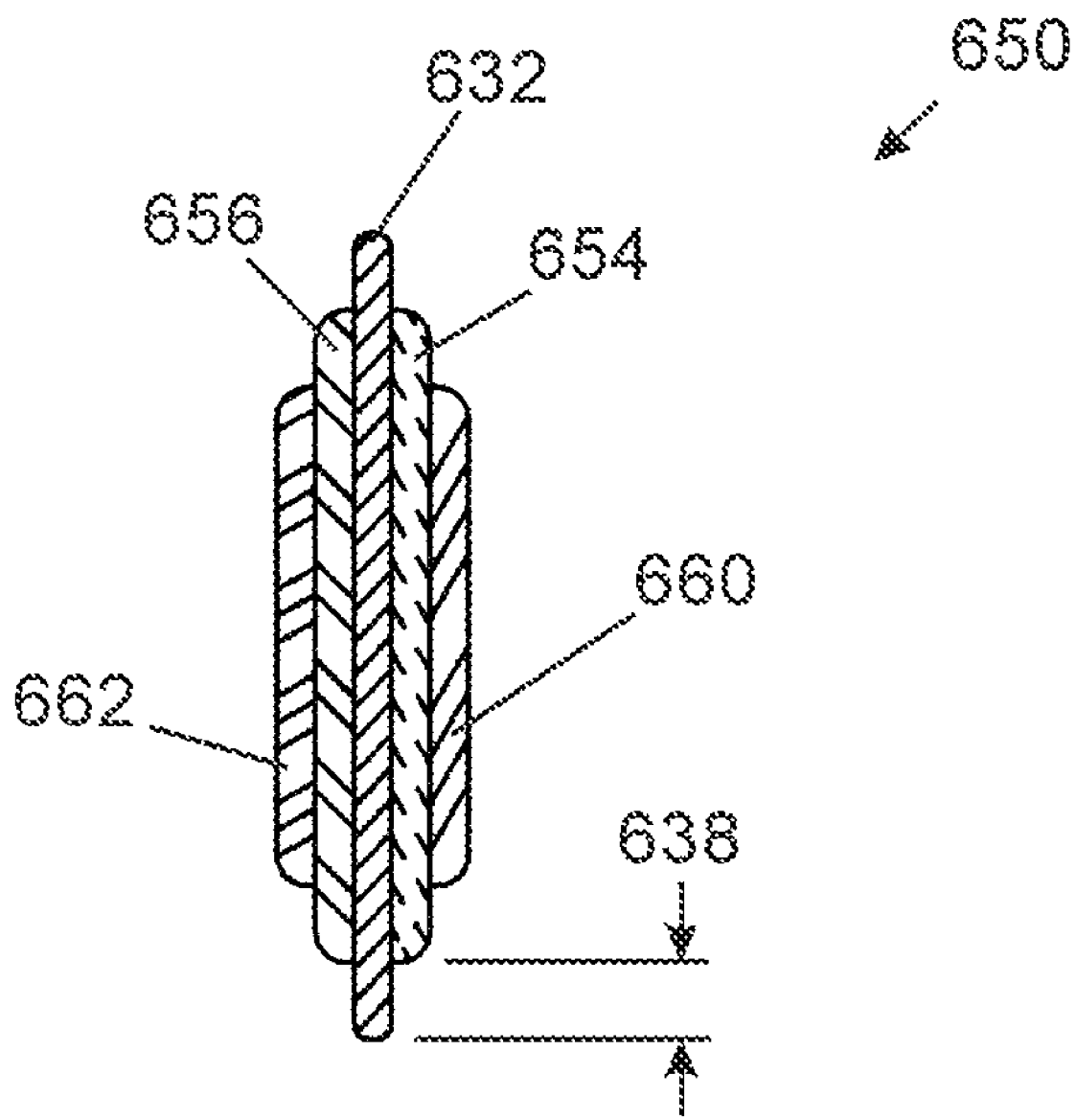
FIG. 64 is an expanded distal-end sectional view of the object of FIG. 63.

Other constructions of a blade-like distal assembly are possible. FIGS. 62 through 64 show a blade-like distal assembly formed from laminations. Assembly 650 has a first metallic member 652 which is electrically connected via a handle and cable to an electrosurgical generator so as to form an active electrode. Member 652 has a perimeter region 664 which protrudes beyond dielectric laminations 654 and 656 distance 658. Second metallic members 660 and 662 are electrically isolated from first metallic member 652 and form floating electrodes, not being connected to the electrosurgical power supply. Operation of the embodiment of FIGS. 62 through 64 is identical to that of FIGS. 56 through 60. Because member 652 protrudes beyond dielectric members 654 and 656 around the entire perimeter of assembly 650 the electrosurgical instrument may be used to cut in a forward or backward direction, or advanced distally into tissue. This may not always be desirable. For instance, for added safety in some situations it may be desirable to have only one active edge which will cut tissue. Embodiments are anticipated in which only selective portions of the active electrode are exposed, the remaining portions being surrounded by a dielectric member and, in some cases, a portion of the floating electrode.

Electrosurgical probes with radial symmetry constructed in accordance with principles of the invention described herein have an effective active diameter equal to the physical diameter of the working portion of the ablator. That is, the floating electrode (the portion of the ablator of largest diameter) becomes active, forming bubbles and arcs which vaporize tissue. This is in contrast to other electrosurgical devices in which the active electrode is surrounded by a larger diameter insulator. Because the devices of this invention have an active area equal to their physical area they can be advanced into tissue in a direction perpendicular to the ablating surfaces, creating in the tissue a self supporting channel much in the manner of a drill. This is not possible with other probes which have a working diameter less than their physical diameter. With these probes significant advancement into tissue is prevented by the physical size of the insulator.

Figure 65:
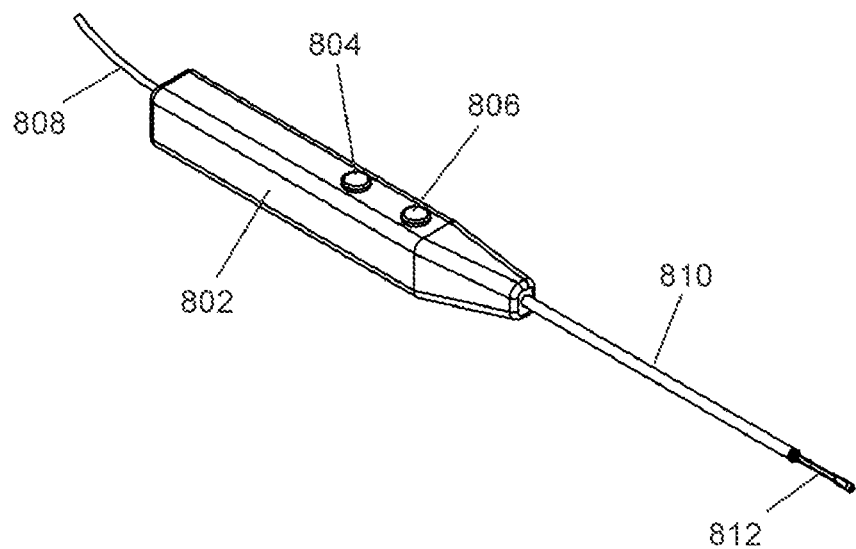
FIG. 65 is a perspective view of an alternate embodiment configured to produce holes in tissue.
Figure 66:
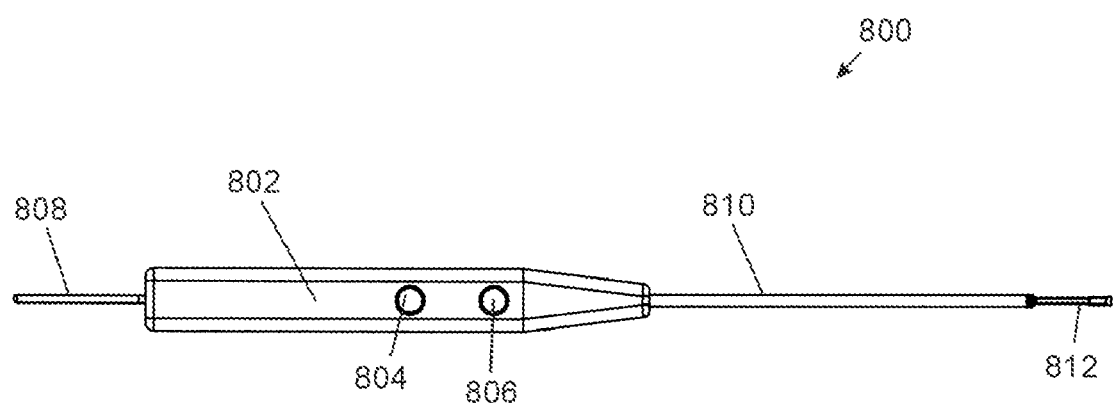
FIG. 66 is a plan view of the object of FIG. 65.
Figure 67:
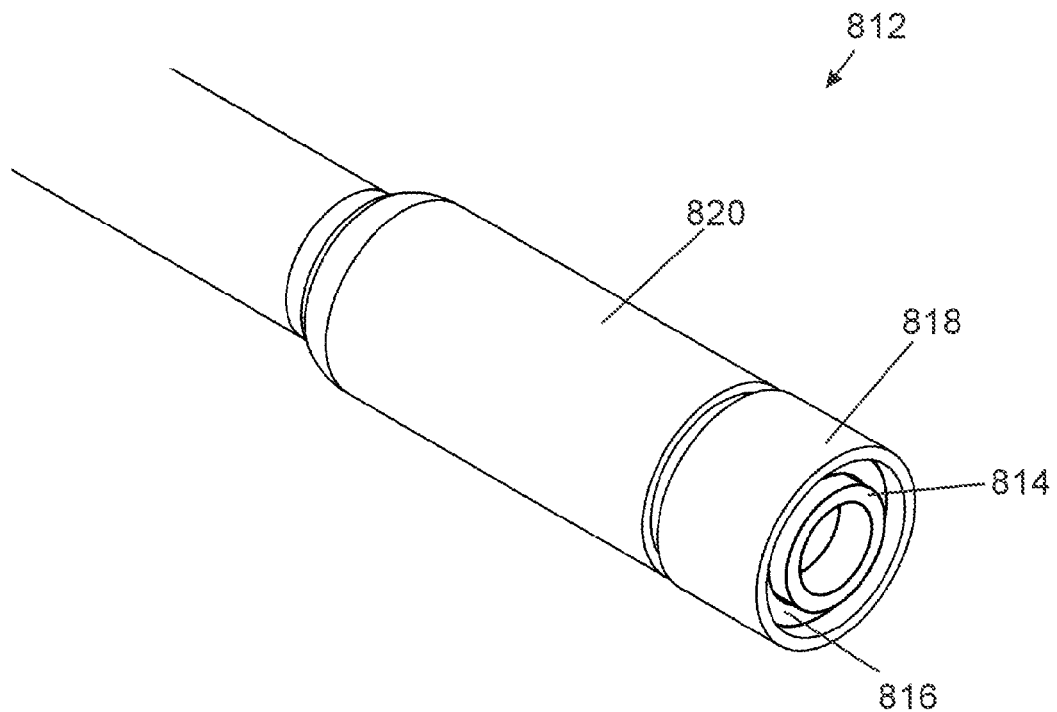
FIG. 67 is an expanded perspective view of the distal end of the object of FIG. 65.
Figure 68:
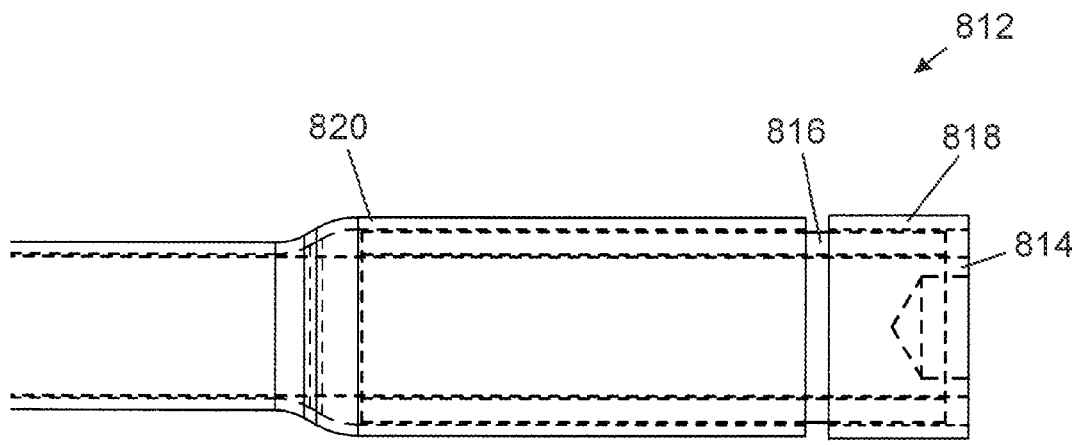
FIG. 68 is an expanded side elevational view of the object of FIG. 65.

A probe constructed in accordance with the principles of this invention for producing holes in tissue is shown in FIGS. 65 through 68. As best seen in FIGS. 65 and 66, probe 800 is similar in construction to other non-aspirating embodiments herein described having a proximal handle portion 802 with buttons 804 and 806 for controlling and electrosurgical power supply to which it is connected by cable 808. Distal portion 810 has a distal tip assembly 812. Referring now to FIGS. 67 and 68, distal tip assembly 812 has an active electrode 814 separated by insulator 816 from floating electrode 818. Dielectric coating 820 covers a proximal portion of insulator 816, a proximal portion of active electrode 814, and the rest of distal portion 810.

Figure 69:
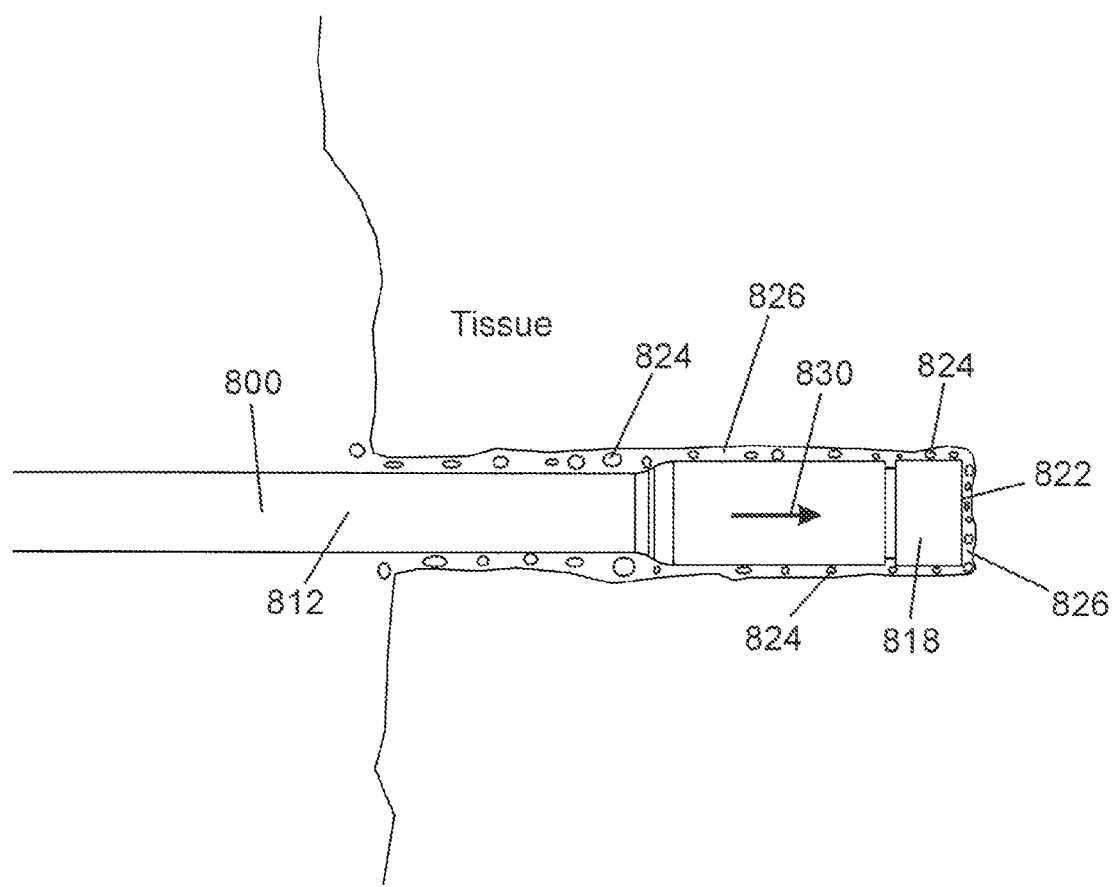
FIG. 69 is a side elevational view of the distal portion of the object of FIG. 65 during use.

Referring now to FIG. 69, during use electrode 800 is advanced distally 830 into the tissue, the distal surfaces of the active electrode (not shown) and distal surface 822 of floating electrode 818 having current density sufficient to cause vaporization of tissue. Bubbles 824 and products of the vaporization are expelled proximally through gap 826 formed between distal assembly 812 and the tissue. Lower current density heating from the more proximal region 824 of floating electrode 818 desiccates tissue with which it is in contact so as to stop bleeding. The site may be submerged in a conductive liquid, conductive liquid may be supplied to the site as an irrigant, and conductive bodily fluids may be utilized in the hole making process.

Figure 70:
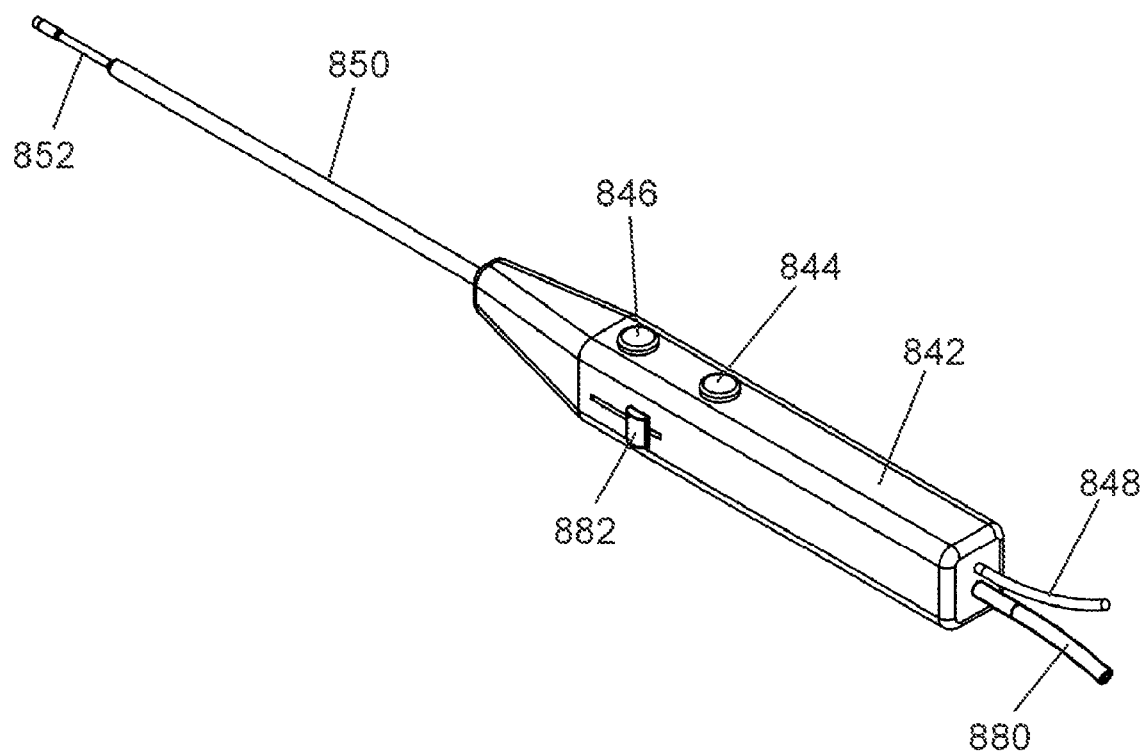
FIG. 70 is a perspective view of an alternate embodiment configured to produce holes in tissue, and having a means for supplying conductive liquid to the probe tip.
Figure 71:
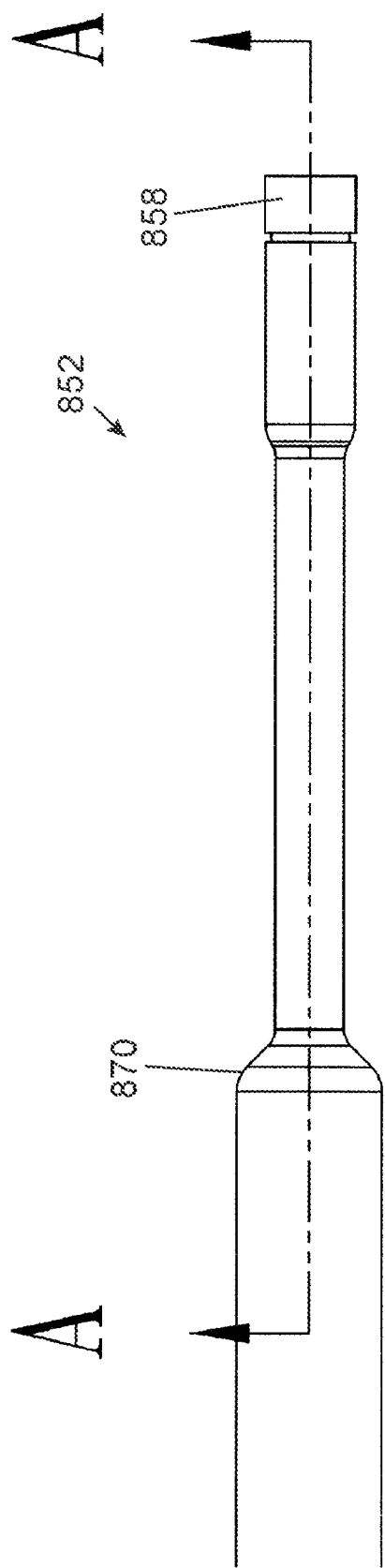
FIG. 71 is an expanded plan view of the distal end of the object of FIG. 70.
Figure 72:
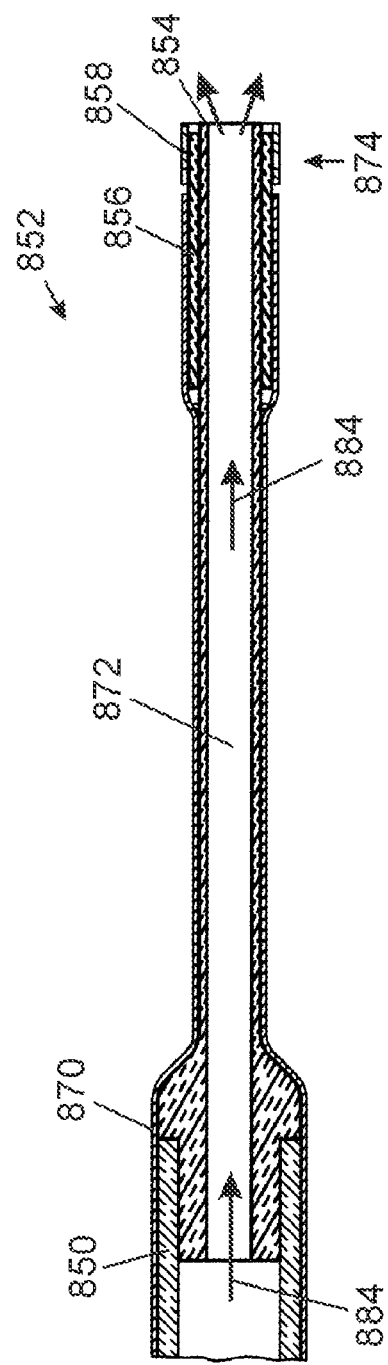
FIG. 72 is an expanded side sectional view of the distal end of the object of FIG. 70.

In certain circumstances, such as when making holes with large depth to diameter ratios, it may be desirable to supply conductive fluid to the probe distal end. An embodiment incorporating such a fluid supply means is shown in FIGS. 70 through 72. Electrosurgical probe 840 is similar in construction to probe 800, probe 840 having a proximal handle portion 842 with buttons 844 and 846 for controlling an electrosurgical power supply to which it is connected by cable 848. Distal portion 850 has a distal tip assembly 852. Tube 880 is connected to a source of conductive liquid which is supplied via a means in handle 842 and a lumen in distal portion 850 to distal tip assembly 852. Control means 882 regulates the amount of liquid supplied to tip assembly 852. Referring now to FIGS. 71 and 72, distal tip assembly 852 has an active electrode 854 separated by insulator 856 from floating electrode 858. Dielectric coating 870 covers a proximal portion of insulator 856, a proximal portion of active electrode 854, and the rest of distal portion 850. Lumen 872 supplies conductive liquid 884 to distal end 874 of active electrode 854 and the region surrounding electrode 854, insulator 856 and the distal end of floating electrode 858.

Figure 73:
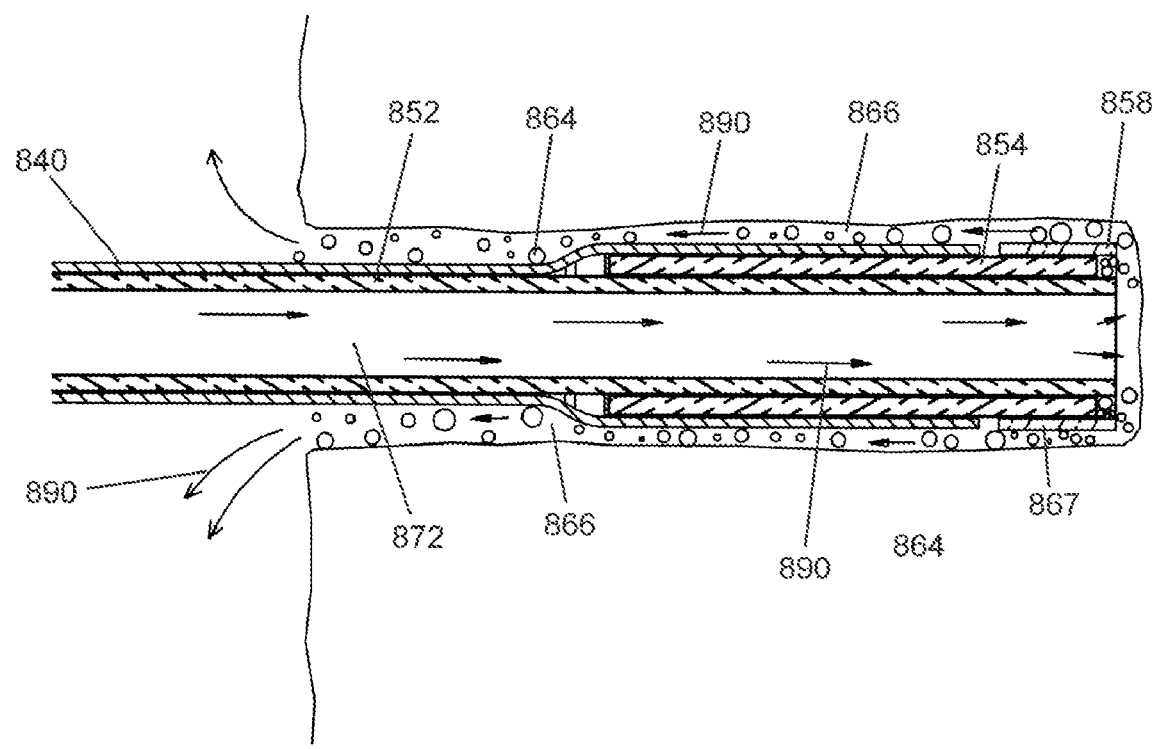
FIG. 73 is an expanded side sectional view of the distal end of the object of FIG. 70 during use.
Figure 74:
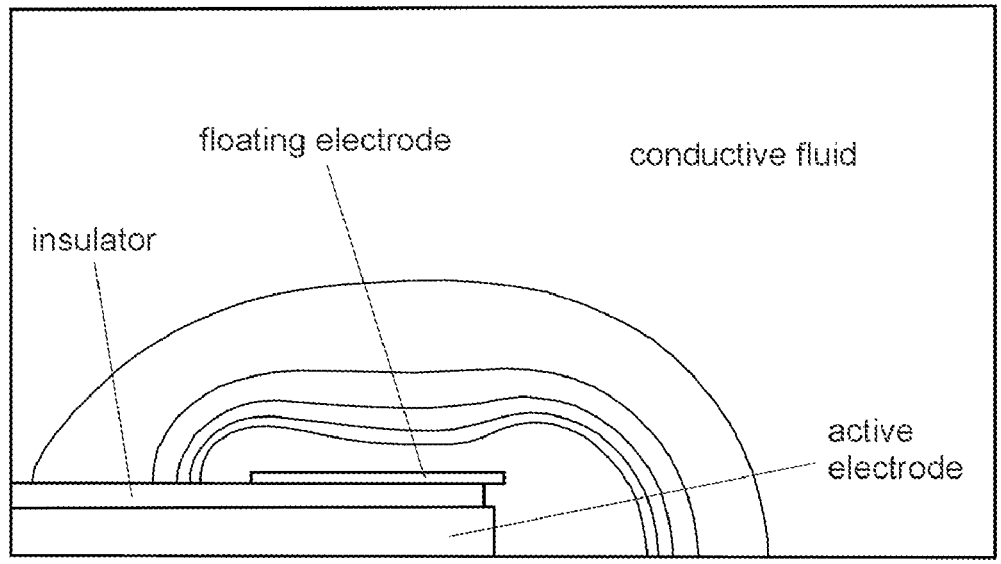
FIG. 74 is a plot of the power density in the region surrounding the distal end of an electrosurgical probe with a floating electrode submerged in a conductive liquid.
Figure 75:
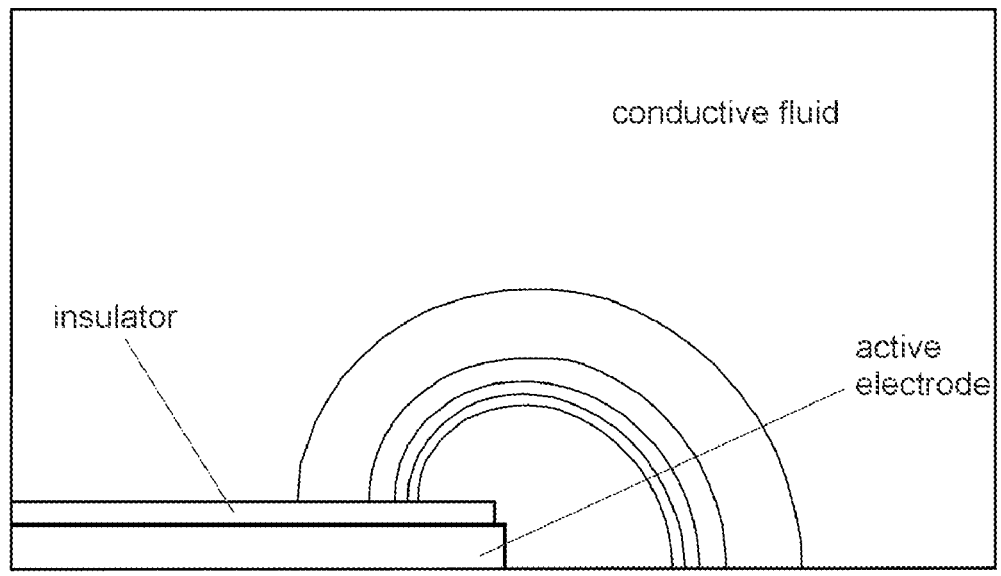
FIG. 75 is a plot of the power density in the region surrounding the distal end of an electrosurgical probe submerged in a conductive liquid.
Figure 76:
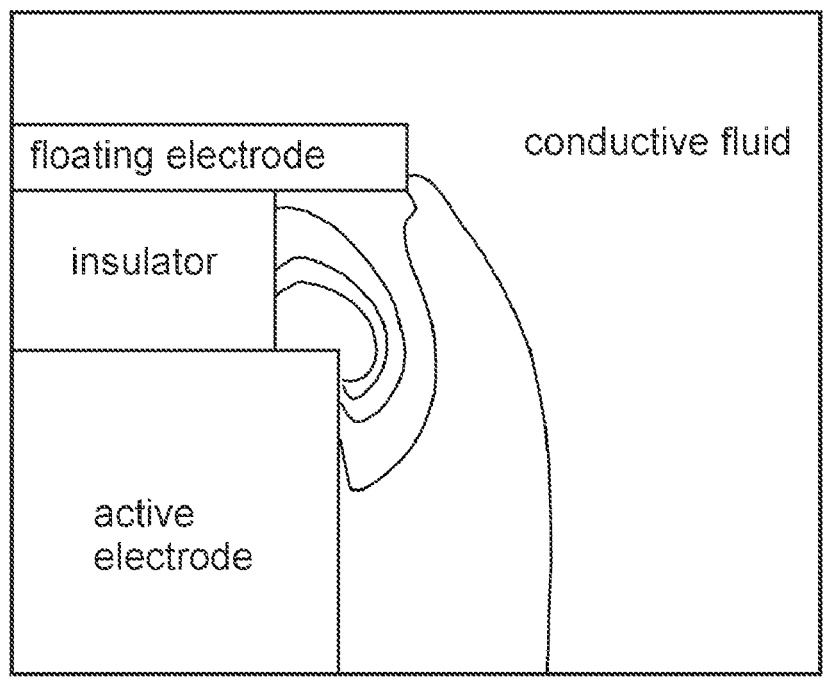
FIG. 76 is an expanded plot of the power density in the region surrounding the active electrode of an electrosurgical probe with a floating electrode submerged in a conductive liquid.
Figure 77:
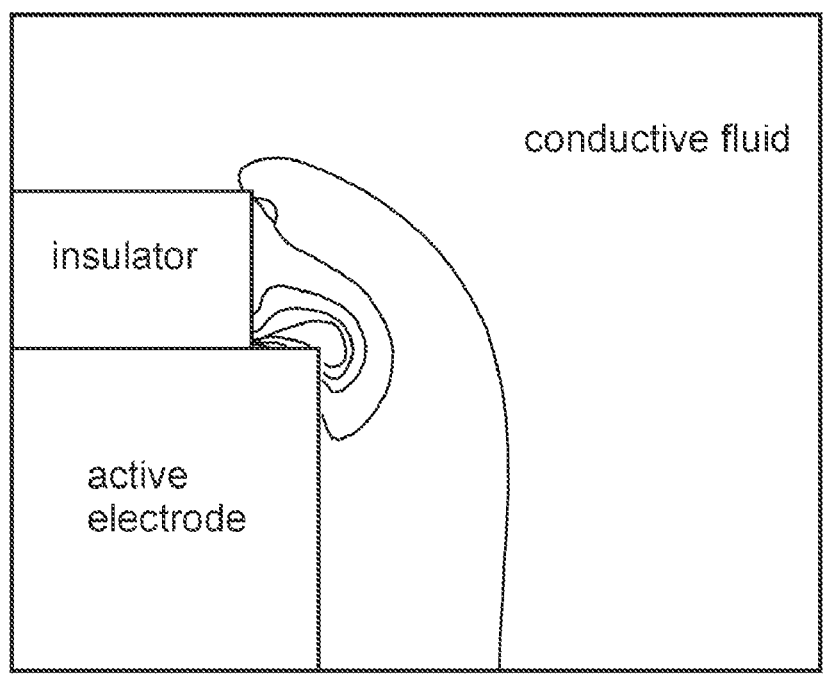
FIG. 77 is an expanded plot of the power density in the region surrounding the active electrode of an electrosurgical probe submerged in a conductive liquid.
Figure 78:
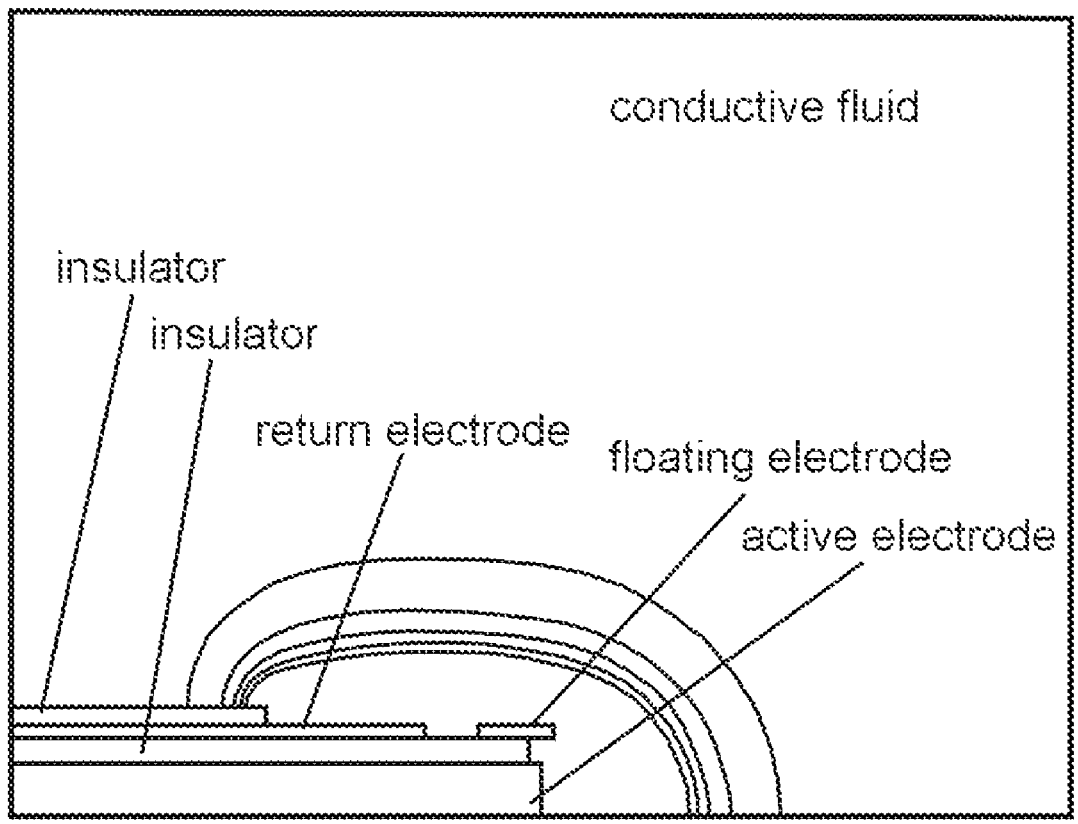
FIG. 78 is a plot of the power density in the region surrounding the distal end of an electrosurgical probe having a return electrode mounted on the probe, and having a floating electrode, submerged in a conductive liquid.
Figure 79:
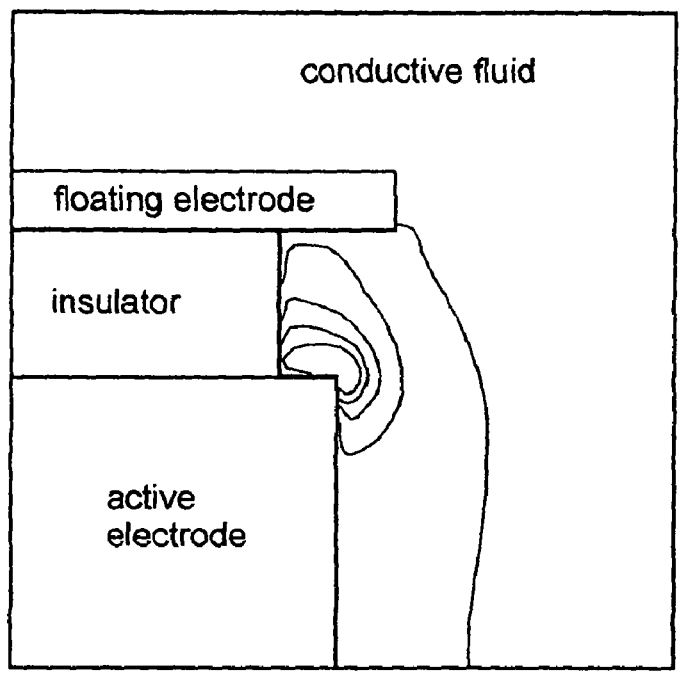
FIG. 79 is an expanded plot of the power density in the region surrounding the active electrode of the probe with a return electrode mounted on the probe and a floating electrode shown in FIG. 78.
Figure 80:
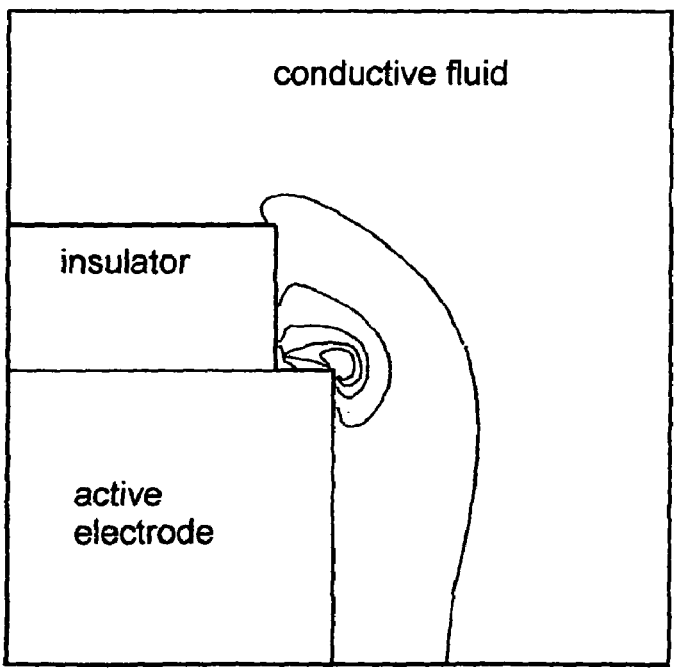
FIG. 80 is an expanded plot of the current density in the region surrounding the active electrode of a probe with a return electrode submerged in a conductive liquid.

Referring now to FIG. 73, during use probe 840 is advanced distally into the tissue, distal surface 888 of active electrode 854 and distal surface 892 of floating electrode 858 having current density sufficient to cause vaporization of tissue. Conductive liquid 890 supplied by lumen 872 fills the region surrounding the probe tip and helps flush bubbles 864 and products of tissue vaporization proximally through gap 866 formed between distal assembly 852 and the tissue. Lower current density heating from the more proximal region 867 of floating electrode 858 desiccates tissue with which it is in contact so as to stop bleeding.

The embodiments previously herein described are used with a return electrode affixed to the patient at a remote location. These embodiments may be modified by adding a return electrode to the probe so as to create other embodiments which are also within the scope of this invention. The intensification of the power in the active region occurs regardless of the location of the return electrode.

Heretofore the applications for electrosurgical probes constructed in accordance with the principles of the invention described herein have been for the vaporizing of tissue. The current invention is useful for non-vaporizing applications such as lesion formation also. For such use the voltage applied to the probe is limited so that the maximum temperatures generated are below the boiling point of water. This prevents steam bubble formation and the associated arcing within the bubbles. When forming a lesion on a surface or inside the bulk of the tissue (interstitial) the size of the lesion formed is strongly affected by the size and shape of the electrode, the level of the applied power, and the duration for which power is applied. It is necessary to apply sufficiently high power to form a lesion, but still not too high in order to avoid vaporization and or tissue charring. The heating effect of an electrode surface in contact with tissue is nonuniform with higher current density and heating at and near the perimeter of the surface. Lesions produced by such electrodes are also nonuniform.

When using an electrosurgical probe of the current invention to thermally treat tissue, the probe distal end is positioned such that the active electrode and floating electrode are both in contact with the tissue at the site for lesion formation. A voltage is applied to the active electrode to cause heating of the tissue in contact with the active electrode sufficient to cause lesion formation, but below the threshold needed for vaporization. Current flows from the active electrode into the tissue. Some current goes directly through the tissue to the return electrode. A portion of the current goes from the active electrode to the portion of the floating electrode which is in close proximity in the high-intensity region of the electric field. This current flows through the floating electrode and exits in the low-potential portion of the electrode to flow through conductive fluid or tissue with which this portion of the floating electrode is in contact to the return electrode. The portion of the floating electrode in close proximity to the active electrode has regions of high current density and therefor heating sufficient to cause lesion formation. Accordingly, for a given power level it is possible to create a larger and more uniform lesion using a probe of the current invention than when using a standard probe.

The electrosurgical probe having a floating electrode as taught herein may be employed for a variety of arthroscopic procedures, for example, in the dissection, resection, vaporization, desiccation and coagulation of tissue structures in various endoscopic and percutaneous procedures performed on joints of the body.

The electrosurgical device of the present invention may be also used in hysteroscopic surgical procedures or urological endoscopic (urethroscopy, cystoscopy, ureteroscopy and nephroscopy) and percutaneous interventions. Hysteroscopic procedures may include: removal of submucosal fibroids, polyps and malignant neoplasms; resection of congenital uterine anomalies such as a septum or subseptum; division of synechiae (adhesiolysis); ablation of diseased or hypertrophic endometrial tissue; and haemostasis. Urological procedures may include: electro-vaporization of the prostate gland (EVAP) and other similar procedures commonly referred to as transurethral resection of the prostate (TURP) including, but not limited to, interstitial ablation of the prostate gland by a percutaneous or perurethral route whether performed for benign or malignant disease; transurethral or percutaneous resection of urinary tract tumors; division of strictures as they may arise at the pelviureteric junction (PUJ), ureter, ureteral orifice, bladder neck or urethra; correction of ureterocoele, among others.

The electrosurgical device of the present invention may be also be used advantageously in ENT (ear, nose, throat) for treating tonsils and upper airways obstruction, as well as for GI, oncology and cardiology.

Indeed, the present invention may be used advantageously in virtually all fields of electrosurgery.

What is claimed is:

1. A bipolar electrosurgical probe comprising:
   a. a shaft having a proximal end and a distal end;
   b. at least one active electrode located at or near the distal end of said shaft, wherein said at least one active electrode is connected to a power supply;
   c. a conductor connected to said at least one active electrode;
   d. a return current electrode disposed on the shaft in moderate proximity to the at least one active electrode;
   e. at least one conductive member disposed at the distal end, wherein said at least one conductive member comprises a floating electrode that is not connected to a power supply; and
   f. a dielectric member disposed between the at least one active electrode and the at least one conductive member, wherein said at least one conductive member has an exposed surface defined by a distal portion disposed in a region of higher potential and a proximal portion disposed in a region of lower potential, further wherein the distal portion is positioned in close proximity to an end of the at least one active electrode such that current flows from the active electrode to the conductive member then toward the return electrode, so as to concentrate the power in the vicinity of the active electrode and increase the energy density in the region surrounding the active electrode.

2. The probe of claim 1 wherein said at least one active electrode and said return current electrode are separated by a distance of about 2 to 10 millimeters.

3. The probe of claim 1 wherein said at least one active electrode and said at least one conductive member are separated by a distance of about 0.1 to 10 millimeters.

4. The probe of claim 3 wherein said at least one active electrode and said at least one conductive member are separated by a distance of about 0.2 to 4 millimeters.

5. The electrosurgical probe of claim 1 wherein said at least one active electrode and the distal portion of said at least one conductive member extends distally past an end of the dielectric member.

6. The electrosurgical probe of claim 1 wherein said distal portion of said at least one conductive member extends distally past a distal portion of said at least one active electrode.

7. The electrosurgical probe of claim 6 wherein said distal portion of said at least one conductive member is tapered.

8. The electrosurgical probe of claim 6 wherein said distal portion of said at least one active electrode is angled.

9. The electrosurgical probe of claim 1 wherein said distal portion of said at least one conductive member is adjacent to a proximal portion of said at least one active electrode.

10. The electrosurgical probe of claim 1 wherein said distal portion of said at least one conductive member extends between a distal and proximal portion of said at least one active electrode.

11. The electrosurgical probe of claim 1 wherein said at least one conductive member comprises a plurality of protuberances.

12. The electrosurgical probe of claim 1 wherein said at least one active electrode comprises a plurality of protuberances.

13. The electrosurgical probe of claim 12 wherein said protuberances comprise a plurality of ribs separated by grooves.

14. The electrosurgical probe of claim 1 wherein said at least one active electrode forms an annulus with the at least one conductive member.

15. The electrosurgical probe of claim 1 wherein said at least one conductive member comprises an annular ring disposed about said at least one active electrode.

16. The electrosurgical probe of claim 1 wherein said at least one active electrode and said at least one conductive member form an array of protuberances in which the active and floating electrodes are interspersed.

17. The electrosurgical probe of claim 1 wherein said distal portion of said at least one conductive member forms a distal surface, said surface comprising a plurality of lumens, and said protuberances passing through said lumens and protruding distally beyond the distal surface.

18. The electrosurgical probe of claim 1 wherein said dielectric member is made from a refractory material.

19. The electrosurgical probe of claim 1 further comprising a means for supplying conductive fluid to the shaft distal end.

20. The electrosurgical probe of claim 19, wherein said means for supplying conductive fluid comprises at least one lumen disposed along the length of said shaft, said lumen having a first port disposed at the proximal end of said shaft and a second port disposed at the distal end of said shaft.

21. The electrosurgical probe of claim 1 further comprising a means for aspirating liquid and ablation products from the region of the probe distal end.

22. A method for thermally treating tissue at a site on a patient comprising the steps of:
   providing the bipolar electrosurgical probe according to claim 1;
   positioning a distal end of said probe in close proximity to tissue to be ablated;
   submerging the distal end of said probe in a conductive liquid; and
   applying high frequency voltage between said at least one active electrode and said return electrode to heat a portion of the tissue.

23. The method of claim 22 in which said conductive liquid comprises a bodily fluids from the patient.

24. The method of claim 22 in which said conductive liquid comprises an irrigant supplied to the region surrounding said distal end of said probe.

25. The method of claim 22 in which said conductive liquid substantially fills a natural or created cavity in the body of a patient.

26. The method of claim 22 wherein the portion of tissue is heated to a degree to permit vaporization.

27. A system for the electrosurgical ablation or thermal treatment of tissue comprising:
   a. an electrosurgical generator;
   b. a bipolar electrosurgical probe accordingly to claim 1; and
   c. cabling connecting said bipolar electrosurgical probe to said generator.

* * * * *